(12) United States Patent
Payne et al.

(10) Patent No.: US 11,905,321 B2
(45) Date of Patent: Feb. 20, 2024

(54) COMPOSITIONS AND METHODS OF MUSCLE SPECIFIC KINASE CHIMERIC AUTOANTIBODY RECEPTOR CELLS

(71) Applicant: THE TRUSTEES OF THE UNIVERSITY OF PENNSYLVANIA, Philadelphia, PA (US)

(72) Inventors: Aimee S. Payne, Merion Station, PA (US); Christoph T. Ellebrecht, Philadelphia, PA (US); Sangwook Oh, Wynnewood, PA (US); Michael C. Milone, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/431,402

(22) Filed: Jun. 4, 2019

(65) Prior Publication Data

US 2019/0375817 A1    Dec. 12, 2019

Related U.S. Application Data

(60) Provisional application No. 62/680,769, filed on Jun. 5, 2018.

(51) Int. Cl.
*C07K 14/705* (2006.01)
*C07K 16/28* (2006.01)

(52) U.S. Cl.
CPC .... *C07K 14/70517* (2013.01); *C07K 16/2815* (2013.01); *C07K 2319/02* (2013.01); *C07K 2319/03* (2013.01)

(58) Field of Classification Search
CPC .......... C07K 14/70517; C07K 16/2815; C07K 2319/02; C07K 2319/03; C07K 2319/33; C07K 14/705; C07K 14/70578; C07K 14/7051; C12N 9/12; C12N 15/62; C12Y 207/10001; A61K 35/17; A61K 39/0008; A61K 2039/5156; A61K 2039/5158; A61P 21/00
See application file for complete search history.

(56) References Cited

U.S. PATENT DOCUMENTS

| | | | |
|---|---|---|---|
| 5,350,674 A | 9/1994 | Boenisch et al. | |
| 5,585,362 A | 12/1996 | Wilson et al. | |
| 5,858,358 A | 1/1999 | June et al. | |
| 5,883,223 A | 3/1999 | Gray | |
| 6,120,766 A | 9/2000 | Hale et al. | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 9,574,015 B2 | 2/2017 | Burden et al. | |
| 2006/0121005 A1 | 6/2006 | Berenson et al. | |
| 2014/0050708 A1 | 2/2014 | Powell et al. | |
| 2016/0046724 A1 | 2/2016 | Brogdon et al. | |

FOREIGN PATENT DOCUMENTS

| | | |
|---|---|---|
| WO | 9721811 A2 | 6/1997 |
| WO | 2004063362 A2 | 7/2004 |
| WO | 2013151672 A2 | 10/2013 |
| WO | 2015039015 A2 | 3/2015 |
| WO | 2015168613 A2 | 11/2015 |
| WO | 2018127585 | 7/2018 |

OTHER PUBLICATIONS

International Search Report and Written Opinion for PCT International Application No. PCT/US2019/035409 dated Oct. 18, 2019.
Budde, et al., "Combining a CD20 chimeric antigen receptor and an inducible caspase 9 suicide switch to improve the efficacy and safety of T cell adoptive immunotherapy for lymphoma", PLOS One 8(12), Dec. 2013, e82742.
Chen, et al., "Genetic control of mammalian T-cell proliferation with synthetic RNA regulatory systems", Proc Natl Acad Sci U S A 107(19), May 2010, 8531-8536.
Di Stasi, et al., "Inducible apoptosis as a safety switch for adoptive cell therapy", N Engl J Med. 365(18), Nov. 2011, 1673-1683.
Fedorov, et al., "Novel approaches to enhance the specificity and safety of engineered T cells", Cancer J. 20(2), Apr. 2014, 160-165 (abstract only).
Hill, et al., "Human antibody-based chemically induced dimerizers for cell therapeutic applications", Nat Chem Biol. 14(2), Feb. 2018, 112-117.
Huijbers, et al., "MuSK IgG4 autoantibodies cause myasthenia gravis by inhibiting binding between MuSK and Lrp4", Proc Natl Acad Sci U S A. 110(51), Dec. 2013, 20783-20788.
Kloss, et al., "Combinatorial antigen recognition with balanced signaling promotes selective tumor eradication by engineered T cells.", Nat Biotechnol. 31(1), Jan. 2013, 71-75.
Kudo, et al., "T lymphocytes expressing a CD16 signaling receptor exert antibody-dependent cancer cell killing", Cancer Res. 74(1), Jan. 2014, 93-103.
Ma, et al., "Versatile strategy for controlling the specificity and activity of engineered T cells", Proc Natl Acad Sci U S A 113(4), Jan. 2016, E450-458.

(Continued)

*Primary Examiner* — Olga N Chernyshev
(74) *Attorney, Agent, or Firm* — Saul Ewing LLP; Kathryn Doyle

(57) ABSTRACT

The invention includes a chimeric autoantibody receptor (CAAR) specific for anti-muscle-specific kinase (MuSK) B cell receptor (BCR), compositions comprising the CAAR, polynucleotides encoding the CAAR, vectors comprising a polynucleotide encoding the CAAR, and recombinant cells comprising the CAAR.

15 Claims, 20 Drawing Sheets

Specification includes a Sequence Listing.

(56) References Cited

OTHER PUBLICATIONS

Rodgers, et al., "Switch-mediated activation and retargeting of CAR-T cells for B-cell malignancies", roc Natl Acad Sci U S A 113(4), Jan. 2016, E459-68.
Roybal, et al., "Precision Tumor Recognition by T Cells With Combinatorial Antigen Sensing Circuits", Cell. 164(4), Feb. 2016, 770-779.
Sakemura, et al., "A Tet-On Inducible System for Controlling CD19-Chimeric Antigen Receptor Expression upon Drug Administration.", Cancer Immunol Res. 4(8), Jun. 2016, 658-68.
Wei, et al., "Bacterial virulence proteins as tools to rewire kinase pathways in yeast and immune cells", Nature 488(7411), Aug. 2012, 384-388.
Wu, et al., "Remote control of therapeutic T cells through a small molecule-gated chimeric receptor", Science 350(6258), Oct. 2015, aab4077.
Zhang, et al., "Agrin binds to the N-terminal region of Lrp4 protein and stimulates association between Lrp4 and the first immunoglobulin-like domain in muscle-specific kinase (MuSK)", J Biol Chem. 286(47), Nov. 2011, 40624-40630.
Extended European Search Report issued in App. No. EP19815234.0, dated Feb. 23, 2022, 16 pages.
Ralf J. Ludwig et al: "Mechanisms of Autoantibody-Induced Pathology", Frontiers in Immunology, vol. 8, May 31, 2017 (May 31, 2017), XP055420435.
C. T. Ellebrecht et al, "Reengineering chimeric antigen receptor T cells for targeted therapy of autoimmune disease", Science, US, (Jul. 8, 2016), vol. 353, No. 6295, doi:10.1126/science.aaf6756, ISSN 0036-8075, pp. 179-184, XP055434542.
Panos Stathopoulos, et al., "Mechanisms underlying B cell immune dysregulation and autoantibody production in MuSK MG", Ann N Y Acad Sci., Jan. 2018, vol. 1412, No. 1, pp. 154-165.

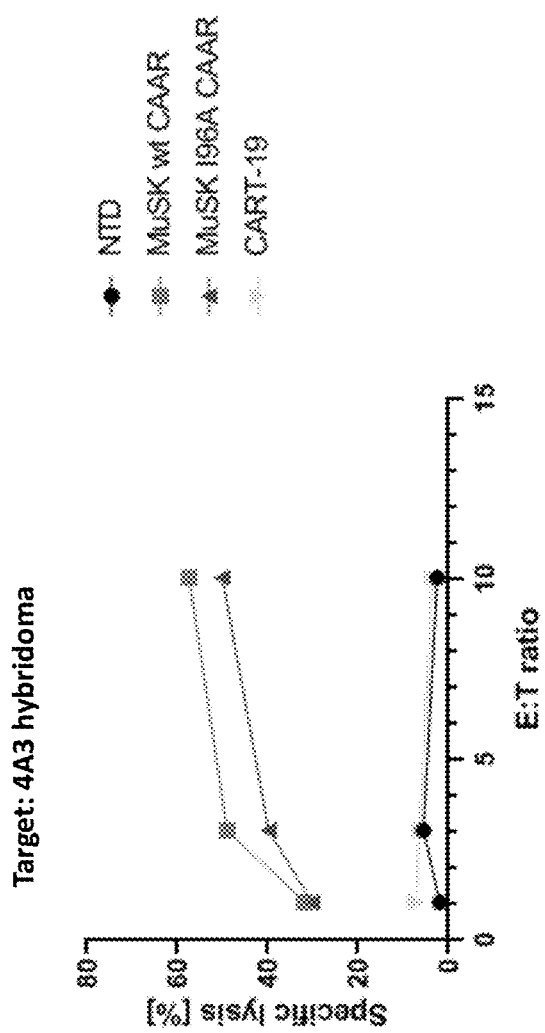
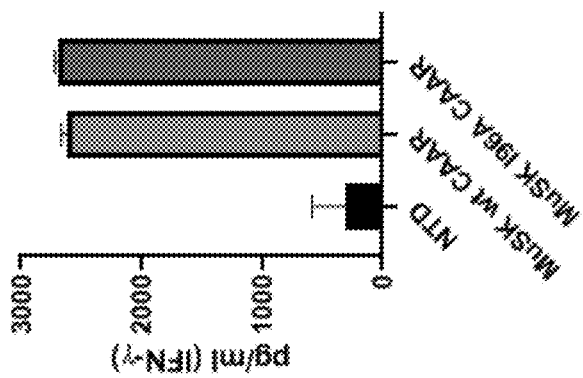
FIG. 11A
FIG. 11B

```
                         SEQUENCE LISTING

<160> NUMBER OF SEQ ID NOS: 32

<210> SEQ ID NO 1
<211> LENGTH: 2058
<212> TYPE: DNA
<213> ORGANISM: Artificial Sequence
<220> FEATURE:
<223> OTHER INFORMATION: pTRPE.MuSKWT.BBz CAAR

<400> SEQUENCE: 1
atggagtttg ggctgagctg gctttttctt gtggctattt taaaaggtgt ccagtgcgga      60
tcccttccaa aagctcctgt catcaccact cctcttgaaa cagtggatgc cttagttgaa     120
gaagtggcta ctttcatgtg tgcagtggaa tcctaccccc agcctgagat ttcctggact     180
agaaataaaa ttctcattaa actctttgac acccggtaca gcatccggga gaatgggcag     240
ctcctcacca tcctgagtgt ggaagacagt gatgatggca tttactgctg cacggccaac     300
aatggtgtgg gaggagctgt ggagagttgt ggagccctgc aagtgaagat gaaacctaaa     360
ataactcgcc ctcccataaa tgtgaaaata atagagggat taaaagcagt cctaccatgt     420
actacaatgg gtaatcccaa accatcagtg tcttggataa agggagacag ccctctcagg     480
gaaaattccc gaattgcagt tcttgaatct gggagcttga ggattcataa cgtacaaaag     540
gaagatgcag gacagtatcg atgtgtggca aaaaacagcc tcgggacagc atattccaaa     600
gtggtgaagc tggaagttga ggtttttgcc aggattctgc gggctcctga atcccacaat     660
gtcacctttg gctcctttgt gacccctgcac tgtacagcaa caggcattcc tgtccccacc     720
atcacctgga ttgaaaacgg aaatgctgtt tcttctgggt ccattcaaga gagtgtgaaa     780
gaccgagtga ttgactcaag actgcagctg tttatcacca agccaggact ctacacatgc     840
atagctacca ataagcatgg ggagaagttc agtactgcca aggctgcagc caccatcagc     900
atagcagaat ggagtaaacc acagaaagat aacaaaggct actgcgccca gtacagaggg    960
```

```
gaggtgtgta atgcagtcct ggcaaaagat gctcttgttt ttctcaacac ctcctatgcg     1020
gaccctgagg aggcccaaga gctactggtc cacacggcct ggaatgaact gaaagtagtg     1080
agcccagtct gccggccagc tgctgaggct ttgttgtgta accacatctt ccaggagtgc     1140
agtcctggag tagtgcctac tcctattccc atttgcagag agtactgctt ggcagtaaag     1200
gagctcttct gcgcaaaaga atggctggta atggaagaga agacccacag aggactctac     1260
agatccgaga tgcatttgct gtccgtgcca gaatgcagca agcttcccag catgcattgg     1320
gaccccacgg cctgtgccag actgccacat ctagattata caaagaaaa cctaaaaaca     1380 ttcccaccaa tgacgtcctc aaagccaagt gtggacattc caaatctgcc ttcctcctcc     1440
tcttcttcct tctctgtctc acctacatac tccatgactg ctagcggagg tggaggtagt     1500
ggcggtggag gcagctctgg tatctacatc tgggcaccct tggctggaac atgcggggtc     1560
ctgctgctga gcttggtgat caccctttac tgcaagcgcg gtcgcaagaa actgctctat     1620 attttaaac agccattcat gagacctgtc cagaccactc aagaggagga cggatgttcc     1680
tgtagatttc ctgaagagga agaggggggg tgcgagctga gagtaaagtt cagtaggtcc     1740
gccgatgccc cagcctatca acaggggcaa aatcaactct acaacgaact taatctggga     1800
cgccgagagg agtacgatgt cttggataag agacgcggca gggaccctga atgggcgga     1860 aagccaagac ggaagaaccc ccaggaaggt ctgtacaatg aacttcagaa agataagatg     1920
gccgaagcct acagcgagat cggcatgaaa ggagagaggc gccgcggcaa agggcatgat     1980
ggactgtatc agggtctcag tactgctact aaggacacat atgatgccct ccacatgcag     2040
gccctgccac caaggtga                                                   2058

<210> SEQ ID NO 2
<211> LENGTH: 57
<212> TYPE: DNA
<213> ORGANISM: Artificial Sequence
<220> FEATURE:
<223> OTHER INFORMATION: IgG Signal peptide

<400> SEQUENCE: 2
atggagtttg ggctgagctg gcttttttctt gtggctattt taaaaggtgt ccagtgc       57

<210> SEQ ID NO 3
<211> LENGTH: 1416
<212> TYPE: DNA
<213> ORGANISM: Artificial Sequence
<220> FEATURE:
<223> OTHER INFORMATION: MuSK extracellular domain

<400> SEQUENCE: 3
cttccaaaag ctcctgtcat caccactcct cttgaaacag tggatgcctt agttgaagaa       60
gtggctactt tcatgtgtgc agtggaatcc taccccagc ctgagatttc ctggactaga      120
aataaaattc tcattaaact ctttgacacc cggtacagca tccggagaa tgggcagctc      180 ctcaccatcc tgagtgtgga agacagtgat gatggcattt actgctgcac ggccaacaat      240
ggtgtgggag gagctgtgga gagttgtgga gccctgcaag tgaagatgaa acctaaaata      300
actcgccctc ccataaatgt gaaaataata gagggattaa aagcagtcct accatgtact      360
acaatgggta atcccaaacc atcagtgtct tggataaagg agacagccc tctcagggaa      420 aattcccgaa ttgcagttct tgaatctggg agcttgagga ttcataacgt acaaaaggaa      480
gatgcaggac agtatcgatg tgtggcaaaa aacagcctcg ggacagcata ttccaaagtg      540
```

```
gtgaagctgg aagttgaggt ttttgccagg attctgcggg ctcctgaatc ccacaatgtc    600
acctttggct cctttgtgac cctgcactgt acagcaacag gcattcctgt ccccaccatc    660
acctggattg aaaacggaaa tgctgtttct tctgggtcca ttcaagagag tgtgaaagac    720
cgagtgattg actcaagact gcagctgttt atcaccaagc caggactcta cacatgcata    780
gctaccaata agcatgggga aagttcagt actgccaagg ctgcagccac catcagcata    840
gcagaatgga gtaaaccaca gaaagataac aaaggctact gcgcccagta cagaggggag    900
gtgtgtaatg cagtcctggc aaaagatgct cttgtttttc tcaacacctc ctatgcggac    960
cctgaggagg cccaagagct actggtccac acggcctgga tgaactgaa agtagtgagc   1020 ccagtctgcc ggccagctgc tgaggctttg ttgtgtaacc acatcttcca ggagtgcagt   1080
cctggagtag tgcctactcc tattcccatt tgcagagagt actgcttggc agtaaaggag   1140
ctcttctgcg caaaagaatg gctggtaatg aagagaaga cccacagagg actctacaga   1200
tccgagatgc atttgctgtc cgtgccagaa tgcagcaagc ttcccagcat gcattgggac   1260
cccacggcct gtgccagact gccacatcta gattataaca agaaaacct aaaaacattc   1320 ccaccaatga cgtcctcaaa gccaagtgtg gacattccaa atctgccttc ctcctcctct   1380
tcttccttct ctgtctcacc tacatactcc atgact                             1416

<210> SEQ ID NO 4
<211> LENGTH: 30
<212> TYPE: DNA
<213> ORGANISM: Artificial Sequence
<220> FEATURE:
<223> OTHER INFORMATION: GS Linker (codon optimized)

<400> SEQUENCE: 4
ggaggtggag gtagtggcgg tggaggcagc                                     30

<210> SEQ ID NO 5
<211> LENGTH: 72
<212> TYPE: DNA
<213> ORGANISM: Artificial Sequence
<220> FEATURE:
<223> OTHER INFORMATION: CD8 transmembrane domain (codon optimized)

<400> SEQUENCE: 5
atctacatct gggcacccct ggctggaaca tgcggggtcc tgctgctgag cttggtgatc     60 acccttact gc                                                         72

<210> SEQ ID NO 6
<211> LENGTH: 1416
<212> TYPE: DNA
<213> ORGANISM: Artificial Sequence
<220> FEATURE:
<223> OTHER INFORMATION: MuSK-I96A extracellular domain

<400> SEQUENCE: 6
cttccaaaag ctcctgtcat caccactcct cttgaaacag tggatgcctt agttgaagaa     60
gtggctactt tcatgtgtgc agtggaatcc tacccccagc tgagatttc ctggactaga    120 aataaaattc tcattaaact ctttgacacc cggtacagca tccggagaa tgggcagctc    180 ctcaccatcc tgagtgtgga agacagtgat gatggcgcat actgctgcac ggccaacaat    240
ggtgtgggag gagctgtgga gagttgtgga gccctgcaag tgaagatgaa acctaaaata    300
actcgccctc ccataaatgt gaaaataata gagggattaa agcagtcct accatgtact    360 acaatgggta atcccaaacc atcagtgtct tggataaagg gagacagccc tctcagggaa    420
```

```
aattcccgaa ttgcagttct tgaatctggg agcttgagga ttcataacgt acaaaaggaa      480
gatgcaggac agtatcgatg tgtggcaaaa acagcctcg ggacagcata ttccaaagtg       540
gtgaagctgg aagttgaggt ttttgccagg attctgcggg ctcctgaatc ccacaatgtc      600
acctttggct cctttgtgac cctgcactgt acagcaacag gcattcctgt ccccaccatc      660
acctggattg aaaacggaaa tgctgttcct tctgggtcca ttcaagagag tgtgaaagac      720
cgagtgattg actcaagact gcagctgttt atcaccaagc caggactcta cacatgcata      780
gctaccaata gcatgggga gaagttcagt actgccaagg ctgcagccac catcagcata      840
gcagaatgga gtaaaccaca gaaagataac aaaggctact gcgcccagta cagaggggag      900
gtgtgtaatg cagtcctggc aaaagatgct cttgtttttc tcaacaccct ctatgcggac      960
cctgaggagg cccaagagct actggtccac acggcctgga tgaactgaa agtagtgagc      1020 ccagtctgcc ggccagctgc tgaggctttg ttgtgtaacc acatcttcca ggagtgcagt     1080
cctggagtag tgcctactcc tattcccatt tgcagagagt actgcttggc agtaaaggag     1140
ctcttctgcg caaaagaatg gctggtaatg aagagaaga cccacagagg actctacaga     1200
tccgagatgc atttgctgtc cgtgccagaa tgcagcaagc ttcccagcat gcattgggac     1260
cccacggcct gtgccagact gccacatcta gattataaca agaaaacct aaaaacattc     1320 ccaccaatga cgtcctcaaa gccaagtgtg acattccaa atctgccttc ctcctcctct     1380
tcttccttct ctgtctcacc tacatactcc atgact                                1416

<210> SEQ ID NO 7
<211> LENGTH: 126
<212> TYPE: DNA
<213> ORGANISM: Artificial Sequence
<220> FEATURE:
<223> OTHER INFORMATION: 4-1BB intracellular domain (codon optimized)

<400> SEQUENCE: 7
aagcgcggtc gcaagaaact gctctatatt tttaaacagc cattcatgag acctgtccag       60
accactcaag aggaggacgg atgttcctgt agatttcctg aagaggaaga ggggggtgc      120 gagctg                                                                 126

<210> SEQ ID NO 8
<211> LENGTH: 336
<212> TYPE: DNA
<213> ORGANISM: Artificial Sequence
<220> FEATURE:
<223> OTHER INFORMATION: CD3zeta intracellular domain (codon optimized)

<400> SEQUENCE: 8
agagtaaagt tcagtaggtc cgccgatgcc ccagcctatc aacagggca aaatcaactc        60 tacaacgaac ttaatctggg acgccgagag gagtacgatg tcttggataa gacgcggc       120 agggaccctg aaatgggcgg aaagccaaga cggaagaacc cccaggaagg tctgtacaat     180
gaacttcaga agataagat ggccgaagcc tacagcgaga tcggcatgaa aggagagagg     240
cgccgcggca aagggcatga tggactgtat cagggtctca gtactgctac taaggacaca     300
tatgatgccc tccacatgca ggccctgcca ccaagg                                336

<210> SEQ ID NO 9
<211> LENGTH: 685
<212> TYPE: PRT
<213> ORGANISM: Artificial Sequence
<220> FEATURE:
```

<223> OTHER INFORMATION: pTRPE.MuSKWT.BBz CAAR

<400> SEQUENCE: 9

```
Met Glu Phe Gly Leu Ser Trp Leu Phe Leu Val Ala Ile Leu Lys Gly
1               5                   10                  15

Val Gln Cys Gly Ser Leu Pro Lys Ala Pro Val Ile Thr Thr Pro Leu
            20                  25                  30

Glu Thr Val Asp Ala Leu Val Glu Glu Val Ala Thr Phe Met Cys Ala
        35                  40                  45

Val Glu Ser Tyr Pro Gln Pro Glu Ile Ser Trp Thr Arg Asn Lys Ile
    50                  55                  60

Leu Ile Lys Leu Phe Asp Thr Arg Tyr Ser Ile Arg Glu Asn Gly Gln
65                  70                  75                  80

Leu Leu Thr Ile Leu Ser Val Glu Asp Ser Asp Asp Gly Ile Tyr Cys
                85                  90                  95

Cys Thr Ala Asn Asn Gly Val Gly Gly Ala Val Glu Ser Cys Gly Ala
            100                 105                 110

Leu Gln Val Lys Met Lys Pro Lys Ile Thr Arg Pro Pro Ile Asn Val
        115                 120                 125

Lys Ile Ile Glu Gly Leu Lys Ala Val Leu Pro Cys Thr Thr Met Gly
130                 135                 140

Asn Pro Lys Pro Ser Val Ser Trp Ile Lys Gly Asp Ser Pro Leu Arg
145                 150                 155                 160

Glu Asn Ser Arg Ile Ala Val Leu Glu Ser Gly Ser Leu Arg Ile His
                165                 170                 175

Asn Val Gln Lys Glu Asp Ala Gly Gln Tyr Arg Cys Val Ala Lys Asn
            180                 185                 190

Ser Leu Gly Thr Ala Tyr Ser Lys Val Val Lys Leu Glu Val Glu Val
        195                 200                 205

Phe Ala Arg Ile Leu Arg Ala Pro Glu Ser His Asn Val Thr Phe Gly
    210                 215                 220

Ser Phe Val Thr Leu His Cys Thr Ala Thr Gly Ile Pro Val Pro Thr
225                 230                 235                 240

Ile Thr Trp Ile Glu Asn Gly Asn Ala Val Ser Ser Gly Ser Ile Gln
                245                 250                 255

Glu Ser Val Lys Asp Arg Val Ile Asp Ser Arg Leu Gln Leu Phe Ile
            260                 265                 270

Thr Lys Pro Gly Leu Tyr Thr Cys Ile Ala Thr Asn Lys His Gly Glu
        275                 280                 285

Lys Phe Ser Thr Ala Lys Ala Ala Thr Ile Ser Ile Ala Glu Trp
    290                 295                 300

Ser Lys Pro Gln Lys Asp Asn Lys Gly Tyr Cys Ala Gln Tyr Arg Gly
305                 310                 315                 320

Glu Val Cys Asn Ala Val Leu Ala Lys Asp Ala Leu Val Phe Leu Asn
                325                 330                 335

Thr Ser Tyr Ala Asp Pro Glu Glu Ala Gln Glu Leu Leu Val His Thr
            340                 345                 350

Ala Trp Asn Glu Leu Lys Val Val Ser Pro Val Cys Arg Pro Ala Ala
        355                 360                 365

Glu Ala Leu Leu Cys Asn His Ile Phe Gln Glu Cys Ser Pro Gly Val
    370                 375                 380

Val Pro Thr Pro Ile Pro Ile Cys Arg Glu Tyr Cys Leu Ala Val Lys
385                 390                 395                 400
```

```
Glu Leu Phe Cys Ala Lys Glu Trp Leu Val Met Glu Lys Thr His
                405                 410                 415
Arg Gly Leu Tyr Arg Ser Glu Met His Leu Leu Ser Val Pro Glu Cys
            420                 425                 430
Ser Lys Leu Pro Ser Met His Trp Asp Pro Thr Ala Cys Ala Arg Leu
        435                 440                 445
Pro His Leu Asp Tyr Asn Lys Glu Asn Leu Lys Thr Phe Pro Pro Met
    450                 455                 460
Thr Ser Ser Lys Pro Ser Val Asp Ile Pro Asn Leu Pro Ser Ser Ser
465                 470                 475                 480
Ser Ser Ser Phe Ser Val Ser Pro Thr Tyr Ser Met Thr Ala Ser Gly
                485                 490                 495
Gly Gly Gly Ser Gly Gly Gly Ser Ser Gly Ile Tyr Ile Trp Ala
            500                 505                 510
Pro Leu Ala Gly Thr Cys Gly Val Leu Leu Leu Ser Leu Val Ile Thr
        515                 520                 525
Leu Tyr Cys Lys Arg Gly Arg Lys Lys Leu Leu Tyr Ile Phe Lys Gln
    530                 535                 540
Pro Phe Met Arg Pro Val Gln Thr Thr Gln Glu Glu Asp Gly Cys Ser
545                 550                 555                 560
Cys Arg Phe Pro Glu Glu Glu Gly Gly Cys Glu Leu Arg Val Lys
                565                 570                 575
Phe Ser Arg Ser Ala Asp Ala Pro Ala Tyr Gln Gln Gly Gln Asn Gln
            580                 585                 590
Leu Tyr Asn Glu Leu Asn Leu Gly Arg Arg Glu Glu Tyr Asp Val Leu
        595                 600                 605
Asp Lys Arg Arg Gly Arg Asp Pro Glu Met Gly Gly Lys Pro Arg Arg
    610                 615                 620
Lys Asn Pro Gln Glu Gly Leu Tyr Asn Glu Leu Gln Lys Asp Lys Met
625                 630                 635                 640
Ala Glu Ala Tyr Ser Glu Ile Gly Met Lys Gly Glu Arg Arg Arg Gly
                645                 650                 655
Lys Gly His Asp Gly Leu Tyr Gln Gly Leu Ser Thr Ala Thr Lys Asp
            660                 665                 670
Thr Tyr Asp Ala Leu His Met Gln Ala Leu Pro Pro Arg
        675                 680                 685

<210> SEQ ID NO 10
<211> LENGTH: 19
<212> TYPE: PRT
<213> ORGANISM: Artificial Sequence
<220> FEATURE:
<223> OTHER INFORMATION: IgG Signal peptide

<400> SEQUENCE: 10

Met Glu Phe Gly Leu Ser Trp Leu Phe Leu Val Ala Ile Leu Lys Gly
1               5                   10                  15

Val Gln Cys

<210> SEQ ID NO 11
<211> LENGTH: 472
<212> TYPE: PRT
<213> ORGANISM: Artificial Sequence
<220> FEATURE:
<223> OTHER INFORMATION: MuSK extracellular domain

<400> SEQUENCE: 11
```

```
Leu Pro Lys Ala Pro Val Ile Thr Thr Pro Leu Glu Thr Val Asp Ala
1               5                   10                  15

Leu Val Glu Glu Val Ala Thr Phe Met Cys Ala Val Glu Ser Tyr Pro
            20                  25                  30

Gln Pro Glu Ile Ser Trp Thr Arg Asn Lys Ile Leu Ile Lys Leu Phe
            35                  40                  45

Asp Thr Arg Tyr Ser Ile Arg Glu Asn Gly Gln Leu Leu Thr Ile Leu
        50                  55                  60

Ser Val Glu Asp Ser Asp Gly Ile Tyr Cys Cys Thr Ala Asn Asn
65                  70                  75                  80

Gly Val Gly Gly Ala Val Glu Ser Cys Gly Ala Leu Gln Val Lys Met
                85                  90                  95

Lys Pro Lys Ile Thr Arg Pro Ile Asn Val Lys Ile Ile Glu Gly
                100                 105                 110

Leu Lys Ala Val Leu Pro Cys Thr Thr Met Gly Asn Pro Lys Pro Ser
        115                 120                 125

Val Ser Trp Ile Lys Gly Asp Ser Pro Leu Arg Glu Asn Ser Arg Ile
        130                 135                 140

Ala Val Leu Glu Ser Gly Ser Leu Arg Ile His Asn Val Gln Lys Glu
145                 150                 155                 160

Asp Ala Gly Gln Tyr Arg Cys Val Ala Lys Asn Ser Leu Gly Thr Ala
                165                 170                 175

Tyr Ser Lys Val Val Lys Leu Glu Val Glu Val Phe Ala Arg Ile Leu
                180                 185                 190

Arg Ala Pro Glu Ser His Asn Val Thr Phe Gly Ser Phe Val Thr Leu
            195                 200                 205

His Cys Thr Ala Thr Gly Ile Pro Val Pro Thr Ile Thr Trp Ile Glu
    210                 215                 220

Asn Gly Asn Ala Val Ser Ser Gly Ser Ile Gln Glu Ser Val Lys Asp
225                 230                 235                 240

Arg Val Ile Asp Ser Arg Leu Gln Leu Phe Ile Thr Lys Pro Gly Leu
                245                 250                 255

Tyr Thr Cys Ile Ala Thr Asn Lys His Gly Glu Lys Phe Ser Thr Ala
            260                 265                 270

Lys Ala Ala Thr Ile Ser Ile Ala Glu Trp Ser Lys Pro Gln Lys
        275                 280                 285

Asp Asn Lys Gly Tyr Cys Ala Gln Tyr Arg Gly Glu Val Cys Asn Ala
        290                 295                 300

Val Leu Ala Lys Asp Ala Leu Val Phe Leu Asn Thr Ser Tyr Ala Asp
305                 310                 315                 320

Pro Glu Glu Ala Gln Glu Leu Leu Val His Thr Ala Trp Asn Glu Leu
                325                 330                 335

Lys Val Val Ser Pro Val Cys Arg Pro Ala Ala Glu Ala Leu Leu Cys
                340                 345                 350

Asn His Ile Phe Gln Glu Cys Ser Pro Gly Val Val Pro Thr Pro Ile
        355                 360                 365

Pro Ile Cys Arg Glu Tyr Cys Leu Ala Val Lys Glu Leu Phe Cys Ala
    370                 375                 380

Lys Glu Trp Leu Val Met Glu Glu Lys Thr His Arg Gly Leu Tyr Arg
385                 390                 395                 400

Ser Glu Met His Leu Leu Ser Val Pro Glu Cys Ser Lys Leu Pro Ser
                405                 410                 415

Met His Trp Asp Pro Thr Ala Cys Ala Arg Leu Pro His Leu Asp Tyr
```

```
                420             425             430
Asn Lys Glu Asn Leu Lys Thr Phe Pro Pro Met Thr Ser Ser Lys Pro
            435                 440                 445

Ser Val Asp Ile Pro Asn Leu Pro Ser Ser Ser Ser Ser Phe Ser
        450                 455                 460

Val Ser Pro Thr Tyr Ser Met Thr
465                 470

<210> SEQ ID NO 12
<211> LENGTH: 9
<212> TYPE: PRT
<213> ORGANISM: Artificial Sequence
<220> FEATURE:
<223> OTHER INFORMATION: GS Linker

<400> SEQUENCE: 12

Gly Gly Gly Ser Gly Gly Gly Gly Ser
1               5

<210> SEQ ID NO 13
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 13

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 14
<211> LENGTH: 42
<212> TYPE: PRT
<213> ORGANISM: Artificial Sequence
<220> FEATURE:
<223> OTHER INFORMATION: 4-1BB intracellular domain

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 15
<211> LENGTH: 112
<212> TYPE: PRT
<213> ORGANISM: Artificial Sequence
<220> FEATURE:
<223> OTHER INFORMATION: CD3zeta intracellular domain

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
```

```
         50                  55                  60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 16
<211> LENGTH: 2058
<212> TYPE: DNA
<213> ORGANISM: Artificial Sequence
<220> FEATURE:
<223> OTHER INFORMATION: pTRPE.MuSKWT.BBz CAAR

<400> SEQUENCE: 16

| | |
|---|---|
| atggagtttg ggctgagctg gcttttttctt gtggctattt taaaaggtgt ccagtgcgga | 60 |
| tcccttccaa aagctcctgt catcaccact cctcttgaaa cagtggatgc cttagtgaa | 120 |
| gaagtggcta ctttcatgtg tgcagtggaa tcctacccc agcctgagat tcctggact | 180 |
| agaaataaaa ttctcattaa actctttgac acccggtaca gcatccggga gaatgggcag | 240 |
| ctcctcacca tcctgagtgt ggaagacagt gatgatggca tttactgctg cacggccaac | 300 |
| aatggtgtgg gaggagctgt ggagagttgt ggagccctgc aagtgaagat gaaacctaaa | 360 |
| ataactcgcc ctcccataaa tgtgaaaata tagagggat taaaagcagt cctaccatgt | 420 |
| actacaatgg gtaatcccaa accatcagtg tcttggataa agggacagg ccctctcagg | 480 |
| gaaaattccc gaattgcagt tcttgaatct gggagcttga ggattcataa cgtacaaaag | 540 |
| gaagatgcag acagtatcg atgtgtggca aaaacagcc tcggacagc atattccaaa | 600 |
| gtggtgaagc tggaagttga ggttttgcc aggattctgc gggctcctga atcccacaat | 660 |
| gtcaccttg ctcctttgt gaccctgcac tgtacagcaa caggcattcc tgtccccacc | 720 |
| atcacctgga ttgaaaacgg aaatgctgtt tcttctgggt ccattcaaga gagtgtgaaa | 780 |
| gaccgagtga ttgactcaag actgcagctg tttatcacca gccaggact ctacacatgc | 840 |
| atagctacca taagcatgg ggagaagttc agtactgcca aggctgcagc caccatcagc | 900 |
| atagcagaat ggagtaaacc acagaaagat aacaaaggct actgcgccca gtacagaggg | 960 |
| gaggtgtgta atgcagtcct ggcaaaagat gctcttgttt ttctcaacac ctcctatgcg | 1020 |
| gaccctgagg aggcccaaga gctactggtc cacacggcct ggaatgaact gaaagtagtg | 1080 |
| agcccagtct gccggccagc tgctgaggct tgttgtgta accacatctt ccaggagtgc | 1140 |
| agtcctggag tagtgcctac tcctattccc atttgcagag agtactgctt ggcagtaaag | 1200 |
| gagctcttct gcgcaaaaga atggctggta atggaagaga gacccacag aggactctac | 1260 |
| agatccgaga tgcatttgct gtccgtgcca gaatgcagca agcttccag catgcattgg | 1320 |
| gaccccacgg cctgtgccag actgccacat ctagattata caaagaaaa cctaaaaaca | 1380 |
| ttcccaccaa tgacgtcctc aaagccaagt gtggacattc caaatctgcc ttcctcctcc | 1440 |
| tcttcttcct tctctgtctc acctacatac tccatgactg ctagcggtgg cggaggttct | 1500 |
| ggaggtggag gttcctccgg aatctacatc tgggcgccct tggccgggac ttgtggggtc | 1560 |
| cttctcctgt cactggttat caccctttac tgcaaacggg gcagaaagaa actcctgtat | 1620 |
| atattcaaac aaccatttat gagaccagta caaactactc aagaggaaga tggctgtagc | 1680 |
| tgccgatttc cagaagaaga agaaggagga tgtgaactga gagtgaagtt cagcaggagc | 1740 |

| | |
|---|---|
| gcagacgccc ccgcgtacca gcagggccag aaccagctct ataacgagct caatctagga | 1800 |
| cgaagagagg agtacgatgt tttggacaag agacgtggcc gggaccctga gatgggggga | 1860 |
| aagccgagaa ggaagaaccc tcaggaaggc ctgtacaatg aactgcagaa agataagatg | 1920 |
| gcggaggcct acagtgagat tgggatgaaa ggcgagcgcc ggaggggcaa ggggcacgat | 1980 |
| ggcctttacc agggtctcag tacagccacc aaggacacct acgacgccct tcacatgcag | 2040 |
| gccctgcccc ctcgctaa | 2058 |

```
<210> SEQ ID NO 17
<211> LENGTH: 30
<212> TYPE: DNA
<213> ORGANISM: Artificial Sequence
<220> FEATURE:
<223> OTHER INFORMATION: GS Linker

<400> SEQUENCE: 17
```

| | |
|---|---|
| ggtggcggag gttctggagg tggaggttcc | 30 |

```
<210> SEQ ID NO 18
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 18
```

| | |
|---|---|
| atctacatct gggcgccctt ggccgggact tgtggggtcc ttctcctgtc actggttatc | 60 |
| accctttact gc | 72 |

```
<210> SEQ ID NO 19
<211> LENGTH: 126
<212> TYPE: DNA
<213> ORGANISM: Artificial Sequence
<220> FEATURE:
<223> OTHER INFORMATION: 4-1BB intracellular domain

<400> SEQUENCE: 19
```

| | |
|---|---|
| aaacggggca gaaagaaact cctgtatata ttcaaacaac catttatgag accagtacaa | 60 |
| actactcaag aggaagatgg ctgtagctgc cgatttccag aagaagaaga aggaggatgt | 120 |
| gaactg | 126 |

```
<210> SEQ ID NO 20
<211> LENGTH: 336
<212> TYPE: DNA
<213> ORGANISM: Artificial Sequence
<220> FEATURE:
<223> OTHER INFORMATION: CD3zeta intracellular domain

<400> SEQUENCE: 20
```

| | |
|---|---|
| agagtgaagt tcagcaggag cgcagacgcc ccgcgtacc agcagggcca gaaccagctc | 60 |
| tataacgagc tcaatctagg acgaagagag gagtacgatg ttttggacaa gagacgtggc | 120 |
| cgggaccctg agatgggggg aaagccgaga aggaagaacc ctcaggaagg cctgtacaat | 180 |
| gaactgcaga aagataagat ggcggaggcc tacagtgaga ttgggatgaa aggcgagcgc | 240 |
| cggagggggca aggggcacga tggcctttac cagggtctca gtacagccac caaggacacc | 300 |
| tacgacgccc ttcacatgca ggccctgccc cctcgc | 336 |

```
<210> SEQ ID NO 21
<211> LENGTH: 2058
```

<212> TYPE: DNA
<213> ORGANISM: Artificial Sequence
<220> FEATURE:
<223> OTHER INFORMATION: pTRPE.MuSKI96A.BBz CAAR

<400> SEQUENCE: 21

| | | | | | |
|---|---|---|---|---|---|
| atggagtttg | ggctgagctg | gcttttctt | gtggctattt | taaaaggtgt | ccagtgcgga | 60 |
| tcccttccaa | aagctcctgt | catcaccact | cctcttgaaa | cagtggatgc | cttagttgaa | 120 |
| gaagtggcta | ctttcatgtg | tgcagtggaa | tcctaccccc | agcctgagat | ttcctggact | 180 |
| agaaataaaa | ttctcattaa | actctttgac | acccggtaca | gcatccggga | gaatgggcag | 240 |
| ctcctcacca | tcctgagtgt | ggaagacagt | gatgatggcg | catactgctg | cacggccaac | 300 |
| aatggtgtgg | gaggagctgt | ggagagttgt | ggagccctgc | aagtgaagat | gaaacctaaa | 360 |
| ataactcgcc | ctcccataaa | tgtgaaaata | atagagggat | taaaagcagt | cctaccatgt | 420 |
| actacaatgg | gtaatcccaa | accatcagtg | tcttggataa | agggagacag | ccctctcagg | 480 |
| gaaaattccc | gaattgcagt | tcttgaatct | gggagcttga | ggattcataa | cgtacaaaag | 540 |
| gaagatgcag | acagtatcg | atgtgtggca | aaaaacagcc | tcggacagc | atattccaaa | 600 |
| gtggtgaagc | tggaagttga | ggtttttgcc | aggattctgc | gggctcctga | atcccacaat | 660 |
| gtcacctttg | gctcctttgt | gaccctgcac | tgtacagcaa | caggcattcc | tgtccccacc | 720 |
| atcacctgga | ttgaaaacgg | aaatgctgtt | tcttctgggt | ccattcaaga | gagtgtgaaa | 780 |
| gaccgagtga | ttgactcaag | actgcagctg | tttatcacca | agccaggact | ctacacatgc | 840 |
| atagctacca | ataagcatgg | ggagaagttc | agtactgcca | aggctgcagc | caccatcagc | 900 |
| atagcagaat | ggagtaaacc | acagaaagat | aacaaaggct | actgcgccca | gtacagaggg | 960 |
| gaggtgtgta | atgcagtcct | ggcaaaagat | gctcttgttt | ttctcaacac | ctccatgcg | 1020 |
| gaccctgagg | aggcccaaga | gctactggtc | cacacggcct | ggaatgaact | gaaagtagtg | 1080 |
| agcccagtct | gccggccagc | tgctgaggct | ttgttgtgta | accacatctt | ccaggagtgc | 1140 |
| agtcctggag | tagtgcctac | tcctattccc | atttgcagag | agtactgctt | ggcagtaaag | 1200 |
| gagctcttct | gcgcaaaaga | atggctggta | atggaagaga | agaccacag | aggactctac | 1260 |
| agatccgaga | tgcatttgct | gtccgtgcca | gaatgcagca | agcttcccag | catgcattgg | 1320 |
| gaccccacgg | cctgtgccag | actgccacat | ctagattata | caaagaaaa | cctaaaaaca | 1380 |
| ttcccaccaa | tgacgtcctc | aaagccaagt | gtggacattc | caaatctgcc | ttcctcctcc | 1440 |
| tcttcttcct | tctctgtctc | acctacatac | tccatgactg | ctagcggagg | tggaggtagt | 1500 |
| ggcggtggag | gcagctctgg | tatctacatc | tgggcaccct | tggctggaac | atgcggggtc | 1560 |
| ctgctgctga | gcttggtgat | cacccttac | tgcaagcgcg | gtcgcaagaa | actgctctat | 1620 |
| attttaaac | agccattcat | gagacctgtc | cagaccactc | aagaggagga | cggatgttcc | 1680 |
| tgtagatttc | ctgaagagga | agagggggg | tgcgagctga | gagtaaagtt | cagtaggtcc | 1740 |
| gccgatgccc | cagcctatca | acaggggcaa | aatcaactct | acaacgaact | taatctggga | 1800 |
| cgccgagagg | agtacgatgt | cttggataag | agacgcggca | gggaccctga | aatgggcgga | 1860 |
| aagccaagac | ggaagaaccc | ccaggaaggt | ctgtacaatg | aacttcagaa | agataagatg | 1920 |
| gccgaagcct | acagcgagat | cggcatgaaa | ggagagaggc | gccgcggcaa | agggcatgat | 1980 |
| ggactgtatc | agggtctcag | tactgctact | aaggacacat | atgatgccct | ccacatgcag | 2040 |
| gcccctgccac | caaggtga | | | | | 2058 |

<210> SEQ ID NO 22

<211> LENGTH: 685
<212> TYPE: PRT
<213> ORGANISM: Artificial Sequence
<220> FEATURE:
<223> OTHER INFORMATION: pTRPE.MuSKI96A.BBz CAAR

<400> SEQUENCE: 22

```
Met Glu Phe Gly Leu Ser Trp Leu Phe Leu Val Ala Ile Leu Lys Gly
1               5                   10                  15

Val Gln Cys Gly Ser Leu Pro Lys Ala Pro Val Ile Thr Thr Pro Leu
            20                  25                  30

Glu Thr Val Asp Ala Leu Val Glu Glu Val Ala Thr Phe Met Cys Ala
        35                  40                  45

Val Glu Ser Tyr Pro Gln Pro Glu Ile Ser Trp Thr Arg Asn Lys Ile
    50                  55                  60

Leu Ile Lys Leu Phe Asp Thr Arg Tyr Ser Ile Arg Glu Asn Gly Gln
65                  70                  75                  80

Leu Leu Thr Ile Leu Ser Val Glu Asp Ser Asp Gly Ala Tyr Cys
                85                  90                  95

Cys Thr Ala Asn Asn Gly Val Gly Gly Ala Val Glu Ser Cys Gly Ala
            100                 105                 110

Leu Gln Val Lys Met Lys Pro Lys Ile Thr Arg Pro Pro Ile Asn Val
        115                 120                 125

Lys Ile Ile Glu Gly Leu Lys Ala Val Leu Pro Cys Thr Thr Met Gly
130                 135                 140

Asn Pro Lys Pro Ser Val Ser Trp Ile Lys Gly Asp Ser Pro Leu Arg
145                 150                 155                 160

Glu Asn Ser Arg Ile Ala Val Leu Glu Ser Gly Ser Leu Arg Ile His
                165                 170                 175

Asn Val Gln Lys Glu Asp Ala Gly Gln Tyr Arg Cys Val Ala Lys Asn
            180                 185                 190

Ser Leu Gly Thr Ala Tyr Ser Lys Val Val Lys Leu Glu Val Glu Val
        195                 200                 205

Phe Ala Arg Ile Leu Arg Ala Pro Glu Ser His Asn Val Thr Phe Gly
    210                 215                 220

Ser Phe Val Thr Leu His Cys Thr Ala Thr Gly Ile Pro Val Pro Thr
225                 230                 235                 240

Ile Thr Trp Ile Glu Asn Gly Asn Ala Val Ser Ser Gly Ser Ile Gln
                245                 250                 255

Glu Ser Val Lys Asp Arg Val Ile Asp Ser Arg Leu Gln Leu Phe Ile
            260                 265                 270

Thr Lys Pro Gly Leu Tyr Thr Cys Ile Ala Thr Asn Lys His Gly Glu
        275                 280                 285

Lys Phe Ser Thr Ala Lys Ala Ala Thr Ile Ser Ile Ala Glu Trp
    290                 295                 300

Ser Lys Pro Gln Lys Asp Asn Lys Gly Tyr Cys Ala Gln Tyr Arg Gly
305                 310                 315                 320

Glu Val Cys Asn Ala Val Leu Ala Lys Asp Ala Leu Val Phe Leu Asn
                325                 330                 335

Thr Ser Tyr Ala Asp Pro Glu Asp Ala Gln Glu Leu Leu Val His Thr
            340                 345                 350

Ala Trp Asn Glu Leu Lys Val Val Ser Pro Val Cys Arg Pro Ala Ala
        355                 360                 365

Glu Ala Leu Leu Cys Asn His Ile Phe Gln Glu Cys Ser Pro Gly Val
    370                 375                 380
```

```
Val Pro Thr Pro Ile Pro Ile Cys Arg Glu Tyr Cys Leu Ala Val Lys
385                 390                 395                 400

Glu Leu Phe Cys Ala Lys Glu Trp Leu Val Met Glu Glu Lys Thr His
            405                 410                 415

Arg Gly Leu Tyr Arg Ser Glu Met His Leu Leu Ser Val Pro Glu Cys
        420                 425                 430

Ser Lys Leu Pro Ser Met His Trp Asp Pro Thr Ala Cys Ala Arg Leu
    435                 440                 445

Pro His Leu Asp Tyr Asn Lys Glu Asn Leu Lys Thr Phe Pro Pro Met
450                 455                 460

Thr Ser Ser Lys Pro Ser Val Asp Ile Pro Asn Leu Pro Ser Ser Ser
465                 470                 475                 480

Ser Ser Ser Phe Ser Val Ser Pro Thr Tyr Ser Met Thr Ala Ser Gly
            485                 490                 495

Gly Gly Gly Ser Gly Gly Gly Ser Ser Gly Ile Tyr Ile Trp Ala
        500                 505                 510

Pro Leu Ala Gly Thr Cys Gly Val Leu Leu Leu Ser Leu Val Ile Thr
    515                 520                 525

Leu Tyr Cys Lys Arg Gly Arg Lys Lys Leu Leu Tyr Ile Phe Lys Gln
530                 535                 540

Pro Phe Met Arg Pro Val Gln Thr Thr Gln Glu Glu Asp Gly Cys Ser
545                 550                 555                 560

Cys Arg Phe Pro Glu Glu Glu Gly Gly Cys Glu Leu Arg Val Lys
            565                 570                 575

Phe Ser Arg Ser Ala Asp Ala Pro Ala Tyr Gln Gln Gly Gln Asn Gln
        580                 585                 590

Leu Tyr Asn Glu Leu Asn Leu Gly Arg Arg Glu Glu Tyr Asp Val Leu
    595                 600                 605

Asp Lys Arg Arg Gly Arg Asp Pro Glu Met Gly Gly Lys Pro Arg Arg
610                 615                 620

Lys Asn Pro Gln Glu Gly Leu Tyr Asn Glu Leu Gln Lys Asp Lys Met
625                 630                 635                 640

Ala Glu Ala Tyr Ser Glu Ile Gly Met Lys Gly Glu Arg Arg Arg Gly
            645                 650                 655

Lys Gly His Asp Gly Leu Tyr Gln Gly Leu Ser Thr Ala Thr Lys Asp
        660                 665                 670

Thr Tyr Asp Ala Leu His Met Gln Ala Leu Pro Pro Arg
    675                 680                 685

<210> SEQ ID NO 23
<211> LENGTH: 472
<212> TYPE: PRT
<213> ORGANISM: Artificial Sequence
<220> FEATURE:
<223> OTHER INFORMATION: MuSK-I96A extracellular domain

<400> SEQUENCE: 23

Leu Pro Lys Ala Pro Val Ile Thr Thr Pro Leu Glu Thr Val Asp Ala
1               5                   10                  15

Leu Val Glu Glu Val Ala Thr Phe Met Cys Ala Val Glu Ser Tyr Pro
            20                  25                  30

Gln Pro Glu Ile Ser Trp Thr Arg Asn Lys Ile Leu Ile Lys Leu Phe
        35                  40                  45

Asp Thr Arg Tyr Ser Ile Arg Glu Asn Gly Gln Leu Leu Thr Ile Leu
    50                  55                  60
```

-continued

```
Ser Val Glu Asp Ser Asp Gly Ala Tyr Cys Cys Thr Ala Asn Asn
 65                  70                  75                  80

Gly Val Gly Gly Ala Val Glu Ser Cys Gly Ala Leu Gln Val Lys Met
                 85                  90                  95

Lys Pro Lys Ile Thr Arg Pro Pro Ile Asn Val Lys Ile Ile Glu Gly
                100                 105                 110

Leu Lys Ala Val Leu Pro Cys Thr Thr Met Gly Asn Pro Lys Pro Ser
                115                 120                 125

Val Ser Trp Ile Lys Gly Asp Ser Pro Leu Arg Glu Asn Ser Arg Ile
130                 135                 140

Ala Val Leu Glu Ser Gly Ser Leu Arg Ile His Asn Val Gln Lys Glu
145                 150                 155                 160

Asp Ala Gly Gln Tyr Arg Cys Val Ala Lys Asn Ser Leu Gly Thr Ala
                165                 170                 175

Tyr Ser Lys Val Val Lys Leu Glu Val Glu Val Phe Ala Arg Ile Leu
                180                 185                 190

Arg Ala Pro Glu Ser His Asn Val Thr Phe Gly Ser Phe Val Thr Leu
                195                 200                 205

His Cys Thr Ala Thr Gly Ile Pro Val Pro Thr Ile Thr Trp Ile Glu
210                 215                 220

Asn Gly Asn Ala Val Ser Ser Gly Ser Ile Gln Glu Ser Val Lys Asp
225                 230                 235                 240

Arg Val Ile Asp Ser Arg Leu Gln Leu Phe Ile Thr Lys Pro Gly Leu
                245                 250                 255

Tyr Thr Cys Ile Ala Thr Asn Lys His Gly Glu Lys Phe Ser Thr Ala
                260                 265                 270

Lys Ala Ala Thr Ile Ser Ile Ala Glu Trp Ser Lys Pro Gln Lys
                275                 280                 285

Asp Asn Lys Gly Tyr Cys Ala Gln Tyr Arg Gly Glu Val Cys Asn Ala
                290                 295                 300

Val Leu Ala Lys Asp Ala Leu Val Phe Leu Asn Thr Ser Tyr Ala Asp
305                 310                 315                 320

Pro Glu Glu Ala Gln Glu Leu Leu Val His Thr Ala Trp Asn Glu Leu
                325                 330                 335

Lys Val Val Ser Pro Val Cys Arg Pro Ala Ala Glu Ala Leu Leu Cys
                340                 345                 350

Asn His Ile Phe Gln Glu Cys Ser Pro Gly Val Val Pro Thr Pro Ile
                355                 360                 365

Pro Ile Cys Arg Glu Tyr Cys Leu Ala Val Lys Glu Leu Phe Cys Ala
                370                 375                 380

Lys Glu Trp Leu Val Met Glu Glu Lys Thr His Arg Gly Leu Tyr Arg
385                 390                 395                 400

Ser Glu Met His Leu Leu Ser Val Pro Glu Cys Ser Lys Leu Pro Ser
                405                 410                 415

Met His Trp Asp Pro Thr Ala Cys Ala Arg Leu Pro His Leu Asp Tyr
                420                 425                 430

Asn Lys Glu Asn Leu Lys Thr Phe Pro Pro Met Thr Ser Ser Lys Pro
                435                 440                 445

Ser Val Asp Ile Pro Asn Leu Pro Ser Ser Ser Ser Ser Phe Ser
                450                 455                 460

Val Ser Pro Thr Tyr Ser Met Thr
465                 470
```

<210> SEQ ID NO 24
<211> LENGTH: 2058
<212> TYPE: DNA
<213> ORGANISM: Artificial Sequence
<220> FEATURE:
<223> OTHER INFORMATION: pTRPE.MuSKI96A.BBz CAAR

<400> SEQUENCE: 24

| | |
|---|---|
| atggagtttg ggctgagctg gcttttctt gtggctattt taaaaggtgt ccagtgcgga | 60 |
| tcccttccaa aagctcctgt catcaccact cctcttgaaa cagtggatgc cttagttgaa | 120 |
| gaagtggcta cttttcatgtg tgcagtggaa tcctaccccc agcctgagat ttcctggact | 180 |
| agaaataaaa ttctcattaa actctttgac acccggtaca gcatccggga gaatgggcag | 240 |
| ctcctcacca tcctgagtgt ggaagacagt gatgatggcg catactgctg cacggccaac | 300 |
| aatggtgtgg gaggagctgt ggagagttgt ggagccctgc aagtgaagat gaaacctaaa | 360 |
| ataactcgcc ctcccataaa tgtgaaaata atagagggat taaaagcagt cctaccatgt | 420 |
| actacaatgg gtaatcccaa accatcagtg tcttggataa agggagacag ccctctcagg | 480 |
| gaaaattccc gaattgcagt tcttgaatct gggagcttga ggattcataa cgtacaaaag | 540 |
| gaagatgcag acagtatcg atgtgtggca aaaaacagcc tcgggacagc atattccaaa | 600 |
| gtggtgaagc tggaagttga ggttttgcc aggattctgc gggctcctga atcccacaat | 660 |
| gtcacctttg ctcctttgt gaccctgcac tgtacagcaa caggcattcc tgtccccacc | 720 |
| atcacctgga ttgaaaacgg aaatgctgtt tcttctgggt ccattcaaga gagtgtgaaa | 780 |
| gaccgagtga ttgactcaag actgcagctg tttatcacca gccaggact ctacacatgc | 840 |
| atagctacca ataagcatgg ggagaagttc agtactgcca aggctgcagc caccatcagc | 900 |
| atagcagaat ggagtaaacc acagaaagat aacaaaggct actgcgccca gtacagaggg | 960 |
| gaggtgtgta atgcagtcct ggcaaagat gctcttgttt ttctcaacac ctcctatgcg | 1020 |
| gaccctgagg aggcccaaga gctactggtc cacacggcct ggaatgaact gaaagtagtg | 1080 |
| agcccagtct gccggccagc tgctgaggct ttgttgtgta ccacatctt ccaggagtgc | 1140 |
| agtcctggag tagtgcctac tcctattccc atttgcagag agtactgctt ggcagtaaag | 1200 |
| gagctcttct gcgcaaaaga atggctggta atggaagaga gacccacag aggactctac | 1260 |
| agatccgaga tgcatttgct gtccgtgcca gaatgcagca agcttcccag catgcattgg | 1320 |
| gaccccacgg cctgtgccag actgccacat ctagattata caaagaaaaa cctaaaaaca | 1380 |
| ttcccaccaa tgacgtcctc aaagccaagt gtggacattc caaatctgcc ttcctcctcc | 1440 |
| tcttcttcct tctctgtctc acctacatac tccatgactg ctagcggtgg cggaggttct | 1500 |
| ggaggtggag gttcctccgg aatctacatc tgggcgccct tggccgggac ttgtggggtc | 1560 |
| cttctcctgt cactggttat caccctttac tgcaaacggg gcagaaagaa actcctgtat | 1620 |
| atattcaaac aaccatttat gagaccagta caaactactc aagaggaaga tggctgtagc | 1680 |
| tgccgatttc cagaagaaga agaaggagga tgtgaactga gagtgaagtt cagcaggagc | 1740 |
| gcagacgccc ccgcgtacca gcagggccag aaccagctct ataacgagct caatctagga | 1800 |
| cgaagagagg agtacgatgt tttggacaag acagtggcc gggaccctga gatggggga | 1860 |
| aagccgagaa ggaagaaccc tcaggaaggc ctgtacaatg aactgcagaa agataagatg | 1920 |
| gcggaggcct acagtgagat tgggatgaaa ggcgagcgcc ggaggggcaa ggggcacgat | 1980 |
| ggcctttacc agggtctcag tacagccacc aaggacacct cgacgccct tcacatgcag | 2040 |
| gccctgcccc ctcgctaa | 2058 |

<210> SEQ ID NO 25
<211> LENGTH: 2052
<212> TYPE: DNA
<213> ORGANISM: Artificial Sequence
<220> FEATURE:
<223> OTHER INFORMATION: pTRPE.MuSKWT_opt.BBz CAAR

<400> SEQUENCE: 25

| | | | | | |
|---|---|---|---|---|---|
| atggagtttg | ggctgagctg | gcttttctt | gtggctattt | taaaaggtgt | ccagtgcgga | 60 |
| tcccttccta | aagccccggt | aattaccacc | ccattggaga | ccgtcgatgc | ccttgtagag | 120 |
| gaggttgcaa | cctttatgtg | tgctgtagag | tcttacccgc | aaccagagat | atcatggacc | 180 |
| cgaaacaaga | tttttgatcaa | gttgttcgat | actcgatact | ccattcgaga | gaacgggcag | 240 |
| ctcctcacta | tattgagcgt | agaagacagt | gatgacggta | tatactgctg | caccgctaac | 300 |
| aatggtgtgg | gaggagcagt | ggaaagttgt | ggcgcacttc | aagtaaaaat | gaagccgaaa | 360 |
| attacgagac | ctccgattaa | cgttaaaatt | atagaggggc | tgaaagctgt | cctgccatgt | 420 |
| accacaatgg | gtaatcccaa | gcccagcgta | tcctggatca | aaggtgattc | accgttgaga | 480 |
| gaaaattcta | ggatagcggt | attggagtcc | ggctcactta | gaattcacaa | cgtccaaaaa | 540 |
| gaagatgctg | gtcagtacag | atgtgtcgcc | aaaaattctc | tcggaactgc | atacagtaaa | 600 |
| gtggtaaagc | ttgaagttga | agtgtttgca | aggattctgc | gagccccgga | gtcacacaat | 660 |
| gtaaccttcg | gttctttgt | gactcttcat | tgtaccgcta | ctggaatccc | agttcccacg | 720 |
| attacgtgga | ttgaaaacgg | aaatgccgtc | tcaagcggca | gcatacagga | gtccgtgaag | 780 |
| gatagagtca | tagactcccg | attgcaactg | ttcattacaa | agcctggcct | ttatacatgc | 840 |
| attgctacaa | acaagcatgg | tgagaaattc | agtacagcta | aggccgccgc | aacaatttcc | 900 |
| attgcagagt | ggagcaagcc | acaaaaagat | aacaagggtt | actgtgccca | atatcgaggg | 960 |
| gaagtttgta | acgctgtact | tgctaaggac | gctctcgtct | tcttgaatac | atcctacgcg | 1020 |
| gacccggagg | aagcccagga | gctcttggtg | cacactgcat | ggaatgaact | taaagtagtg | 1080 |
| tcccctgtat | gccggccagc | cgcggaagcg | ttgctctgta | atcacatttt | ccaagaatgt | 1140 |
| tcaccagggg | tagtaccaac | gcctatcccg | atatgtcggg | aatattgtct | ggcggtcaaa | 1200 |
| gagctctttt | gtgctaaaga | atggctcgtg | atggaggaaa | aaactcatcg | gggtttgtat | 1260 |
| cgctcagaaa | tgcacctgct | gagtgtccca | gaatgctcca | gttgcccag | tatgcactgg | 1320 |
| gaccctacgg | cgtgcgcacg | cttgcctcac | ctggactaca | taaagaaaa | tctgaaaaca | 1380 |
| tttcccccta | tgactagcag | taagccttct | gttgatattc | caaacctccc | gtcatcctct | 1440 |
| tcatcttctt | tctctgtcag | cccgacttat | ccatgactg | gtggcggagg | ttctggaggt | 1500 |
| ggaggttcct | ccggaatcta | catctgggcg | cccttggccg | ggacttgtgg | ggtccttctc | 1560 |
| ctgtcactgg | ttatcaccct | ttactgcaaa | cggggcagaa | agaaactcct | gtatatattc | 1620 |
| aaacaaccat | ttatgagacc | agtacaaact | actcaagagg | aagatggctg | tagctgccga | 1680 |
| tttccagaag | aagaagaagg | aggatgtgaa | ctgagagtga | agttcagcag | gagcgcagac | 1740 |
| gcccccgcgt | accagcaggg | ccagaaccag | ctctataacg | agctcaatct | aggacgaaga | 1800 |
| gaggagtacg | atgttttgga | caagagacgt | ggccgggacc | ctgagatggg | gggaaagccg | 1860 |
| agaaggaaga | accctcagga | aggcctgtac | aatgaactgc | agaaagataa | gatggcggag | 1920 |
| gcctacagtg | agattgggat | gaaaggcgag | cgccggaggg | gcaaggggca | cgatggcctt | 1980 |
| taccagggtc | tcagtacagc | caccaaggac | acctacgacg | cccttcacat | gcaggccctg | 2040 | cccctcgct aa                                                       2052

<210> SEQ ID NO 26
<211> LENGTH: 1416
<212> TYPE: DNA
<213> ORGANISM: Artificial Sequence
<220> FEATURE:
<223> OTHER INFORMATION: MuSK extracellular domain (codon optimized)

<400> SEQUENCE: 26

```
cttcctaaag ccccggtaat taccaccca ttggagaccg tcgatgccct gtagaggag      60
gttgcaacct ttatgtgtgc tgtagagtct tacccgcaac cagagatatc atggacccga   120
aacaagattt tgatcaagtt gttcgatact cgatactcca ttcgagagaa cgggcagctc   180
ctcactatat tgagcgtaga agacagtgat gacggtatat actgctgcac cgctaacaat   240
ggtgtgggag gagcagtgga aagttgtggc gcacttcaag taaaaatgaa gccgaaaatt   300
acgagaccct cgattaacgt taaaattata gaggggctga agctgtcct gccatgtacc   360
acaatgggta atcccaagcc cagcgtatcc tggatcaaag tgattcacc gttgagagaa   420
aattctagga tagcggtatt ggagtccggc tcacttagaa ttcacaacgt ccaaaaagaa   480
gatgctggtc agtacagatg tgtcgccaaa aattctctcg gaactgcata cagtaaagtg   540
gtaaagcttg aagttgaagt gtttgcaagg attctgcgag ccccggagtc acacaatgta   600
accttcggtt cttttgtgac tcttcattgt accgctactg gaatcccagt ccccacgatt   660
acgtggattg aaaacggaaa tgccgtctca gcggcagca tacaggagtc cgtgaaggat   720
agagtccatag actcccgatt gcaactgttc attacaaagc ctggccttta tacatgcatt   780
gctacaaaca agcatggtga gaaattcagt acagctaagg ccgccgcaac aatttccatt   840
gcagagtgga gcaagccaca aaagataac aagggttact gtgccaata tcgaggggaa   900
gtttgtaacg ctgtacttgc taaggacgct ctcgtcttct tgaatacatc ctacgcggac   960
ccggaggaag cccaggagct cttggtgcac actgcatgga atgaacttaa agtagtgtcc  1020
cctgtatgcc ggccagccgc ggaagcgttg ctctgtaatc acattttcca gaatgttca   1080
ccaggggtag taccaacgcc tatcccgata tgtcgggaat attgtctggc ggtcaaagag  1140
ctcttttgtg ctaaagaatg gctcgtgatg gaggaaaaaa ctcatcgggg tttgtatcgc  1200
tcagaaatgc acctgctgag tgtcccagaa tgctccaagt tgcccagtat gcactgggac  1260
cctacggcgt gcgcacgctt gcctcacctg gactacaata aagaaaatct gaaaacattt  1320
ccccctatga ctagcagtaa gccttctgtt gatattccaa acctcccgtc atcctcttca  1380
tcttctttct ctgtcagccc gacttattcc atgact                            1416
```

<210> SEQ ID NO 27
<211> LENGTH: 683
<212> TYPE: PRT
<213> ORGANISM: Artificial Sequence
<220> FEATURE:
<223> OTHER INFORMATION: pTRPE.MuSKWT_opt.BBz CAAR

<400> SEQUENCE: 27

Met Glu Phe Gly Leu Ser Trp Leu Phe Leu Val Ala Ile Leu Lys Gly
1               5                   10                  15

Val Gln Cys Gly Ser Leu Pro Lys Ala Pro Val Ile Thr Thr Pro Leu
            20                  25                  30

Glu Thr Val Asp Ala Leu Val Glu Glu Val Ala Thr Phe Met Cys Ala
        35                  40                  45

```
Val Glu Ser Tyr Pro Gln Pro Glu Ile Ser Trp Thr Arg Asn Lys Ile
 50                  55                  60

Leu Ile Lys Leu Phe Asp Thr Arg Tyr Ser Ile Arg Glu Asn Gly Gln
 65                  70                  75                  80

Leu Leu Thr Ile Leu Ser Val Glu Asp Ser Asp Gly Ile Tyr Cys
                 85                  90                  95

Cys Thr Ala Asn Asn Gly Val Gly Gly Ala Val Glu Ser Cys Gly Ala
                100                 105                 110

Leu Gln Val Lys Met Lys Pro Lys Ile Thr Arg Pro Pro Ile Asn Val
                115                 120                 125

Lys Ile Ile Glu Gly Leu Lys Ala Val Leu Pro Cys Thr Thr Met Gly
130                 135                 140

Asn Pro Lys Pro Ser Val Ser Trp Ile Lys Gly Asp Ser Pro Leu Arg
145                 150                 155                 160

Glu Asn Ser Arg Ile Ala Val Leu Glu Ser Gly Ser Leu Arg Ile His
                165                 170                 175

Asn Val Gln Lys Glu Asp Ala Gly Gln Tyr Arg Cys Val Ala Lys Asn
                180                 185                 190

Ser Leu Gly Thr Ala Tyr Ser Lys Val Val Lys Leu Glu Val Glu Val
                195                 200                 205

Phe Ala Arg Ile Leu Arg Ala Pro Glu Ser His Asn Val Thr Phe Gly
210                 215                 220

Ser Phe Val Thr Leu His Cys Thr Ala Thr Gly Ile Pro Val Pro Thr
225                 230                 235                 240

Ile Thr Trp Ile Glu Asn Gly Asn Ala Val Ser Ser Gly Ser Ile Gln
                245                 250                 255

Glu Ser Val Lys Asp Arg Val Ile Asp Ser Arg Leu Gln Leu Phe Ile
                260                 265                 270

Thr Lys Pro Gly Leu Tyr Thr Cys Ile Ala Thr Asn Lys His Gly Glu
                275                 280                 285

Lys Phe Ser Thr Ala Lys Ala Ala Thr Ile Ser Ile Ala Glu Trp
290                 295                 300

Ser Lys Pro Gln Lys Asp Asn Lys Gly Tyr Cys Ala Gln Tyr Arg Gly
305                 310                 315                 320

Glu Val Cys Asn Ala Val Leu Ala Lys Asp Ala Leu Val Phe Leu Asn
                325                 330                 335

Thr Ser Tyr Ala Asp Pro Glu Glu Ala Gln Glu Leu Leu Val His Thr
                340                 345                 350

Ala Trp Asn Glu Leu Lys Val Val Ser Pro Val Cys Arg Pro Ala Ala
                355                 360                 365

Glu Ala Leu Leu Cys Asn His Ile Phe Gln Glu Cys Ser Pro Gly Val
                370                 375                 380

Val Pro Thr Pro Ile Pro Ile Cys Arg Glu Tyr Cys Leu Ala Val Lys
385                 390                 395                 400

Glu Leu Phe Cys Ala Lys Glu Trp Leu Val Met Glu Glu Lys Thr His
                405                 410                 415

Arg Gly Leu Tyr Arg Ser Glu Met His Leu Leu Ser Val Pro Glu Cys
                420                 425                 430

Ser Lys Leu Pro Ser Met His Trp Asp Pro Thr Ala Cys Ala Arg Leu
                435                 440                 445

Pro His Leu Asp Tyr Asn Lys Glu Asn Leu Lys Thr Phe Pro Pro Met
450                 455                 460

Thr Ser Ser Lys Pro Ser Val Asp Ile Pro Asn Leu Pro Ser Ser Ser
```

```
                465                 470                 475                 480
        Ser Ser Ser Phe Ser Val Ser Pro Thr Tyr Ser Met Thr Gly Gly Gly
                        485                 490                 495

Gly Ser Gly Gly Gly Gly Ser Ser Gly Ile Tyr Ile Trp Ala Pro Leu
                        500                 505                 510

Ala Gly Thr Cys Gly Val Leu Leu Leu Ser Leu Val Ile Thr Leu Tyr
                        515                 520                 525

Cys Lys Arg Gly Arg Lys Lys Leu Leu Tyr Ile Phe Lys Gln Pro Phe
                        530                 535                 540

Met Arg Pro Val Gln Thr Thr Gln Glu Glu Asp Gly Cys Ser Cys Arg
        545                 550                 555                 560

Phe Pro Glu Glu Glu Glu Gly Gly Cys Glu Leu Arg Val Lys Phe Ser
                        565                 570                 575

Arg Ser Ala Asp Ala Pro Ala Tyr Gln Gln Gly Gln Asn Gln Leu Tyr
                        580                 585                 590

Asn Glu Leu Asn Leu Gly Arg Arg Glu Glu Tyr Asp Val Leu Asp Lys
                        595                 600                 605

Arg Arg Gly Arg Asp Pro Glu Met Gly Gly Lys Pro Arg Arg Lys Asn
                        610                 615                 620

Pro Gln Glu Gly Leu Tyr Asn Glu Leu Gln Lys Asp Lys Met Ala Glu
        625                 630                 635                 640

Ala Tyr Ser Glu Ile Gly Met Lys Gly Glu Arg Arg Arg Gly Lys Gly
                        645                 650                 655

His Asp Gly Leu Tyr Gln Gly Leu Ser Thr Ala Thr Lys Asp Thr Tyr
                        660                 665                 670

Asp Ala Leu His Met Gln Ala Leu Pro Pro Arg
                        675                 680

<210> SEQ ID NO 28
<211> LENGTH: 2052
<212> TYPE: DNA
<213> ORGANISM: Artificial Sequence
<220> FEATURE:
<223> OTHER INFORMATION: pTRPE.MuSKI96A_opt.BBz CAAR

<400> SEQUENCE: 28
atggagtttg ggctgagctg gcttttctt gtggctattt taaaaggtgt ccagtgcgga     60
tcccttccta aagccccggt aattaccacc ccattggaga ccgtcgatgc ccttgtagag    120
gaggttgcaa cctttatgtg tgctgtagag tcttacccgc aaccagagat atcatggacc    180
cgaaacaaga ttttgatcaa gttgttcgat actcgatact ccattcgaga gaacgggcag    240
ctcctcacta tattgagcgt agaagacagt gatgacggtg catactgctg caccgctaac    300
aatggtgtgg gaggagcagt ggaaagttgt ggcgcacttc aagtaaaaat gaagccgaaa    360
attacgagac tccgattaa cgttaaaatt atagaggggc tgaaagctgt cctgccatgt    420
accacaatgg gtaatcccaa gcccagcgta tcctggatca aggtgattc accgttgaga    480 gaaaattcta ggatagcggt attggagtcc ggctcactta gaattcacaa cgtccaaaaa    540
gaagatgctg tcagtacag atgtgtcgcc aaaaattctc tcggaactgc atacagtaaa    600
gtggtaaagc ttgaagttga agtgtttgca aggattctgc gagccccgga gtcacacaat    660
gtaaccttcg gttctttttgt gactcttcat tgtaccgcta ctggaatccc agttccacg    720 attacgtgga ttgaaaacgg aaatgccgtc tcaagcggca gcatacagga gtccgtgaag    780
gatagagtca tagactcccg attgcaactg ttcattacaa agcctggcct ttatacatgc    840
```

| attgctacaa caagcatgg tgagaaattc agtacagcta aggccgccgc aacaatttcc | 900 |
|---|---|
| attgcagagt ggagcaagcc acaaaaagat aacaagggtt actgtgccca atatcgaggg | 960 |
| gaagtttgta acgctgtact tgctaaggac gctctcgtct tcttgaatac atcctacgcg | 1020 |
| gacccggagg aagcccagga gctcttggtg cacactgcat ggaatgaact taaagtagtg | 1080 |
| tcccctgtat gccggccagc cgcggaagcg ttgctctgta atcacatttt ccaagaatgt | 1140 |
| tcaccagggg tagtaccaac gcctatcccg atatgtcggg aatattgtct ggcggtcaaa | 1200 |
| gagctctttt gtgctaaaga atggctcgtg atggaggaaa aaactcatcg gggtttgtat | 1260 |
| cgctcagaaa tgcacctgct gagtgtccca gaatgctcca agttgcccag tatgcactgg | 1320 |
| gaccctacgg cgtgcgcacg cttgcctcac ctggactaca ataaagaaaa tctgaaaaca | 1380 |
| tttcccccta tgactagcag taagccttct gttgatattc aaacctccc gtcatcctct | 1440 |
| tcatcttctt tctctgtcag cccgacttat tccatgactg gtggcggagg ttctggaggt | 1500 |
| ggaggttcct ccggaatcta catctgggcg cccttggccg ggacttgtgg ggtccttctc | 1560 |
| ctgtcactgg ttatcaccct ttactgcaaa cggggcagaa agaaactcct gtatatattc | 1620 |
| aaacaaccat ttatgagacc agtacaaact actcaagagg aagatggctg tagctgccga | 1680 |
| tttccagaag aagaagaagg aggatgtgaa ctgagagtga agttcagcag gagcgcagac | 1740 |
| gcccccgcgt accagcaggg ccagaaccag ctctataacg agctcaatct aggacgaaga | 1800 |
| gaggagtacg atgttttgga caagagacgt ggccgggacc ctgagatggg gggaaagccg | 1860 |
| agaaggaaga accctcagga aggcctgtac aatgaactgc agaaagataa gatggcggag | 1920 |
| gcctacagtg agattgggat gaaaggcgag cgccggaggg gcaaggggca cgatggcctt | 1980 |
| taccagggtc tcagtacagc caccaaggac acctacgacg cccttcacat gcaggccctg | 2040 |
| cccccctcgct aa | 2052 |

<210> SEQ ID NO 29
<211> LENGTH: 1416
<212> TYPE: DNA
<213> ORGANISM: Artificial Sequence
<220> FEATURE:
<223> OTHER INFORMATION: MuSK-I96A extracellular domain (codon optimized)

<400> SEQUENCE: 29

| cttcctaaag ccccggtaat taccacccca ttggagaccg tcgatgccct tgtagaggag | 60 |
|---|---|
| gttgcaacct ttatgtgtgc tgtagagtct tacccgcaac cagagatatc atggacccga | 120 |
| aacaagattt tgatcaagtt gttcgatact cgatactcca ttcgagagaa cgggcagctc | 180 |
| ctcactatat tgagcgtaga agacagtgat gacggtgcat actgctgcac cgctaacaat | 240 |
| ggtgtgggag gagcagtgga agttgtggc gcacttcaag taaaaatgaa gccgaaaatt | 300 |
| acgagacctc cgattaacgt taaaattata gaggggctga agctgtcct gccatgtacc | 360 |
| acaatgggta atcccaagcc cagcgtatcc tggatcaaag tgattcacc gttgagagaa | 420 |
| aattctagga tagcggtatt ggagtccggc tcacttagaa ttcacaacgt ccaaaaagaa | 480 |
| gatgctggtc agtacagatg tgtcgccaaa aattctctcg gaactgcata cagtaaagtg | 540 |
| gtaaagcttg aagttgaagt gtttgcaagg attctgcgag ccccggagtc acacaatgta | 600 |
| accttcggtt cttttgtgac tcttcattgt accgctactg gaatcccagt tcccacgatt | 660 |
| acgtggattg aaaacggaaa tgccgtctca gcggcagca tacaggagtc cgtgaaggat | 720 |
| agagtcatag actcccgatt gcaactgttc attacaaagc ctggcctta tacatgcatt | 780 |

-continued

```
gctacaaaca agcatggtga gaaattcagt acagctaagg ccgccgcaac aatttccatt    840
gcagagtgga gcaagccaca aaaagataac aagggttact gtgcccaata tcgaggggaa    900
gtttgtaacg ctgtacttgc taaggacgct ctcgtcttct tgaatacatc ctacgcggac    960
ccggaggaag cccaggagct cttggtgcac actgcatgga atgaacttaa agtagtgtcc   1020
cctgtatgcc ggccagccgc ggaagcgttg ctctgtaatc acattttcca agaatgttca   1080
ccaggggtag taccaacgcc tatcccgata tgtcgggaat attgtctggc ggtcaaagag   1140
ctcttttgtg ctaaagaatg gctcgtgatg gaggaaaaaa ctcatcgggg tttgtatcgc   1200
tcagaaatgc acctgctgag tgtcccagaa tgctccaagt tgcccagtat gcactgggac   1260
cctacggcgt gcgcacgctt gcctcacctg gactacaata agaaaatct gaaaacattt     1320 cccctatga ctagcagtaa gccttctgtt gatattccaa acctcccgtc atcctcttca    1380
tcttctttct ctgtcagccc gacttattcc atgact                             1416
```

<210> SEQ ID NO 30
<211> LENGTH: 683
<212> TYPE: PRT
<213> ORGANISM: Artificial Sequence
<220> FEATURE:
<223> OTHER INFORMATION: pTRPE.MuSKI96A_opt.BBz CAAR

<400> SEQUENCE: 30

```
Met Glu Phe Gly Leu Ser Trp Leu Phe Leu Val Ala Ile Leu Lys Gly
1               5                   10                  15

Val Gln Cys Gly Ser Leu Pro Lys Ala Pro Val Ile Thr Thr Pro Leu
            20                  25                  30

Glu Thr Val Asp Ala Leu Val Glu Glu Val Ala Thr Phe Met Cys Ala
        35                  40                  45

Val Glu Ser Tyr Pro Gln Pro Glu Ile Ser Trp Thr Arg Asn Lys Ile
    50                  55                  60

Leu Ile Lys Leu Phe Asp Thr Arg Tyr Ser Ile Arg Glu Asn Gly Gln
65                  70                  75                  80

Leu Leu Thr Ile Leu Ser Val Glu Asp Ser Asp Gly Ala Tyr Cys
                85                  90                  95

Cys Thr Ala Asn Asn Gly Val Gly Gly Ala Val Glu Ser Cys Gly Ala
            100                 105                 110

Leu Gln Val Lys Met Lys Pro Lys Ile Thr Arg Pro Pro Ile Asn Val
        115                 120                 125

Lys Ile Ile Glu Gly Leu Lys Ala Val Leu Pro Cys Thr Thr Met Gly
    130                 135                 140

Asn Pro Lys Pro Ser Val Ser Trp Ile Lys Gly Asp Ser Pro Leu Arg
145                 150                 155                 160

Glu Asn Ser Arg Ile Ala Val Leu Glu Ser Gly Ser Leu Arg Ile His
                165                 170                 175

Asn Val Gln Lys Glu Asp Ala Gly Gln Tyr Arg Cys Val Ala Lys Asn
            180                 185                 190

Ser Leu Gly Thr Ala Tyr Ser Lys Val Val Lys Leu Glu Val Glu Val
        195                 200                 205

Phe Ala Arg Ile Leu Arg Ala Pro Glu Ser His Asn Val Thr Phe Gly
    210                 215                 220

Ser Phe Val Thr Leu His Cys Thr Ala Thr Gly Ile Pro Val Pro Thr
225                 230                 235                 240

Ile Thr Trp Ile Glu Asn Gly Asn Ala Val Ser Ser Gly Ser Ile Gln
                245                 250                 255
```

```
Glu Ser Val Lys Asp Arg Val Ile Asp Ser Arg Leu Gln Leu Phe Ile
            260                 265                 270

Thr Lys Pro Gly Leu Tyr Thr Cys Ile Ala Thr Asn Lys His Gly Glu
            275                 280                 285

Lys Phe Ser Thr Ala Lys Ala Ala Thr Ile Ser Ile Ala Glu Trp
            290                 295                 300

Ser Lys Pro Gln Lys Asp Asn Lys Gly Tyr Cys Ala Gln Tyr Arg Gly
305                 310                 315                 320

Glu Val Cys Asn Ala Val Leu Ala Lys Asp Ala Leu Val Phe Leu Asn
            325                 330                 335

Thr Ser Tyr Ala Asp Pro Glu Glu Ala Gln Glu Leu Leu Val His Thr
            340                 345                 350

Ala Trp Asn Glu Leu Lys Val Val Ser Pro Val Cys Arg Pro Ala Ala
            355                 360                 365

Glu Ala Leu Leu Cys Asn His Ile Phe Gln Glu Cys Ser Pro Gly Val
            370                 375                 380

Val Pro Thr Pro Ile Pro Ile Cys Arg Glu Tyr Cys Leu Ala Val Lys
385                 390                 395                 400

Glu Leu Phe Cys Ala Lys Glu Trp Leu Val Met Glu Glu Lys Thr His
            405                 410                 415

Arg Gly Leu Tyr Arg Ser Glu Met His Leu Leu Ser Val Pro Glu Cys
            420                 425                 430

Ser Lys Leu Pro Ser Met His Trp Asp Pro Thr Ala Cys Ala Arg Leu
            435                 440                 445

Pro His Leu Asp Tyr Asn Lys Glu Asn Leu Lys Thr Phe Pro Pro Met
            450                 455                 460

Thr Ser Ser Lys Pro Ser Val Asp Ile Pro Asn Leu Pro Ser Ser Ser
465                 470                 475                 480

Ser Ser Ser Phe Ser Val Ser Pro Thr Tyr Ser Met Thr Gly Gly Gly
            485                 490                 495

Gly Ser Gly Gly Gly Gly Ser Ser Gly Ile Tyr Ile Trp Ala Pro Leu
            500                 505                 510

Ala Gly Thr Cys Gly Val Leu Leu Leu Ser Leu Val Ile Thr Leu Tyr
            515                 520                 525

Cys Lys Arg Gly Arg Lys Lys Leu Leu Tyr Ile Phe Lys Gln Pro Phe
            530                 535                 540

Met Arg Pro Val Gln Thr Thr Gln Glu Glu Asp Gly Cys Ser Cys Arg
545                 550                 555                 560

Phe Pro Glu Glu Glu Glu Gly Gly Cys Glu Leu Arg Val Lys Phe Ser
            565                 570                 575

Arg Ser Ala Asp Ala Pro Ala Tyr Gln Gln Gly Gln Asn Gln Leu Tyr
            580                 585                 590

Asn Glu Leu Asn Leu Gly Arg Arg Glu Glu Tyr Asp Val Leu Asp Lys
            595                 600                 605

Arg Arg Gly Arg Asp Pro Glu Met Gly Gly Lys Pro Arg Arg Lys Asn
            610                 615                 620

Pro Gln Glu Gly Leu Tyr Asn Glu Leu Gln Lys Asp Lys Met Ala Glu
625                 630                 635                 640

Ala Tyr Ser Glu Ile Gly Met Lys Gly Glu Arg Arg Arg Gly Lys Gly
            645                 650                 655

His Asp Gly Leu Tyr Gln Gly Leu Ser Thr Ala Thr Lys Asp Thr Tyr
            660                 665                 670
```

```
Asp Ala Leu His Met Gln Ala Leu Pro Pro Arg
        675                 680

<210> SEQ ID NO 31
<211> LENGTH: 55
<212> TYPE: PRT
<213> ORGANISM: Artificial Sequence
<220> FEATURE:
<223> OTHER INFORMATION: CD8 alpha hinge

<400> SEQUENCE: 31

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 32
<211> LENGTH: 165
<212> TYPE: DNA
<213> ORGANISM: Artificial Sequence
<220> FEATURE:
<223> OTHER INFORMATION: CD8 alpha hinge

<400> SEQUENCE: 32
ttcgtgccgg tcttcctgcc agcgaagcca accacgacgc cagcaccgcg accaccaaca     60
cctgcgccca ccatcgcgtc gcagcccctg tccctgcgcc agaggcgtg cagaccagca    120 gcggggggcg cagtgcacac gaggggggctg gacttcgcct gtgat                  165
```

COMPOSITIONS AND METHODS OF MUSCLE SPECIFIC KINASE CHIMERIC AUTOANTIBODY RECEPTOR CELLS

CROSS-REFERENCE TO RELATED APPLICATION

The present application is entitled to priority under 35 U.S.C. § 119(e) to U.S. Provisional Patent Application No. 62/680,769 filed Jun. 5, 2018, which is hereby incorporated by reference in its entirety herein.

BACKGROUND OF THE INVENTION

Myasthenia gravis (MG) is one of the most common autoantibody-mediated diseases in humans, with an incidence of 3,000 new patients per year and a prevalence of 25,000-50,000 total patients in the United States; greater than one million patients are estimated to have myasthenia gravis in the US, Europe, and Asia. Antibody attack of proteins expressed at the neuromuscular junction (NMJ) leads to muscle weakness, manifesting as drooping of the eyes, double vision, unstable gait, slurred speech, and difficulty swallowing and breathing. Autoantibodies produced by MG patients destroy the NMJ by fixing complement or dissembling acetylcholine receptor (AChR) clusters. Formation of AChR clusters, which is indispensable for signal transduction via the AChR, depends on activation of the transmembrane protein, muscle-specific kinase (MuSK). Most MG patients exhibit either anti-AChR antibodies (85%) or anti-MuSK antibodies (4%). 11% of patients are classified as "seronegative," which has been attributed to low titer antibodies against AChR, MuSK, or other NMJ proteins such as LRP4. Myasthenic crisis, defined as the need for mechanical ventilation due to life-threatening muscle weakness of the muscles that control breathing, occurs in 10-20% of MG patients; the overall mortality from myasthenic crisis is 4.5%.

Currently, mild MG is treated with acetylcholinesterase inhibitors to inhibit acetylcholine breakdown, although MuSK-type MG patients often do not respond to this form of therapy. More severe MG is treated with prednisone, anti-proliferatives such as azathioprine, and rituximab in more advanced disease. Anti-MuSK antibody titers drop after rituximab, even to the negative range, indicating that short-lived plasma cells produce the majority of anti-MuSK antibody.

There is an urgent need in the art for achieving a more specific and effective treatment for myasthenia gravis. This invention addresses this need.

SUMMARY OF THE INVENTION

Provided is a polynucleotide encoding a chimeric autoantibody receptor (CAAR), wherein the polynucleotide encodes an extracellular domain comprising a muscle-specific kinase (MuSK) autoantigen or fragment thereof, and optionally, a transmembrane domain, an intracellular domain of a costimulatory molecule, and/or a signaling domain. In some embodiments, MuSK autoantigen or fragment thereof is encoded by a nucleic acid sequence comprising a nucleic acid sequence selected from the group consisting of SEQ ID NOs: 3, 6, 26 and 29. In further embodiments, the MuSK autoantigen or fragment thereof is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a nucleic acid sequence selected from the group consisting of SEQ ID NOs: 3, 6, 26 and 29. In some embodiments, the MuSK autoantigen or fragment thereof comprises an amino acid sequence selected from the group consisting of SEQ ID NOs: 11 and 23. In further embodiments, the MuSK autoantigen or fragment thereof comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs: 11 and 23.

In some embodiments, the transmembrane domain comprises a CD8 alpha transmembrane domain. In further embodiments, the CD8 alpha transmembrane domain is encoded by a nucleic acid sequence comprising SEQ ID NO: 5 or 18. In yet further embodiments, the CD8 alpha transmembrane domain comprises the amino acid sequence of SEQ ID NO: 13.

In some embodiments, the intracellular domain of a costimulatory molecule comprises a 4-1BB intracellular domain. In further embodiments, the 4-1BB intracellular domain is encoded by a nucleic acid sequence comprising SEQ ID NO: 7 or 19. In yet further embodiments, the 4-1BB intracellular domain comprises the amino acid sequence of SEQ ID NO: 14.

In some embodiments, the signaling domain comprises a CD3 zeta signaling domain. In further embodiments, the CD3 zeta signaling domain is encoded by a nucleic acid sequence comprising SEQ ID NO: 8 or 20. In yet further embodiments, the CD3 zeta signaling domain comprises an amino acid sequence of SEQ ID NO: 15.

In some embodiments, the CAAR is encoded by a nucleic acid sequence selected from the group consisting of SEQ ID NOs: 1, 16, 21, 24, 25 and 28. In further embodiments, the CAAR comprises an amino acid sequence selected from the group consisting of SEQ ID NOs: 9, 22, 27 and 30.

In some embodiments, the CAAR comprises an extracellular domain comprising a muscle-specific kinase (MuSK) autoantigen or fragment thereof, a killer immunoglobulin-like receptor (KIR) transmembrane domain and a KIR cytoplasmic domain.

Provided is a vector comprising the polynucleotide of any one of the preceding embodiments. In some embodiments, the vector is a lentiviral vector. In further embodiments, the vector is a RNA vector.

In some embodiments, the vector comprises an inducible promoter operably linked to the polynucleotide encoding the CAAR.

Also provided is a chimeric autoantibody receptor (CAAR) comprising an extracellular domain comprising a muscle-specific kinase (MuSK) autoantigen or fragment thereof.

Also provided is a chimeric autoantibody receptor (CAAR) comprising an extracellular domain comprising a muscle-specific kinase (MuSK) autoantigen or fragment thereof, a transmembrane domain, an intracellular domain of a costimulatory molecule, and/or a signaling domain.

In some embodiments, the MuSK autoantigen or fragment thereof is encoded by a nucleic acid sequence selected from the group consisting of SEQ ID NOs: 3, 6, 26 and 29. In further embodiments, the MuSK autoantigen or fragment thereof is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a nucleic acid sequence selected from the group consisting of SEQ ID NOs: 3, 6, 26 and 29.

In some embodiments, the MuSK autoantigen or fragment thereof comprises an amino acid sequence selected from the group consisting of SEQ ID NOs: 11 and 23. In further embodiments, the MuSK autoantigen or fragment thereof comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs: 11 and 23.

In some embodiments, the transmembrane domain comprises a CD8 alpha transmembrane domain. In further embodiments, the CD8 alpha transmembrane domain is encoded by a nucleic acid sequence comprising SEQ ID NO: 5 or 18. In yet further embodiments, the CD8 alpha transmembrane domain comprises the amino acid sequence of SEQ ID NO: 13.

In some embodiments, the intracellular domain of a costimulatory molecule comprises a 4-1BB intracellular domain. In further embodiments, the 4-1BB intracellular domain is encoded by a nucleic acid sequence comprising SEQ ID NO: 7 or 19. In yet further embodiments, the 4-1BB intracellular domain comprises the amino acid sequence of SEQ ID NO: 14.

In some embodiments, the signaling domain comprises a CD3 zeta signaling domain. In further embodiments, the CD3 zeta signaling domain is encoded by a nucleic acid sequence comprising SEQ ID NO: 8 or 20. In yet further embodiments, the CD3 zeta signaling domain comprises an amino acid sequence of SEQ ID NO: 15.

In some embodiments, the CAAR is encoded by a nucleic acid sequence selected from the group consisting of SEQ ID NOs: 1, 16, 21, 24, 25 and 28. In further embodiments, the CAAR comprises an amino acid sequence selected from the group consisting of SEQ ID NOs: 9, 22, 27 and 30.

In some embodiments, the CAAR comprises an extracellular domain comprising an extracellular domain comprising a muscle-specific kinase (MuSK) autoantigen or fragment thereof, a KIR transmembrane domain, and a KIR cytoplasmic domain.

Provided is a genetically modified cell comprising the CAAR of any one of the previous embodiments. In some embodiments, the cell expresses the CAAR and has high affinity to autoantibody-based BCRs on B cells. In some embodiments, the cell expresses the CAAR and induces killing of B cells expressing autoantibodies or B cells that may mature into antibody-secreting cells. In further embodiments, the cell expresses the CAAR and has limited toxicity toward healthy cells. In yet further embodiments, the cell is selected from the group consisting of a helper T cell, a cytotoxic T cell, a memory T cell, a regulatory T cell, a gamma delta T cell, a natural killer cell, a cytokine induced killer cell, a cell line thereof, a T memory stem cell, a T cell derived from a pluripotent stem and other effector cell.

Also provided is a genetically modified cell comprising: (a) the chimeric autoantibody receptor of any one of the preceding embodiments; and (b) DAP12.

In some embodiments, the cell of any one of the preceding embodiments comprises a polynucleotide encoding the CAAR operably linked to an inducible promoter.

Provided is a pharmaceutical composition comprising the polynucleotide of any one of the preceding embodiments, the CAAR of any one of the preceding embodiments, or the cell of any one of the preceding embodiments, and a pharmaceutically acceptable excipient.

Provided is a method for treating an autoantibody-mediated neuromuscular junction (NMJ) disease in a subject, the method comprising: administering to the subject an effective amount of a genetically modified cell comprising a polynucleotide encoding a chimeric autoantibody receptor (CAAR), wherein the polynucleotide encodes an extracellular domain comprising a muscle-specific kinase (MuSK) autoantigen or fragment thereof, and optionally a transmembrane domain, an intracellular domain of a costimulatory molecule, and/or a signaling domain, thereby treating the autoantibody-mediated NMJ disease in the subject.

Provided is a method for preventing or reducing neuromuscular junction (NMJ) damage in a subject at risk of or suffering from an autoantibody-mediated NMJ disease, the method comprising: administering to the subject an effective amount of a genetically modified cell comprising a polynucleotide encoding a chimeric autoantibody receptor (CAAR), wherein the polynucleotide encodes an extracellular domain comprising a muscle-specific kinase (MuSK) autoantigen or fragment thereof, and optionally a transmembrane domain, an intracellular domain of a costimulatory molecule, and/or a signaling domain, thereby preventing or reducing NMJ damage in the subject.

Provided is a method for treating an autoantibody-mediated neuromuscular junction (NMJ) disease in a subject, the method comprising: administering to the subject an effective amount of a genetically modified cell comprising: (a) a polynucleotide encoding a chimeric autoantibody receptor (CAAR), wherein the polynucleotide encodes an extracellular domain comprising a MuSK autoantigen or fragment thereof, a killer immunoglobulin-like receptor (KIR) transmembrane domain and a KIR cytoplasmic domain; and (b) a polynucleotide encoding DAP12, thereby treating the autoantibody-mediated NMJ disease in the subject.

Provided is a method for preventing or reducing neuromuscular junction (NMJ) damage in a subject at risk of or suffering from an autoantibody-mediated NMJ disease, the method comprising: administering to the subject an effective amount of a genetically modified cell comprising: (a) a polynucleotide encoding a chimeric autoantibody receptor (CAAR), wherein the polynucleotide encodes an extracellular domain comprising a MuSK autoantigen or fragment thereof, a killer immunoglobulin-like receptor (KIR) transmembrane domain and a KIR cytoplasmic domain; and (b) a polynucleotide encoding DAP12, thereby treating the autoantibody-mediated NMJ disease in the subject.

In some embodiments, the polynucleotide is any one of the polynucleotides described herein.

In some embodiments, the CAAR is any one of the CAARs described herein.

In some embodiments, the autoantibody-mediated NMJ disease is myasthenia gravis (MG).

In some embodiments, the subject is a human.

In some embodiments, the modified cell targets B cells.

In some embodiments, the modified cell is a T cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A: A schematic diagram of MuSK CAAR constructs pTRPE.MuSK$_{WT}$.BBz CAAR and pTRPE.MuSK$_{I96A}$.BBz CAAR. FIG. 3B: Full length MuSK CAAR includes all MuSK epitopes as described in the prior art (Huijbers et al. *Proc. Natl. Acad. Sci.* 110(51): 20783-20788).

FIG. 4A: Schematic diagram of MuSK wild type (wt)/I96A CAAR constructs. An isoleucine at amino acid position 96 of the MuSK wt ECD is mutated into alanine and indicated as a white box. FIG. 4B: MuSK wt/I96A CAAR in pTRPE lentiviral vector was transduced into primary human CD3$^+$ T cells. At day five after transduction, surface expression of MuSK wt/I96A CAAR was detected using anti-MuSK antibody 4A3.

FIG. 5A: Diagram of MuSK CAAR constructs pTRPE.MuSK$_{WT}$.BBz CAAR and pTRPE.MuSK$_{I96A}$.BBz CAAR. FIG. 5B (Upper panel): Surface expression of MuSK CAARs on non-transfected (Non, left), MuSK$_{WT}$ (middle), and MuSK$_{I96A}$ transfected cells(right) were detected using anti-MuSK-APC antibody. FIG. 5B (Lower panel): Mean fluorescence intensity of anti-MuSK-APC antibody in the upper panel: non-transfected cells (right column), MuSK$_{WT}$ (middle column), and MuSK$_{I96A}$ (left column). 293T cells were transfected using Lipofectamine 2000. CD3$^+$ T cells were transduced using Lentivirus.

FIGS. 11A-11B illustrate that MuSK wt/I96A CAAR-T cells kill anti-MuSK antibody producing 4A3 hybridoma cells and secrete IFNγ. FIG. 11A: 4A3 hybridoma cells were labeled using $^{51}$Cr and co-cultured for 21 hours with MuSK wt/I96A CAAR-T cells or CART-19 cells. Percent specific lysis was calculated by the following equation: % of specific lysis=[(experimental sample–spontaneous cell death sample)/(maximum cell death sample–spontaneous cell death sample)]*100. Maximum cell death was induced by adding 5% SDS (final 5%). FIG. 11B: MuSK wt/I96A CAAR-T cells were co-cultured with unlabeled 4A3 hybridoma cells for 21 hours. The supernatant was collected after spin-down. Human IFNγ was detected by Human IFN-gamma DuoSet ELISA kit (R&D Systems).

FIG. 12A: 0.5×10$^6$ CBG$^+$hIgG$^+$ Nalm6 3-28 cells were injected intravenously into NSG mice after pre-treatment with intravenous immunoglobulin (IVIG, Privigen, 600 mg/kg intraperitoneal injection daily for 2 days). After 4 days, 5×10$^6$ indicated CAAR- or CAR-T cells were injected intravenously (orange arrow). Non-transduced (NTD) T cells and Desmoglein (DSG) 3 EC1-3 CAAR-T cells were considered as a negative control and CART-19 cells were used as a positive control since Nalm6 cells express CD19. Bioluminescence was quantified with an IVIS Lumina at day 1, 3, 5, 7, and 9. Simultaneously, 600 mg/kg IVIG was also administered every two days intraperitoneally. Total flux was quantified using Living Image 4.5 software (PerkinElmer). Images were consecutively taken with a 1 minute interval. FIG. 12B: FIG. 12B shows bioluminescence flux (photons/sec) for each treatment group in FIG. 12A, which illustrate that MuSK wt/I96A CAAR T cells control anti-MuSK Nalm6 target cells, comparable in efficacy to CART-19 cells, whereas negative control NTD and DSG3 EC1-3 CAAR T cells do not control anti-MuSK Nalm6 target cell outgrowth.

FIG. 13A: Mouse body weight was measured right after the imaging in FIG. 12A. Percentage of initial body weight was calculated relative to Day 1 (100%). FIG. 13B: At 24 hours after T cell injection, blood samples were collected by retro-orbital bleeding. Mouse sera were kept at −20° C. for further analysis. Human IFNγ was detected by Human IFN-gamma DuoSet ELISA kit (R&D Systems). Unpaired two-tailed t test with ND463 NTD; ns: non-significant, **: <0.005.

DETAILED DESCRIPTION

Figure 1:
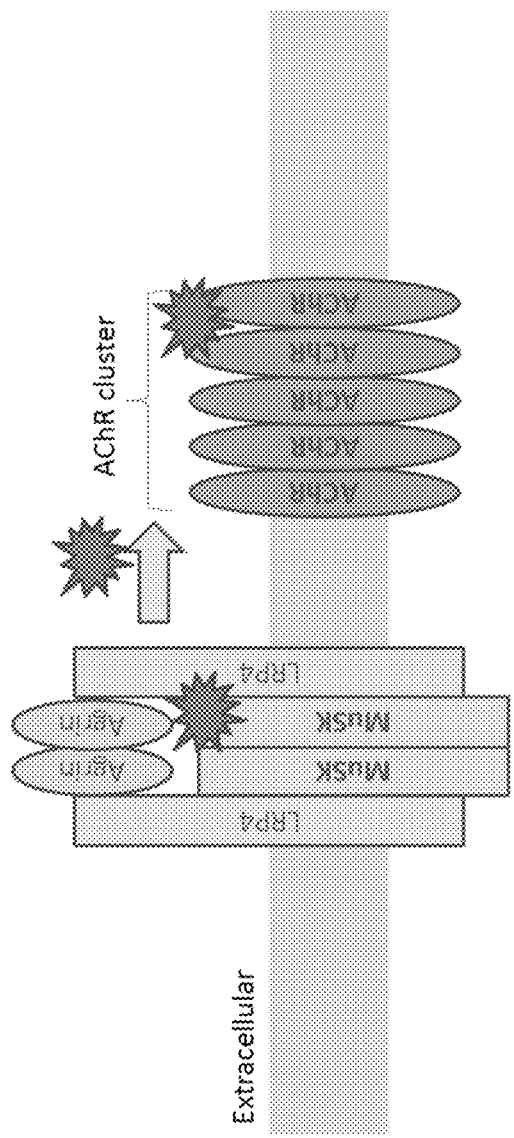
FIG. 1 is an illustration showing that autoantibodies from MG patients destroy AChR clusters and the NMJ: The anti-AChR antibodies interfere with AChR clusters and the anti-MuSK antibodies disrupt the MuSK/LRP4 complex, which regulates AChR clustering.

The invention includes a chimeric autoantibody receptor (CAAR) specific for anti-muscle-specific kinase (MuSK) B cell receptor (BCR), compositions comprising the CAAR, polynucleotides encoding the CAAR, vectors comprising a polynucleotide encoding the CAAR, and recombinant cells, e.g., T cells comprising the CAAR.

The invention also includes methods of making a genetically modified cell, e.g., a genetically modified T cell expressing a MuSK-CAAR wherein the expressed CAAR comprises a MuSK extracellular domain.

The present invention also relates generally to the use of cells, e.g., T cells engineered to express a CAAR to treat a neuromuscular junction (NMJ) disease (e.g., Myasthenia gravis (MG)) associated with targeting of self-antigens (e.g., MuSK). In one embodiment, the cells, e.g., T cells, expressing the CAAR of the invention specifically bind to and kill anti-MuSK BCR-expressing cells, but do not bind to and kill normal BCR-expressing cells.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule that binds with an antigen. Antibodies can be intact immunoglobulins derived from natural sources or from recombinant sources and can be immunoreactive portions of intact immunoglobulins. Antibodies are typically tetramers of immunoglobulin molecules. The antibody may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "high affinity" as used herein refers to high specificity in binding or interacting or attraction of a binding molecule to a target molecule. For example, in some embodiments, the binding molecule may have an affinity for the target molecule stronger than 100 nM, 50 nM, 20 nM, 15 nM, 10 nM, 9 nM, 8 nM, 7 nM, 6 nM, 5 nM, 4 nM, 3 nM, 2 nM, or 1 nM, e.g., as determined by surface plasmon resonance.

The term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a cell, or a biological fluid.

By "autoantigen" is meant an endogenous antigen that stimulates production of an autoimmune response, such as production of autoantibodies. Autoantigen also includes a self-antigen or antigen from a normal tissue that is the target of a cell-mediated or an antibody-mediated immune response that may result in the development of an autoimmune disease. Examples of autoantigens include, but are not limited to, MuSK, and fragments thereof.

The term "limited toxicity" as used herein, refers to the peptides, polynucleotides, cells and/or antibodies of the invention manifesting a lack of substantially negative biological effects, or substantially negative physiological symptoms toward a healthy cell, non-diseased cell, non-target cell or population of such cells either in vitro or in vivo.

"Autoantibody" refers to an antibody that is specific for an autoantigen.

The term "autoimmune disease" as used herein is defined as a disorder or condition that results from an antibody mediated autoimmune response against autoantigens. An autoimmune disease results in the production of autoantibodies that are inappropriately produced and/or excessively produced to a self-antigen or autoantigen.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

"Chimeric autoantibody receptor" or "CAAR" refers to an engineered receptor that is expressed on a cell, e.g., a T cell, or any other effector cell type, e.g., an effector cell type capable of cell-mediated cytotoxicity. The CAAR includes an antigen or fragment thereof that is specific for a BCR and/or autoantibody. The CAAR optionally also includes a transmembrane domain, an intracellular domain and/or a signaling domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the extracellular regions of the CAAR of the invention can be replaced with other amino acid residues having a similar side chain or charge and the altered CAAR can be tested for the ability to bind autoantibodies using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MEW molecule loaded with peptide, mediates a T cell response, including, but not limited to, proliferation, activation, differentiation, and the like.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Effective amount" or "therapeutically effective amount" are used interchangeably herein, and refer to an amount of a compound, formulation, material, or composition, as described herein effective to achieve a particular biological result. Such results may include, but are not limited to, elimination of anti-MuSK B cells and the antibodies they produce as determined by any means suitable in the art.

The term "effector function" refers to a specialized function of a cell.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by a promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Intracellular domain" refers to a portion or region of a molecule that resides inside a cell.

The term "intracellular signaling domain" is meant to include any full-length or truncated portion of the intracellular domain sufficient to transduce the effector function signal.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein, "MuSK" or "MuSK$_{WT}$" relates to the wild type polynucleotide and polypeptide isoform (e.g. Gene ID: 4593; NM_005592.3; NP_005583.1; with Consensus coding Sequence (CDS) CCDS48005.1) of the muscle skeletal receptor tyrosine-protein kinase. In some embodiments, the MuSK polynucleotide is codon optimized. In some embodiments, the I96A variant (MuSK$_{I96A}$) is used in the compositions and methods of the present invention. It is known in the art that the mutation of MuSK$_{I96A}$ has minimal effect on antibody binding but might disrupt binding with LRP4, which binds the first Ig-like domain of MuSK (Zhang et al., J Biol Chem. 2011 Nov. 25; 286(47): 40624-40630). In some embodiments, MuSK$_{I96A}$ binds anti-MuSK antibodies and thus has the ability to target anti-MuSK BCR.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

As used herein "plasma cells" refer to a type of white blood cells which can produce and secrete antibodies. Plasma cells are also referred to as plasmocytes, plasmacytes, or effector B cells.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. In some embodiments, a nucleic acid sequence is considered to have at least 95%, 96%, 97%, 98%, or 99% identity or homology to any nucleic acid sequence disclosed herein.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. In some embodiments, an amino acid sequence is considered to have at 95%, 96%, 97%, 98%, or 99% identity or homology to any amino acid sequence described herein.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, IL-10 and IL-15), interferons (IFNγ), and tumor necrosis factors (TNFα and TNFβ).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

"Signaling domain" refers to the portion or region of a molecule that recruits and interacts with specific proteins in response to an activating signal.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Transmembrane domain" refers to a portion or a region of a molecule that spans a lipid bilayer membrane.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MEW Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Chimeric Autoantibody Receptor (CAAR)

The present invention is partly based on the discovery that chimeric autoantibody receptors can be used to target B cells that express autoantibody-based B cell receptors, which after activation and autoantibody secretion, may cause an autoantibody-mediated neuromuscular junction (NMJ) disease (e.g., Myasthenia gravis (MG)). The invention includes a chimeric autoantibody receptor (CAAR) specific for anti-muscle-specific kinase (MuSK) B cell receptor (BCR), compositions comprising the CAAR, polynucleotides encoding the CAAR, vectors comprising a polynucleotide encoding the CAAR, and recombinant cells, e.g., T cells, comprising the CAAR. The invention also includes methods of making a genetically modified cell, e.g., a genetically modified T cell, expressing a MuSK CAAR wherein the expressed CAAR comprises a MuSK extracellular domain.

The present invention includes a technology for treating an autoantibody-mediated NMJ disease. In particular, technologies that target B cells that ultimately produce the autoantibodies and display the autoantibodies on their cell surfaces, mark these B cells as disease-specific targets for therapeutic intervention. The invention therefore includes a method for efficiently targeting and killing the pathogenic B cells in autoantibody-mediated diseases by targeting the disease-causing B cells using an antigen-specific (e.g., MuSK) chimeric autoantibody receptor (or CAAR). In one embodiment of the present invention, only specific anti-MuSK BCR-expressing B cells are killed, leaving intact the beneficial B cells and antibodies that protect from infection.

In one aspect, the invention includes a chimeric autoantibody receptor (CAAR) comprising an extracellular domain comprising a muscle-specific kinase (MuSK) autoantigen or fragment thereof.

In one aspect, the invention includes a chimeric polypeptide comprising a MuSK autoantigen or fragment thereof, wherein the MuSK autoantigen or fragment thereof is linked to the transmembrane domain of a chimeric autoantibody receptor (CAAR).

In one aspect, the invention includes a polynucleotide encoding a chimeric autoantibody receptor (CAAR), wherein the polynucleotide encodes MuSK autoantigen or fragment thereof. In some embodiments, the polynucleotide also encodes a transmembrane domain, an intracellular domain of a costimulatory molecule, and/or a signaling domain.

In one embodiment, the MuSK CAAR comprises an amino acid sequence selected from the group consisting of SEQ ID NOs: 9, 22, 27 or 30. In one embodiment, the MuSK CAAR is encoded by a nucleic acid sequence selected from the group consisting of SEQ ID NOs: 1, 16, 21, 24, 25 and 28.

In some embodiments, the MuSK CAAR comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs: 9, 22, 27 or 30. In other embodiments, the MuSK CAAR is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an nucleic acid sequence selected from the group consisting of SEQ ID NOs: 1, 16, 21, 24, 25 and 28.

Autoantigen Moiety

In one embodiment, the CAAR of the invention comprises an autoantibody binding domain otherwise referred to as an autoantigen or a fragment thereof. The choice of autoantigen for use in the present invention depends upon the type of autoantibody or BCR being targeted (e.g. anti-MuSK). For example, the autoantigen may be chosen because it recognizes a BCR or an autoantibody on a target cell, such as a BCR-expressing B cell, associated with a particular autoantibody mediated disease state, e.g. Myasthenia gravis (MG).

In some instances, it is beneficial that the autoantibody binding domain is derived from the same species in which the CAAR will ultimately be used. For example, for use in humans, it may be beneficial that the autoantibody binding domain of the CAAR comprises a human autoantigen (or fragment thereof) that binds a human BCR or autoantibody or a fragment thereof.

In one exemplary embodiment, a genetically engineered chimeric autoantibody receptor includes MuSK or fragments thereof, which binds an anti-MuSK BCR, e.g., an anti-MuSK BCR on a B cell in a subject.

In one embodiment, the CAAR comprises a MuSK autoantigen or fragment thereof. In some embodiments, the extracellular domain of MuSK is encoded by a nucleic acid sequence selected from the group consisting of SEQ ID NOs: 3, 6, 26 and 29. In some embodiments, MuSK autoantigen or fragment thereof is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a nucleic acid sequence selected from the group consisting of SEQ ID NOs: 3, 6, 26 and 29. In other embodiments, the extracellular domain of MuSK comprises an amino acid sequence selected from the group consisting of SEQ ID NOs: 11 and 23. In yet other embodiments, the MuSK autoantigen or fragment thereof comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs: 11 and 23.

Transmembrane Domain

In some embodiments, the MuSK CAAR comprises a transmembrane domain that is fused to the extracellular domain of the MuSK CAAR. In one embodiment, the MuSK CAAR comprises a transmembrane domain that naturally is associated with one of the domains in the MuSK CAAR. In some instances, the transmembrane domain is selected or modified by amino acid substitution to avoid binding to the transmembrane domains of the same or different surface membrane proteins in order to minimize interactions with other members of the receptor complex.

The transmembrane domain may be derived either from a natural or from a synthetic source. When the source is natural, the domain may be derived from any membrane-bound or transmembrane protein. In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the MuSK CAAR. A glycine-serine (GS) doublet provides a particularly suitable linker.

In some instances, a variety of spacer domains before the transmembrane domain can be employed as well including the CD8 or human Ig (immunoglobulin) hinge, or a glycine-serine linker.

Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIR, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the MuSK CAAR comprises a transmembrane domain, such as, but not limited to, CD8 alpha transmembrane domain: IYIWAPLAGTCGVLLLSLVITLYC (SEQ ID NO: 13)

In some embodiments, the CD8 alpha transmembrane domain is encoded by ATCTACATCTGGGCACCCTT GGCTGGAACATGCGGGGTCCTGCTGCTGAGCTT GGTGATCACCCTTTACTGC (SEQ ID NO: 5) or ATCTACATCTGGGCGCCCTTGGCCGGGACTTGTGGGGT CCTTCTCCTGTCACT GGTTATCACCCTTTACTGC (SEQ ID NO: 18).

In some embodiments, the CD8 alpha transmembrane domain comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 13. In further embodiments, the CD8 alpha transmembrane domain is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 5 or 18.

In another embodiment, the MuSK CAAR comprises a GS linker GGGGSGGGGS (SEQ ID NO:12) which is encoded by GGAGGTGGAGGTAGTGGCGGTGGAGG CAGC (SEQ ID NO:4) or by GGTGGCGGAGGTTCTG-GAGGTGGAGGTTCC (SEQ ID NO: 17).

In some embodiments, the MuSK CAAR comprises a CD8 alpha hinge region: FVPVFLPAKPTTTPAPRPPT-PAPTIASQPLSLRPEACRPAAGGAVHTRGLDF ACD (SEQ ID NO: 31) which is encoded by:

```
                                        (SEQ ID NO: 32)
TTCGTGCCGGTCTTCCTGCCAGCGAAGCCAACCACGACGCCAGCACCGCG

ACCACCAACACCTGCGCCCACCATCGCGTCGCAGCCCCTGTCCCTGCGCC

CAGAGGCGTGCAGACCAGCAGCGGGGGGCGCAGTGCACACGAGGGGGCTG

GACTTCGCCTGTGAT.
```

In some embodiments, the hinge region comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 31, or is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 32.

Intracellular Domain of a Costimulatory Molecule

In some embodiments, the MuSK CAAR comprises an intracellular domain of a costimulatory molecule. The intracellular domain of a costimulatory molecule of the MuSK CAAR of the invention is a cytoplasmic domain responsible for the activation of at least one of the normal effector functions of the immune cell in which the MuSK CAAR has been placed in.

Effector function of a T cell, for example, may be cytolytic activity or helper activity including the secretion of cytokines. Thus, the term "intracellular domain of a costimulatory molecule" refers to the portion of a protein which transduces the effector function signal and directs the cell to perform a specialized function. While the entire intracellular domain of a costimulatory molecule can be employed, in many cases it is not necessary to use the entire domain. To the extent that a truncated portion of the intracellular domain of a costimulatory molecule is used, such truncated portion may be used in place of the intact domain as long as it transduces the effector function signal.

The intracellular domain of a costimulatory molecule refers to a portion of the CAAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, CDS, ICAM-1, GITR, BAFFR, HVEM (LIGHTR), SLAMF7, NKp80 (KLRF1), CD127, CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof. Thus, while the invention is exemplified primarily with 4-1BB (CD137) as the co-stimulatory signaling domains, other costimulatory domains are within the scope of the invention.

In one embodiment, the nucleic acid sequence of the intracellular domain of a costimulatory molecule encodes an amino acid sequence comprising costimulatory molecule 4-1BB (also known and referred to as CD137 intracellular domain):

```
                                        (SEQ ID NO: 14)
KRGRKKLLYIFKQPFMRPVQTTQEEDGCSCRFPEEEEGGCEL.
```

In still another embodiment, the nucleic acid sequence encoding the 4-1BB intracellular domain comprises:

```
                                        (SEQ ID NO: 7)
AAGCGCGGTCGCAAGAAACTGCTCTATATTTTTAAACAGCCATTCATGA

GACCTGTCCAGACCACTCAAGAGGAGGACGGATGTTCCTGTAGATTTCC

TGAAGAGGAAGAGGGGGGGTGCGAGCTG;
or
                                        (SEQ ID NO: 19)
AAACGGGGCAGAAAGAAACTCCTGTATATATTCAAACAACCATTTATGA

GACCAGTACAAACTACTCAAGAGGAAGATGGCTGTAGCTGCCGATTTCC

AGAAGAAGAAGAAGGAGGATGTGAACTG;.
```

In some embodiments, the 4-1BB intracellular domain comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 14. In other embodiments, the 4-1BB intracellular domain is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a nucleic acid sequence selected from the group consisting of SEQ ID NOs: 7 and 19.

The human intracellular 4-1BB domain provides co-stimulatory intracellular signaling upon binding to the extracellular autoantigen, such as MuSK, or a fragment thereof, without the need of its original ligand.

It is well recognized that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Signaling Domain

In some embodiments, the MuSK CAAR comprises a signaling domain. Primary cytoplasmic signaling sequences regulate primary activation of the TCR complex either in a stimulatory manner or in an inhibitory manner. Primary cytoplasmic signaling sequences that act in a stimulatory manner may contain signaling motifs which are known as immunoreceptor tyrosine-based activation motifs or ITAMs.

Examples of ITAM containing primary signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that signaling molecule in the CAAR of the invention comprises a signaling domain derived from CD3 zeta.

In one embodiment, the signaling domain of the CAAR can be designed to comprise the CD3 zeta signaling domain by itself or combined with any other desired cytoplasmic domain(s) useful in the context of the CAAR of the invention. For example, the signaling domain of the CAAR can comprise a CD3 zeta chain portion and a costimulatory signaling domain.

In some embodiments, the MuSK CAAR comprises a CD3 zeta signaling domain by itself or in combination with any other desired cytoplasmic domain(s) useful in the context of the MuSK CAAR of the invention. For example, the MuSK CAAR can comprise a CD3 zeta chain portion and an intracellular domain of a costimulatory molecule. In some embodiments, the CD3 zeta chain portion is a human T-cell surface glycoprotein CD3 zeta chain isoform 3 intracellular domain (human CD247). The human intracellular CD3 zeta domain provides stimulatory intracellular signaling upon binding to the extracellular autoantigen, such as MuSK or a fragment thereof, without HLA restriction.

In one embodiment, the nucleic acid sequence of the signaling domain comprises a nucleic acid sequence encoding a CD3 zeta signaling domain. In another embodiment, the nucleic acid sequence of the CD3 zeta signaling domain encodes an amino acid sequence comprising: RVKFSRS-ADAPAYQQGQNQLYNELNLGRREEYDVLDKRR-GRDPEMGGKPRRK NPQEGLYNELQKDKMAEAYSEI-GMKGERRRGKGHDGLYQGLSTATKDTYDAL HMQALPPR (SEQ ID NO: 15). In another embodiment, the nucleic acid sequence encoding the CD3 zeta signaling domain comprises:

(SEQ ID NO: 8)
AGAGTAAAGTTCAGTAGGTCCGCCGATGCCCCAGCCTATCAACAGGGGC

AAAATCAACTCTACAACGAACTTAATCTGGGACGCCGAGAGGAGTACGA

TGTCTTGGATAAGAGACGCGGCAGGGACCCTGAAATGGGCGGAAAGCCA

AGACGGAAGAACCCCCAGGAAGGTCTGTACAATGAACTTCAGAAAGATA

AGATGGCCGAAGCCTACAGCGAGATCGGCATGAAAGGAGAGAGGCGCCG

CGGCAAAGGGCATGATGGACTGTATCAGGGTCTCAGTACTGCTACTAAG

GACACATATGATGCCCTCCACATGCAGGCCCTGCCACCAAGGTGA;
or (SEQ ID NO: 20)
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCCTTCACATGCAGGCCCTGCCCCCTCGC.

In some embodiments, the CD3 zeta signaling domain comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 15. In other embodiments, the CD3 zeta signaling domain is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a nucleic acid sequence selected from the group consisting of SEQ ID NOs: 8 and 20.

Other Domains

In some embodiments, the MuSK CAAR and the polynucleotide encoding the MuSK CAAR comprise a human T cell surface glycoprotein CD8 alpha chain signal peptide. The human CD8 alpha signal peptide is responsible for the translocation of the receptor to the T cell surface.

In other embodiments, the MuSK CAAR and the polynucleotide encoding the MuSK CAAR comprise an IgG signal peptide. In some embodiments, the IgG signal peptide is encoded by a nucleic acid sequence comprising: ATG-GAGTTTGGGCTGAGCTGGCTTTTTCTTGTGGCTAT-TTTAAAAGGTGTCCA GTGC (SEQ ID NO: 2). In other embodiments, the IgG signal peptide comprises an amino acid sequence of MEFGLSWLFLVAILKGVQC (SEQ ID NO: 10). In some embodiments, the IgG signal peptide is encoded by a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 2. In some embodiments, the IgG signal peptide comprises an amino acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 10.

In one embodiment, the polynucleotide encoding the MuSK CAAR comprises a nucleic acid sequence of a peptide linker. In another embodiment, the MuSK CAAR comprises a peptide linker. In yet another embodiment, the cytoplasmic signaling sequences within the intracellular signaling domain of the MuSK CAAR can be linked to each other in a random or specified order. Optionally, a short oligo- or polypeptide linker, for example, between 2 and 10 amino acids in length may form the linkage. A glycine-serine (GS) doublet is a particularly suitable linker.

In some embodiments, the CAAR comprises a transmembrane domain and/or a cytoplasmic (intracellular) domain from a killer immunoglobulin-like receptor (KIR) family protein. The KIR gene family has at least 15 gene loci (KIR2DL1, KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3) and two pseudogenes (KIR2DP1 and KIR3DP1) encoded within a 100-200 Kb region of the Leukocyte Receptor Complex (LRC) located on chromosome 19 (19q13.4). The LRC constitutes a large, 1 Mb, and dense cluster of rapidly evolving immune genes which contains genes encoding other cell surface molecules with distinctive Ig-like extracellular domains. In addition, the extended LRC contains genes encoding the transmembrane adaptor molecules DAP10 and DAP12. Thus, a cell comprising the CAAR of the invention comprising a KIR transmembrane domain and/or cytoplasmic domain may also comprise a polynucleotide encoding DAP10 or DAP12. In certain embodiments, the KIR is KIRS2 or KIR2DS2.

Vector Comprising the MuSK CAAR

In one aspect, the invention includes a vector comprising a polynucleotide encoding a chimeric autoantibody receptor (CAAR), wherein the polynucleotide comprises a nucleic acid sequence encoding an extracellular domain comprising a human MuSK autoantigen or fragment thereof, and optionally, a transmembrane domain, and/or an intracellular signaling domain. In some embodiments, the vector comprises any of the nucleic acid sequences encoding the CAAR as described herein. The present invention also provides a vector in which DNA encoding a CAAR of the present invention is inserted.

The nucleic acid can be cloned into any number of different types of vectors. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In some embodiments, the vector comprises a plasmid vector, viral vector, retrotransposon (e.g., piggyback, sleeping beauty), site directed insertion vector (e.g., CRISPR, Zinc finger nucleases, TALEN), or suicide expression vector, or other known vector in the art. In some embodiments, the vector is a RNA vector.

In some embodiments, the vector is a viral vector, such as a lentiviral vector.

Viral vector technology is well known in the art and is described, for example, in Sambrook et al., 2012, MOLECULAR CLONING: A LABORATORY MANUAL, volumes 1-4, Cold Spring Harbor Press, N.Y.), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Viral vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

In some embodiments, the vector is a 3rd generation lentiviral vector. In some embodiments, a $3^{rd}$ generation self-inactivating lentiviral vector plasmid can be used in which the expression of the CAR is regulated by the human elongation factor 1 alpha promoter. This results in stable (permanent) expression of the CAR in the host cell, e.g., host T cell. As an alternative approach, the encoding mRNA can be electroporated into the host cell, which would achieve the same therapeutic effect as the virally transduced host cell, but would not be permanent because the mRNA would dilute out with cell division.

In some embodiments, the vector is a transposon-based expression vector. A "transposon" or "transposable element" is a DNA sequence that can change its position within a genome. There are two distinct types of transposon: class II transposons, which consist of DNA that moves directly from place to place; and class I transposons, which are retrotransposons that first transcribe the DNA into RNA and then use reverse transcriptase to make a DNA copy of the RNA to insert in a new location. In a transposon system, a transcriptional unit, e.g., including the nucleic acid sequence encoding the CAAR, is flanked by terminal repeat sequences of a transposon. Transposons typically interact with a transposase, which recognizes the terminal repeat sequences and mediates the movement of the transposon. A transposase can, for example, be co-delivered as a protein, encoded on the same vector as the CAAR, or encoded on a separate vector. Non-limiting examples of transposon/transposase systems include Sleeping Beauty, Piggybac, Frog Prince, and Prince Charming. The expression of natural or synthetic polynucleotides encoding CAARs is typically achieved by operably linking a nucleic acid encoding the CAAR polypeptide or portions thereof to a promoter (e.g., EF1alpha promoter), and incorporating the construct into an expression vector.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1a promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence, which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, an inducible promoter is activated in response to an extracellular ligand. For example, in some embodiments, the inducible promoter is activated (and the expression of the CAAR is regulated) by an extracellular ligand binding to a synthetic receptor. For example, in some embodiments, a synthetic receptor, e.g., a synthetic Notch receptor (i.e., "synNotch") may be employed as a binding-triggered transcriptional switch that, when bound to its ligand, activates a promoter to which a nucleic acid sequence encoding the CAAR is operably linked. Accordingly, as a non-limiting example, such systems may require the presence of a ligand (e.g., to which the synNotch binds) for the immune cell to be responsive to a BCR or autoantibody (e.g., to which the CAAR binds). The requirement of particular combinations to generate certain signaling outputs in molecular circuits results in a logic gate. See, for example, Roybal et al., 2016 Cell 164(4):770-9.

Examples of other systems for expressing or regulating expression of a chimeric receptor include those described in Wu et al. (2015) Science 350: aab4077; Fedorov et al. (2014) Cancer Journal 20:160-165; Kloss et al. (2013) Nature Biotechnology 31: 71-75; Sakemura et al. (2016) Cancer Immunol. Res. 4:658-668; Hill et al. (2018) Nature Chemical Biology 14:112-117; Di Stasi et al. (2011) N. Engl. J. Med. 365:1673-1683; Budde et al. (2013) PLoS One 8: e82742; Wei et al. (2012) Nature 488: 384-388; Ma et al. (2016) Proc. Natl. Acad. Sci. USA 113: E450-458; Rodgers et al. (2016) Proc. Natl. Acad. Sci. USA 113: E459-468; Kudo et al. (2014) Cancer Res. 74: 93-103, and Chen et al. (2010) Proc. Natl. Acad. Sci. USA 107, 8531-8536.

Expression of the CAAR protein may be verified using immunoblot, immunohistochemistry, flow cytometry or other technology well known and available in the art. In a preferred embodiment, expression the CAAR is verified by flow cytometry. In order to assess the expression of a CAAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, N.Y.).

Biological methods for introducing a polynucleotide of interest into a host cell include the use of DNA and RNA vectors. RNA vectors include vectors having a RNA promoter and/or other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g. an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances, which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham. AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Any domains and/or fragments of the CAAR, vector, and the promoter may be synthesized gene fragments amplified by PCR or any other means known in the art.

Cells Comprising the CAAR

In another aspect, the invention includes a genetically modified cell comprising the MuSK chimeric autoantibody receptor (CAAR) disclosed herein.

In another embodiment, the genetically modified cell expresses the MuSK CAAR. In this embodiment, the cell has high affinity for MuSK autoantibody-based B cell receptors (BCRs) on B cells or on B cells that have differentiated into plasma cells. As a result, the genetically modified cell can induce direct killing of anti-MuSK B cells or indirect killing of plasma cells expressing MuSK autoantibodies. In yet another embodiment, the genetically modified cell has low affinity for antibodies bound to an Fc receptor.

In one embodiment, the genetically modified cell is a T cell, such as a helper T cell, a cytotoxic T cell, a memory T cell, regulatory T cell, gamma delta, T cell, a natural killer cell, cytokine induced killer cell, a cell line thereof, a T memory stem cell, or other T effector cell. It is also useful for the T cell to have limited toxicity toward healthy cells and specificity to cells expressing autoantibodies. Such specificity prevents or reduces off-target toxicity that is prevalent in current therapies that are not specific for autoantibodies. In one embodiment, the T cell has limited toxicity toward healthy cells. In one embodiment the T cell is an autologous cell. In another embodiment, the T cell is an allogeneic cell.

In some embodiments, the invention include genetically modified immune cells derived from pluripotent stem cells that were differentiated in vitro. In other embodiments, the invention includes T cells, such as primary cells, expanded T cells derived from primary T cells, T cells derived from stem cells differentiated in vitro, T cell lines such as Jurkat cells, other sources of T cells, combinations thereof, and other effector cells. For example, a transduced Jurkat cell line with a NFAT response element followed by GFP can be used to detect and isolate MuSK specific B cells and to clone the MuSK specific antibody repertoire in a comprehensive and unbiased fashion. The interacting B and Jurkat cells can be detected as GFP positive doublets or multimers and sorted by flow cytometry. Expression cloning of the B cell receptor encoding genes will provide further information on how autoimmunity and autoantibodies in autoantibody mediated neuromuscular junction (NMJ) diseases, such as myasthenia gravis (MG).

The functional ability of CAARs to bind to autoantibodies and sera, for example, but not limited to, MG sera, can be assessed in a Jurkat reporter cell line, which depends on activation of the CAAR by binding to autoantibody (in response to which the activated cells fluorescence green due to an NFAT-GFP reporter construct contained therein). Such methods are useful and reliable qualitative measures for functional binding ability. The proper processing of the autoantigen on the cell surface is also important and can be measured using monoclonal antibodies. Furthermore, truncations or mutations of MuSK based on major disease epitopes are also useful and included herein. Truncated versions using a different length hinge region are also useful. With regard to safety, preventing or reducing possible homophilic and heterophilic interactions and activation (e.g., MuSK—LRP4) between the transduced cells or toward the neuromuscular junction is preferred.

Further assessment of efficacy and safety of the CAAR can be performed, for example, as follows:

Constructs can be transiently transfected into human cells, such as 293T/17. The surface expression can be detected with monoclonal antibodies (either IgG or ScFv) specific for the abovementioned extracellular domains (Ig1, Ig2, Ig3, Fz (Ig-like domains and frizzled domain)) the linker between the domains, or other structure included in the CAAR. Binding can be verified with specific secondary antibodies and quantified by flow cytometry.

Production of membrane expressed constructs of human anti-MuSK antibodies of any isotype can serve as target cells for testing the different MuSK-CAARs. Additional target cell lines can be produced as needed by expression of human monoclonal antibodies on the surface of cell lines (e.g., Nalm6 or K562 cells).

Autoimmune Diseases

The present invention also provides methods for preventing, treating and/or managing a disorder or autoimmune disease associated with autoantibody-expressing cells in the context of an autoantibody-mediated neuromuscular junction (NMJ) disease. The methods comprise administering to a subject in need thereof a genetically modified cell, e.g., T cell, comprising the CAAR of the invention that binds to the autoantibody-expressing cell. In one aspect, the subject is a human. Non-limiting examples of an autoantibody-mediated NMJ disease include but are not limited to myasthenia gravis (MG).

The cells of the invention to be administered may be autologous, allogeneic or xenogeneic with respect to the subject undergoing therapy. In the methods of treatment, cells, e.g., T cells, isolated from a subject can be modified to express the appropriate CAAR, expanded ex vivo and then reinfused into the same subject (e.g., the cells are autologous cells). In some embodiments the cells, e.g., T cells, are reinfused into a different subject than the original cells' donor (e.g., the cells are allogeneic cells). The modified cells, e.g., T cells, recognize target cells, such as MuSK autoantibody producing B cells or plasma cells, and become activated, resulting in killing of the autoimmune target cells.

Relapse may also occur in patients with an autoimmune disease, for example in MG patients. In patients treated with drugs (e.g., prednisone or rituximab), the relapse may be mediated by persistence of the same autoantibody B cell clones, whereas remission is associated with disappearance of these clones. By infusing MuSK CAAR cells, e.g., T cells, the autoimmune cells are depleted to induce long-term remission, possibly due to the longevity of the MuSK CAAR cells, e.g., T cells and/or autoantigen-reactive clones do not re-appear.

To monitor MuSK CAAR-expressing cells in vitro, in situ, or in vivo, MuSK CAAR cells can further express a detectable marker. When the MuSK CAAR binds the target, the detectable marker is activated and expressed, which can be detected by assays known in the art, such as flow cytometry. In one embodiment, the MuSK CAAR includes a NFAT response element and a detectable marker, such as a green fluorescent protein (GFP), to detect and quantify MuSK CAAR expressing cells.

Sources of T Cells

Prior to genetic modification and/or expansion, T cells (e.g., autologous or allogeneic T cells) are obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, and spleen tissue. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL' gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For some patients, use of longer incubation times, such as 24 hours, can increase cell yield. Longer incubation times may be used to isolate T cells in any situation where there are few T cells as compared to other cell types, such as isolating T cells from immunocompromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^+$, $GITR^+$, and $FoxP3^+$. Alternatively, in certain embodiments, T regulatory cells are depleted by anti-CD25 conjugated beads or other similar method of selection. In other embodiments, subpopulation of T cells, such as, but not limited to, cells positive or expressing high levels of one or more surface markers e.g., CD28+, CD8+, CCR7+, CD27+, CD127+, CD45RA+, and/or CD45RO+ T cells, can be isolated by positive or negative selection techniques.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as, but not limited to, rituximab or other anti-CD20 or anti-CD19 agents, anti-FcRn agents, Btk inhibitors, plasmapheresis, corticosteroids, mycophenolate, azathioprine, methotrexate, cyclosporine, cyclophosphamide. These drugs may, for example, inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before or simultaneous to ablative therapy such as fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

In some embodiments, T cells are activated and expanded, for example, using methods as described in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. In other embodiments, T cells are activated, but not expanded, or are neither activated nor expanded prior to use.

When activated and expanded, the T cells of the invention are generally expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD8^+$ T cell expansion and T cell growth is used. In one embodiment, a 1:1 ratio of each antibody bound to the beads for CD4⁺ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment, an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments, the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment, the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8⁺ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention, the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_C$ cells or $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Applications

In one aspect, the invention includes a method for treating an autoantibody-mediated NMJ disease in a subject. The method comprises: administering to the subject an effective amount of a genetically modified cell, e.g., T cell, comprising a polynucleotide encoding a chimeric autoantibody receptor (CAAR), wherein the polynucleotide encodes a muscle-specific kinase (MuSK) autoantigen or fragment thereof, and optionally, a transmembrane domain, an intracellular domain of a costimulatory molecule, and/or a signaling domain, thereby treating the autoantibody-mediated NMJ disease in the subject. In some embodiments, the polynucleotide further encodes a KIR element.

In another aspect, the invention includes a method for preventing or reducing NMJ damage in a subject at risk or suffering from an autoantibody-mediated NMJ disease. The method comprises: administering to the subject an effective amount of a genetically modified cell, e.g., T cell, comprising a polynucleotide encoding a CAAR, wherein the polynucleotide encodes a MuSK autoantigen or fragment thereof, and optionally, a transmembrane domain, an intracellular domain of a costimulatory molecule, and/or a signaling domain, thereby preventing or reducing NMJ damage in the subject. In some embodiments, the polynucleotide further encodes a KIR element.

In one embodiment, the autoantibody-mediated NMJ disease is myasthenia gravis (MG). In another embodiment, the subject is a human.

Without wishing to be bound by any particular theory, the anti-autoantibody immune response elicited by the CAAR-modified cells, e.g., T cells may be an active or a passive immune response. In yet another embodiment, the modified cell, e.g., T cell targets a B cell. For example, autoantibody-expressing B cells may be susceptible to indirect destruction by CAAR-redirected cells, e.g., T cells, that have previously reacted against adjacent autoantibody-expressing cells.

In one embodiment, the genetically modified cells, e.g., T cells of the invention are modified by a fully-human CAAR.

In one embodiment, the fully-human CAAR-genetically modified cells, e.g., T cells may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing to the cells a polynucleotide encoding a CAAR iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAAR disclosed herein. The CAAR-modified cell can be administered to a mammalian recipient to provide a therapeutic benefit. The mammalian recipient may be a human and the CAAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also includes compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the MuSK CAAR-modified cells, e.g., T cells of the invention are used in the treatment of diseases, disorders and conditions associated with expression of autoantibodies. In certain embodiments, the cells of the invention are used in the treatment of patients at risk for developing autoimmune NMJ diseases, disorders and conditions associated with expression of autoantibodies. Thus, the present invention provides methods for the treatment or prevention of autoimmune NMJ diseases, disorders and conditions associated with expression of autoantibodies (anti-MuSK) comprising administering to a subject in need thereof, a therapeutically effective amount of the CAAR-modified cells, e.g., T cells of the invention.

The CAAR-modified cells, e.g., T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-autoantibody effective amount," "an anti-BCR effective amount," "an autoimmune disease-inhibiting effective amount," or "therapeutic amount" is indicated, the precise amount of the compositions of the present invention to be administered can be determined by a physician with consideration of individual differences in age, weight, and condition of the patient (subject). It can generally be stated that a pharmaceutical composition comprising the cells, e.g., T cells described herein may be administered at a dosage of $10^4$ to $10^9$ cells/kg body weight, in some instances $10^5$ to $10^6$ cells/kg body weight, including all integer values within those ranges. Cell, e.g., T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, activated cells, e.g., T cells, are administered to a subject. Subsequent to administration, blood is redrawn or apheresis is performed, and cells, e.g., T cells, are activated and expanded therefrom using the methods described here, and are then reinfused back into the patient. This process can be carried out multiple times every few weeks. In certain embodiments, cells, e.g., T cells, can be activated from blood draws of from 10cc to 400cc. In certain embodiments, cells, e.g., T cells are activated from blood draws of 20cc, 30cc, 40cc, 50cc, 60cc, 70cc, 80cc, 90cc, or 100cc. Not to be bound by theory, using this multiple blood draw/multiple reinfusion protocol, may select out certain populations of cells, e.g., T cells.

The cells of the invention to be administered may be autologous, allogeneic or xenogeneic with respect to the subject undergoing therapy.

Administration of the cells of the invention may be carried out using any convenient means, including by aerosol inhalation, injection, ingestion, transfusion, implantation or transplantation. The compositions described herein may be administered to a patient transarterially, subcutaneously, intradermally, intranodally, intramedullary, intramuscularly, by intravenous (i.v.) injection, or intraperitoneally. In one embodiment, the cell, e.g., T cell, compositions of the present invention are administered to a patient by intradermal or subcutaneous injection. In another embodiment, the cell, e.g., T cell, compositions of the present invention are administered by i.v. injection. The compositions of cells, e.g., T cells, may be injected directly into a lymph node, or site of pathophysiologic activity.

In certain embodiments of the present invention, cells activated and expanded using the methods described herein, or other methods known in the art where cells, e.g., T cells, are expanded to therapeutic levels, are administered to a patient in conjunction with (e.g., before, simultaneously or following) any number of relevant treatment modalities, including but not limited to treatment with agents such as antiviral therapy, cidofovir, interleukin-2, Cytarabine (also known as ARA-C), rituximab (or any other generalized B cell depleting agent such as Btk inhibitors or other anti-CD20/CD19 or B cell targeting agents) and/or Soliris® (eculizumab, a terminal complement inhibitor). In further embodiments, the cells, e.g., T cells, of the invention may be used in combination with an antibody anti-FcRn, IVIg, or plasmapheresis in order to reduce the anti-MuSK antibody concentration before therapy. In yet other embodiments, a mild lymphodepletion regimen (e.g., Low-dose fludarabine or Cytoxan) might precede treatment with the cells, e.g., T cells, of the invention.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances smaller or larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Figure 3A:
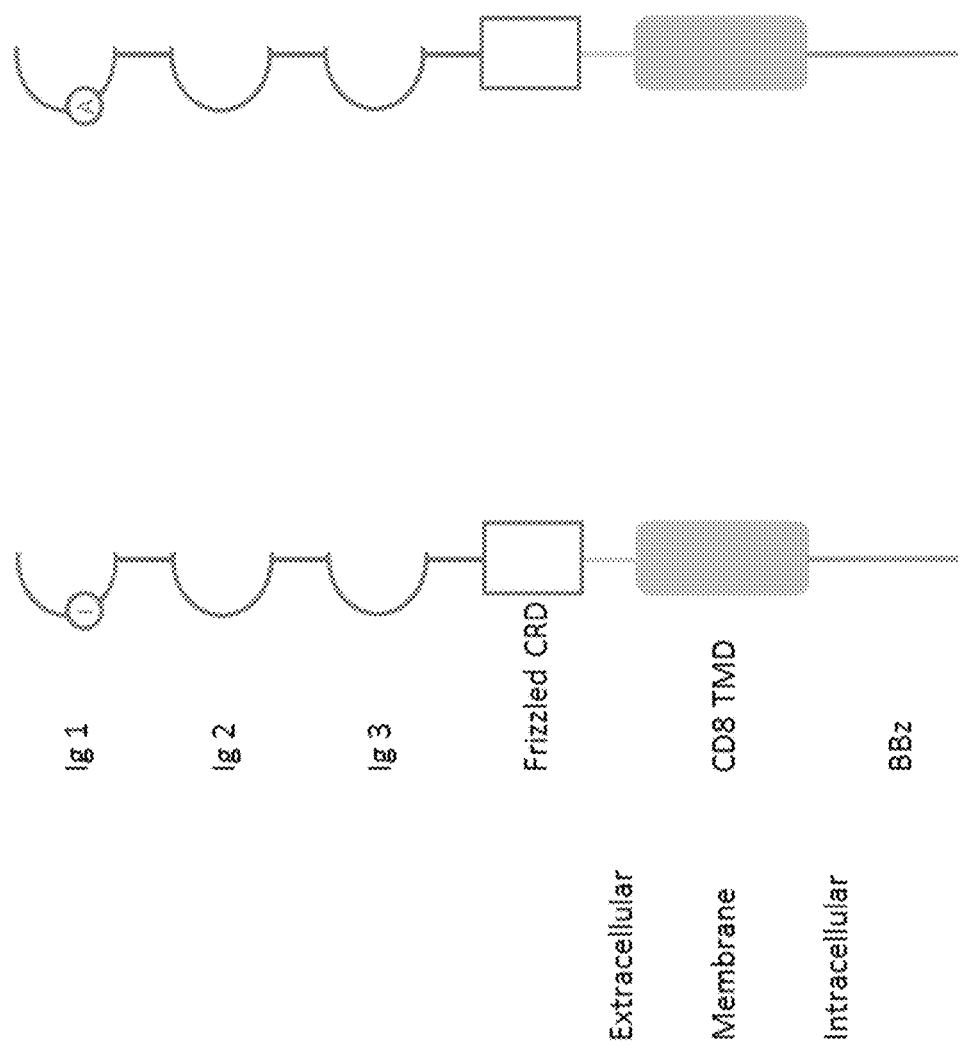
FIGS. 3A-3B are a series of images showing exemplary MuSK CAAR constructs.
Figure 4A:
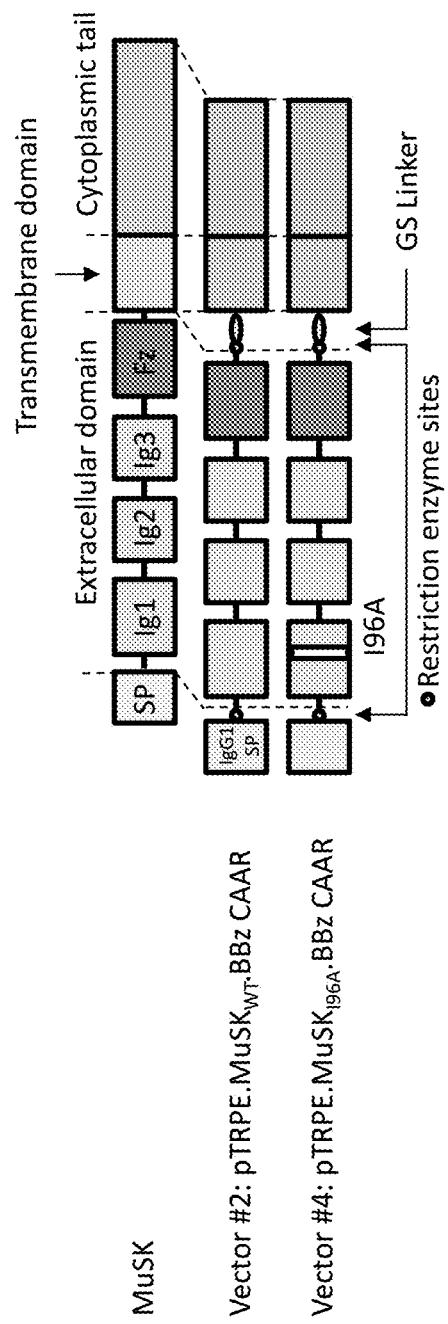
FIGS. 4A-4B illustrate MuSK CAAR constructs and show that CAAR-T cells successfully express MuSK wt and MuSK I96A extracellular domain (ECD) on the cell surface.
Figure 14:
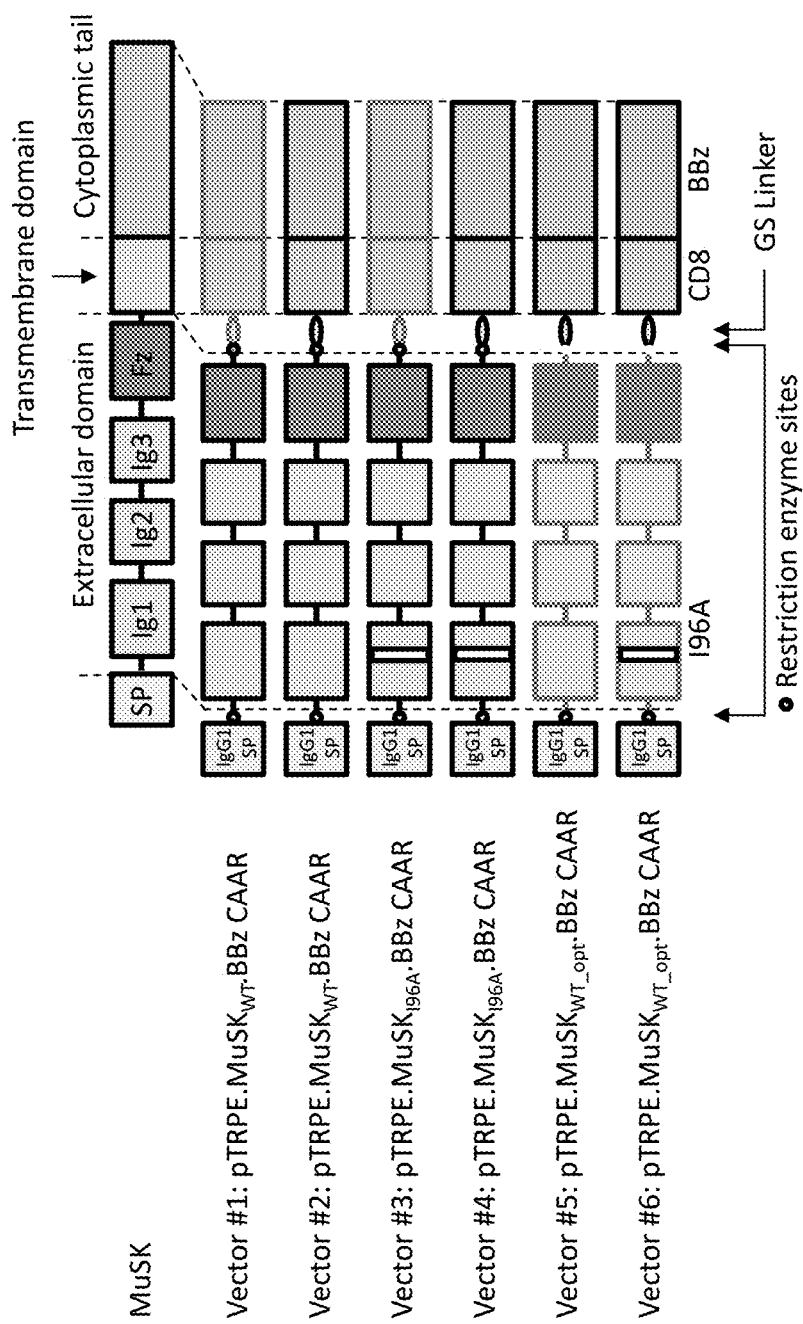
FIG. 14 is a schematic diagram of MuSK wt/I96A CAARs. Codon-optimized domains are indicated as a light gray colored-box. All the experiments described herein, except for those shown in FIGS. 15 and 16 were conducted using Vector #2 (pTRPE.MuSK$_{WT}$.BBz CAAR) and Vector #4 (pTRPE.MuSK$_{I96A}$.BBz CAAR). Vector #5 (pTRPE.MuSK$_{WT\_opt}$.BBz CAAR) and Vector #6 (pTRPE.MuSK$_{WT\_opt}$.BBz CAAR) were used for FIGS. 15 and 16. Vector #5 and Vector #6 have no restriction enzyme site between the extracellular domain and the GS Linker (indicated as a white dot without outline).

-MuSK CAAR constructs (as illustrated in FIGS. 3A, 4A, and 14)
Vector #1: pTRPE.MuSK$_{WT}$.BBz CAAR (Nucleic acid Sequence, SEQ ID NO: 1).

(SEQ ID NO: 1)
*ATGGAGTTTGGGCTGAGCTGGCTTTTTCTTGTGGCTATTTTAAAAGGTGTCCAGTG*

CGGATCC<u>CTTCCAAAAGCTCCTGTCATCACCACTCCTCTTGAAACAGTGG</u>

<u>ATGCCTTAGTTGAAGAAGTGGCTACTTTCATGTGTGCAGTGGAATCCTAC</u>

-continued

```
CCCCAGCCTGAGATTTCCTGGACTAGAAATAAAATTCTCATTAAACTCTT

TGACACCCGGTACAGCATCCGGGAGAATGGGCAGCTCCTCACCATCCTG

AGTGTGGAAGACAGTGATGATGGCATTTACTGCTGCACGGCCAACAATG

GTGTGGGAGGAGCTGTGGAGAGTTGTGGAGCCCTGCAAGTGAAGATGA

AACCTAAAATAACTCGCCCTCCCATAAATGTGAAAATAATAGAGGGATTA

AAAGCAGTCCTACCATGTACTACAATGGGTAATCCCAAACCATCAGTGTC

TTGGATAAAGGGAGACAGCCCTCTCAGGGAAAATTCCCGAATTGCAGTT

CTTGAATCTGGGAGCTTGAGGATTCATAACGTACAAAAGGAAGATGCAG

GACAGTATCGATGTGTGGCAAAAAACAGCCTCGGGACAGCATATTCCAA

AGTGGTGAAGCTGGAAGTTGAGGTTTTTGCCAGGATTCTGCGGGCTCCT

GAATCCCACAATGTCACCTTTGGCTCCTTTGTGACCCTGCACTGTACAGC

AACAGGCATTCCTGTCCCCACCATCACCTGGATTGAAAACGGAAATGCT

GTTTCTTCTGGGTCCATTCAAGAGAGTGTGAAAGACCGAGTGATTGACT

CAAGACTGCAGCTGTTTATCACCAAGCCAGGACTCTACACATGCATAGC

TACCAATAAGCATGGGGAGAAGTTCAGTACTGCCAAGGCTGCAGCCACC

ATCAGCATAGCAGAATGGAGTAAACCACAGAAAGATAACAAAGGCTACT

GCGCCCAGTACAGAGGGGAGGTGTGTAATGCAGTCCTGGCAAAAGATGC

TCTTGTTTTTCTCAACACCTCCTATGCGGACCCTGAGGAGGCCCAAGAG

CTACTGGTCCACACGGCCTGGAATGAACTGAAAGTAGTGAGCCCAGTCT

GCCGGCCAGCTGCTGAGGCTTTGTTGTGTAACCACATCTTCCAGGAGTG

CAGTCCTGGAGTAGTGCCTACTCCTATTCCCATTTGCAGAGAGTACTGCT

TGGCAGTAAAGGAGCTCTTCTGCGCAAAAGAATGGCTGGTAATGGAAGA

GAAGACCCACAGAGGACTCTACAGATCCGAGATGCATTTGCTGTCCGTG

CCAGAATGCAGCAAGCTTCCCAGCATGCATTGGGACCCCACGGCCTGTG

CCAGACTGCCACATCTAGATTATAACAAAGAAAACCTAAAAACATTCCCA

CCAATGACGTCCTCAAAGCCAAGTGTGGACATTCCAAATCTGCCTTCCTC

CTCCTCTTCTTCCTTCTCTGTCTCACCTACATACTCCATGACTGCTAGCGG

AGGTGGAGGTAGTGGCGGTGGAGGCAGCTCTGGTATCTACATCTGGGCACC

CTTGGCTGGAACATGCGGGGTCCTGCTGCTGAGCTTGGTGATCACCCTT

TACTGCAAGCGCGGTCGCAAGAAACTGCTCTATATTTTTAAACAGCCATTCA

TGAGACCTGTCCAGACCACTCAAGAGGAGGACGGATGTTCCTGTAGATTTCC

TGAAGAGGAAGAGGGGGGTGCGAGCTGAGAGTAAAGTTCAGTAGGTCCGCC

GATGCCCCAGCCTATCAACAGGGGCAAAATCAACTCTACAACGAACTTAATCTG

GGACGCCGAGAGGAGTACGATGTCTTGGATAAGAGACGCGGCAGGGACCCTG

AAATGGGCGGAAAGCCAAGACGGAAGAACCCCCAGGAAGGTCTGTACAATGAA

CTTCAGAAAGATAAGATGGCCGAAGCCTACAGCGAGATCGGCATGAAAGGAGA
```

-continued

GAGGCGCCGCGGCAAAGGGCATGATGGACTGTATCAGGGTCTCAGTACTGCTA

CTAAGGACACATATGATGCCCTCCACATGCAGGCCCTGCCACCAAGGTGA

IgG Signal peptide: 1-57 (SEQ ID NO: 2)
MuSK ECD: 64-1479 (SEQ ID NO: 3)
GS Linker (codon optimized): 1486-1515 (SEQ ID NO: 4)
CD8 TMD (codon optimized): 1522-1593 (SEQ ID NO: 5)
4-1BB domain (codon optimized): 1594-1719 (SEQ ID NO: 7)
CD3zeta domain (codon optimized): 1720-2055 (SEQ ID NO: 8)
Stop codon: 2056-2058

Vector #1: pTRPE.MuSK$_{WT}$.BBz CAAR (Amino acid Sequence, SEQ ID NO: 9).

(SEQ ID NO: 9)
MEFGLSWLFLVAILKGVQCGSLPKAPVITTPLETVDALVEEVATFMCAVESYPQ

PEISWTRNKILIKLFDTRYSIRENGQLLTILSVEDSDDGIYCCTANNGVGGAV

ESCGALQVKMKPKITRPPINVKIIEGLKAVLPCTTMGNPKPSVSWIKGDSPL

RENSRIAVLESGSLRIHNVQKEDAGQYRCVAKNSLGTAYSKVVKLEVEVFAR

ILRAPESHNVTFGSFVTLHCTATGIPVPTITWIENGNAVSSGSIQESVKDRVID

SRLQLFITKPGLYTCIATNKHGEKFSTAKAAATISIAEWSKPQKDNKGYCAQ

YRGEVCNAVLAKDALVFLNTSYADPEEAQELLVHTAWNELKVVSPVCRPAA

EALLCNHIFQECSPGVVPTPIPICREYCLAVKELFCAKEWLVMEEKTHRGLY

RSEMHLLSVPECSKLPSMHWDPTACARLPHLDYNKENLKTFPPMTSSKPSV

DIPNLPSSSSSSFSVSPTYSMTASGGGGSGGGGSSGIYIWAPLAGTCGVLLLSLV

ITLYCKRGRKKLLYIFKQPFMRPVQTTQEEDGCSCRFPEEEEGGCELRVKFSRSA

DAPAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR

IgG Signal peptide: 1-19 (SEQ ID NO: 10)
MuSK ECD: 22-493 (SEQ ID NO: 11)
GS Linker: 496-505 (SEQ ID NO: 12)
CD8 TMD: 508-531 (SEQ ID NO: 13)
4-1BB domain: 532-573 (SEQ ID NO: 14)
CD3zeta domain: 574-685 (SEQ ID NO: 15)

Vector #2: pTRPE.MuSK$_{WT}$.BBz CAAR Nucleotide Sequence (Nucleic acid Sequence, SEQ ID NO: 16)

(SEQ ID NO: 16)
ATGGAGTTTGGGCTGAGCTGGCTTTTTCTTGTGGCTATTTTAAAAGGTGTCCAGTG

CGGATCCCTTCCAAAAGCTCCTGTCATCACCACTCCTCTTGAAACAGTGG

ATGCCTTAGTTGAAGAAGTGGCTACTTTCATGTGTGCAGTGGAATCCTAC

CCCCAGCCTGAGATTTCCTGGACTAGAAATAAAATTCTCATTAAACTCTT

TGACACCCGGTACAGCATCCGGGAGAATGGGCAGCTCCTCACCATCCTG

AGTGTGGAAGACAGTGATGATGGCATTTACTGCTGCACGGCCAACAATG

GTGTGGGAGGAGCTGTGGAGAGTTGTGGAGCCCTGCAAGTGAAGATGA

AACCTAAAATAACTCGCCCTCCCATAAATGTGAAAATAATAGAGGGATTA

AAAGCAGTCCTACCATGTACTACAATGGGTAATCCCAAACCATCAGTGTC

-continued

TTGGATAAAGGGAGACAGCCCTCTCAGGGAAAATTCCCGAATTGCAGTT

CTTGAATCTGGGAGCTTGAGGATTCATAACGTACAAAAGGAAGATGCAG

GACAGTATCGATGTGTGGCAAAAAACAGCCTCGGGACAGCATATTCCAA

AGTGGTGAAGCTGGAAGTTGAGGTTTTTGCCAGGATTCTGCGGGCTCCT

GAATCCCACAATGTCACCTTTGGCTCCTTTGTGACCCTGCACTGTACAGC

AACAGGCATTCCTGTCCCCACCATCACCTGGATTGAAAACGGAAATGCT

GTTTCTTCTGGGTCCATTCAAGAGAGTGTGAAAGACCGAGTGATTGACT

CAAGACTGCAGCTGTTTATCACCAAGCCAGGACTCTACACATGCATAGC

TACCAATAAGCATGGGAGAAGTTCAGTACTGCCAAGGCTGCAGCCACC

ATCAGCATAGCAGAATGGAGTAAACCACAGAAAGATAACAAAGGCTACT

GCGCCCAGTACAGAGGGGAGGTGTGTAATGCAGTCCTGGCAAAAGATGC

TCTTGTTTTTCTCAACACCTCCTATGCGGACCCTGAGGAGGCCCAAGAG

CTACTGGTCCACACGGCCTGGAATGAACTGAAAGTAGTGAGCCCAGTCT

GCCGGCCAGCTGCTGAGGCTTTGTTGTGTAACCACATCTTCCAGGAGTG

CAGTCCTGGAGTAGTGCCTACTCCTATTCCCATTTGCAGAGAGTACTGCT

TGGCAGTAAAGGAGCTCTTCTGCGCAAAAGAATGGCTGGTAATGGAAGA

GAAGACCCACAGAGGACTCTACAGATCCGAGATGCATTTGCTGTCCGTG

CCAGAATGCAGCAAGCTTCCCAGCATGCATTGGGACCCCACGGCCTGTG

CCAGACTGCCACATCTAGATTATAACAAAGAAAACCTAAAAACATTCCCA

CCAATGACGTCCTCAAAGCCAAGTGTGGACATTCCAAATCTGCCTTCCTC

CTCCTCTTCTTCCTTCTCTGTCTCACCTACATACTCCATGACTGCTAGCGG

TGGCGGAGGTTCTGGAGGTGGAGGTTCCTCCGGAATCTACATCTGGGCGCC

CTTGGCCGGGACTTGTGGGGTCCTTCTCCTGTCACTGGTTATCACCCTTT

ACTGCAAACGGGGCAGAAAGAAACTCCTGTATATATTCAAACAACCATTTAT

GAGACCAGTACAAACTACTCAAGAGGAAGATGGCTGTAGCTGCCGATTTCCA

GAAGAAGAAGAAGGAGGATGTGAACTGAGAGTGAAGTTCAGCAGGAGCGCA

GACGCCCCGCGTACCAGCAGGGCCAGAACCAGCTCTATAACGAGCTCAATCT

AGGACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAATG

AACTGCAGAAAGATAAGATGGCGGAGGCCTACAGTGAGATTGGGATGAAAGGC

GAGCGCCGGAGGGGCAAGGGGCACGATGGCCTTTACCAGGGTCTCAGTACAG

CCACCAAGGACACCTACGACGCCCTTCACATGCAGGCCCTGCCCCCTCGCTAA

IgG Signal peptide: 1-57 (SEQ ID NO: 2)
MuSK ECD: 64-1479 (SEQ ID NO: 3)
GS Linker: 1486-1515 (SEQ ID NO: 17)
CD8 TMD: 1522-1593 (SEQ ID NO: 18)
4-1BB domain: 1594-1719 (SEQ ID NO: 19)
*CD3zeta domain*: 1720-2055 (SEQ ID NO: 20)
Stop codon: 2056-2058

Vector #2: pTRPE.MuSK<sub>WT</sub>.BBz CAAR Amino Acid Sequence
(Amino acid
Sequence, SEQ ID NO: 9)

(SEQ ID NO: 9)

MEFGLSWLFLVAILKGVQCGSLPKAPVITTPLETVDALVEEVATFMCAVESYPQ

PEISWTRNKILIKLFDTRYSIRENGQLLTILSVEDSDDGIYCCTANNGVGGAV

ESCGALQVK1VIKPKITRPPINVKIIEGLKAVLPCTTMGNPKPSVSWIKGDSPL

RENSRIAVLESGSLRIHNVQKEDAGQYRCVAKNSLGTAYSKVVKLEVEVFAR

ILRAPESHNVTFGSFVTLHCTATGIPVPTITWIENGNAVSSGSIQESVKDRVID

SRLQLFITKPGLYTCIATNKHGEKFSTAKAAATISIAEWSKPQKDNKGYCAQ

YRGEVCNAVLAKDALVFLNTSYADPEEAQELLVHTAWNELKVVSPVCRPAA

EALLCNHIFQECSPGVVPTPIPICREYCLAVKELFCAKEWLVMEEKTHRGLY

RSEMHLLSVPECSKLPSMHWDPTACARLPHLDYNKENLKTFPPMTSSKPSV

DIPNLPSSSSSSFSVSPTYSMTASGGGGSGGGGSSGIYIWAPLAGTCGVLLLSLV

ITLYCKRGRKKLLYIFKQPFMRPVQTTQEEDGCSCRFPEEEEGGCEL*RVKFSRSA*

*DAPAYQQGQNQLYNELNLGRREEYDVLDKRRGRDPEMGGKPRRKNPQEGLYNE*

*LQKDKMAEAYSEIGMKGERRRGKGHDGLYQGLSTATKDTYDALHMQALPPR*

IgG Signal peptide: 1-19 (SEQ ID NO: 10)
MuSK ECD: 22-493 (SEQ ID NO: 11)
GS Linker: 496-505 (SEQ ID NO: 12)
CD8 TMD: 508-531 (SEQ ID NO: 13)
4-1BB domain: 532-573 (SEQ ID NO: 14)
*CD3zeta domain*: 574-685 (SEQ ID NO: 15)

Vector #3: pTRPE.MuSK<sub>I964</sub>.BBz CAAR (Nucleic acid Sequence,
SEQ ID NO: 21).

(SEQ ID NO: 21)
ATGGAGTTTGGGCTGAGCTGGCTTTTTCTTGTGGCTATTTTAAAAGGTGTCCAGTG

CGGATCCCTTCCAAAAGCTCCTGTCATCACCACTCCTCTTGAAACAGTGG

ATGCCTTAGTTGAAGAAGTGGCTACTTTCATGTGTGCAGTGGAATCCTAC

CCCCAGCCTGAGATTTCCTGGACTAGAAATAAAATTCTCATTAAACTCTT

TGACACCCGGTACAGCATCCGGGAGAATGGGCAGCTCCTCACCATCCTG

AGTGTGGAAGACAGTGATGATGGCTACTGCTGCACGGCCAACAATG

GTGTGGGAGGAGCTGTGGAGAGTTGTGGAGCCCTGCAAGTGAAGATGA

AACCTAAAATAACTCGCCCTCCCATAAATGTGAAAATAATAGAGGGATTA

AAAGCAGTCCTACCATGTACTACAATGGGTAATCCCAAACCATCAGTGTC

TTGGATAAAGGGAGACAGCCCTCTCAGGGAAAATTCCCGAATTGCAGTT

CTTGAATCTGGGAGCTTGAGGATTCATAACGTACAAAAGGAAGATGCAG

GACAGTATCGATGTGTGGCAAAAAACAGCCTCGGGACAGCATATTCCAA

-continued

AGTGGTGAAGCTGGAAGTTGAGGTTTTTGCCAGGATTCTGCGGGCTCCT

GAATCCCACAATGTCACCTTTGGCTCCTTTGTGACCCTGCACTGTACAGC

AACAGGCATTCCTGTCCCCACCATCACCTGGATTGAAAACGGAAATGCT

GTTTCTTCTGGGTCCATTCAAGAGAGTGTGAAAGACCGAGTGATTGACT

CAAGACTGCAGCTGTTTATCACCAAGCCAGGACTCTACACATGCATAGC

TACCAATAAGCATGGGGAGAAGTTCAGTACTGCCAAGGCTGCAGCCACC

ATCAGCATAGCAGAATGGAGTAAACCACAGAAAGATAACAAAGGCTACT

GCGCCCAGTACAGAGGGGAGGTGTGTAATGCAGTCCTGGCAAAAGATGC

TCTTGTTTTTCTCAACACCTCCTATGCGGACCCTGAGGAGGCCCAAGAG

CTACTGGTCCACACGGCCTGGAATGAACTGAAAGTAGTGAGCCCAGTCT

GCCGGCCAGCTGCTGAGGCTTTGTTGTGTAACCACATCTTCCAGGAGTG

CAGTCCTGGAGTAGTGCCTACTCCTATTCCCATTTGCAGAGAGTACTGCT

TGGCAGTAAAGGAGCTCTTCTGCGCAAAAGAATGGCTGGTAATGGAAGA

GAAGACCCACAGAGGACTCTACAGATCCGAGATGCATTTGCTGTCCGTG

CCAGAATGCAGCAAGCTTCCCAGCATGCATTGGGACCCCACGGCCTGTG

CCAGACTGCCACATCTAGATTATAACAAAGAAAACCTAAAAACATTCCCA

CCAATGACGTCCTCAAAGCCAAGTGTGGACATTCCAAATCTGCCTTCCTC

CTCCTCTTCTTCCTTCTCTGTCTCACCTACATACTCCATGACTGCTAGCGG

AGGTGGAGGTAGTGGCGGTGGAGGCAGCTCTGGTATCTACATCTGGGCACC

CTTGGCTGGAACATGCGGGGTCCTGCTGCTGAGCTTGGTGATCACCCTT

TACTGCAAGCGCGGTCGCAAGAAACTGCTCTATATTTTTAAACAGCCATTCA

TGAGACCTGTCCAGACCACTCAAGAGGAGGACGGATGTTCCTGTAGATTTCC

TGAAGAGGAAGAGGGGGGGTGCGAGCTG*AGAGTAAAGTTCAGTAGGTCCGCC*

*GATGCCCCAGCCTATCAACAGGGGCAAAATCAACTCTACAACGAACTTAATCTG*

*GGACGCCGAGAGGAGTACGATGTCTTGGATAAGAGACGCGGCAGGGACCCTG*

*AAATGGGCGGAAAGCCAAGACGGAAGAACCCCCAGGAAGGTCTGTACAATGAA*

*CTTCAGAAAGATAAGATGGCCGAAGCCTACAGCGAGATCGGCATGAAAGGAGA*

*GAGGCGCCGCGGCAAAGGGCATGATGGACTGTATCAGGGTCTCAGTACTGCTA*

*CTAAGGACACATATGATGCCCTCCACATGCAGGCCCTGCCACCAAGGT*GA

*IgG Signal peptide:* 1-57 (SEQ ID NO: 2)
MuSK<sub>I96A</sub> ECD: 64-1479, Mutated sequence is indicated as bold italic and double underline. (SEQ ID NO: 6)
GS Linker (codon optimized): 1486-1515 (SEQ ID NO: 4)
CD8 TMD (codon optimized): 1522-1593 (SEQ ID NO: 5)
4-1BB domain (codon optimized): 1594-1719 (SEQ ID NO: 7)
*CD3zeta domain (codon optimized)*: 1720-2055 (SEQ ID NO: 8)
Stop codon: 2056-2058

Vector #3: pTRPE.MuSK<sub>196A</sub>.BBz CAAR (Amino acid Sequence, SEQ ID NO: 22).

(SEQ ID NO: 22)

*MEFGLSWLFLVAILKGVQCGS*LPKAPVITTPLETVDALVEEVATFMCAVESYPQ

PEISWTRNKILIKLFDTRYSIRENGQLLTILSVEDSDDGAYCCTANNGVGGAV

ESCGALQVKNIKPKITRPPINVKIIEGLKAVLPCTTMGNPKPSVSWIKGDSPL

RENSRIAVLESGSLRIHNVQKEDAGQYRCVAKNSLGTAYSKVVKLEVEVFAR

SRLQLFITKPGLYTCIATNKHGEKFSTAKAAATISIAEWSKPQKDNKGYCAQ

YRGEVCNAVLAKDALVFLNTSYADPEEAQELLVHTAWNELKVVSPVCRPAA

EALLCNHIFQECSPGVVPTPIPICREYCLAVKELFCAKEWLVMEEKTHRGLY

RSEMHLLSVPECSKLPSMHWDPTACARLPHLDYNKENLKTFPPMTSSKPSV

DIPNLPSSSSSSFSVSPTYSMTASGGGGSGGGGSSGIYIWAPLAGTCGVLLLSLV

ITLYCKRGRKKLLYIFKQPFMRPVQTTQEEDGCSCRFPEEEEGGCEL*RVKFSRSA*

*DAPAYQQGQNQLYNELNLGRREEYDVLDKRRGRDPEMGGKPRRKNPQEGLYNE*

*LQKDKMAEAYSEIGMKGERRRGKGHDGLYQGLSTATKDTYDALHMQALPPR*

IgG Signal peptide: 1-19 (SEQ ID NO: 10)
MuSK<sub>196A</sub> ECD: 22-493, Mutated sequence is indicated as bold italic and double underline. (SEQ ID NO: 23)
GS Linker: 496-505 (SEQ ID NO: 12)
CD8 TMD: 508-531 (SEQ ID NO: 13)
4-1BB domain: 532-573 (SEQ ID NO: 14)
CD3zeta domain: 574-685 (SEQ ID NO: 15)

Vector #4: pTRPE.MuSK<sub>196A</sub>.BBz CAAR Nucleotide Sequence
(SEQ ID NO: 24)

(SEQ ID NO: 24)

*ATGGAGTTTGGGCTGAGCTGGCTTTTTCTTGTGGCTATTTTAAAAGGTGTCCAGTG*

*CGGATCC*CTTCCAAAAGCTCCTGTCATCACCACTCCTCTTGAAACAGTGG

ATGCCTTAGTTGAAGAAGTGGCTACTTTCATGTGTGCAGTGGAATCCTAC

CCCCAGCCTGAGATTTCCTGGACTAGAAATAAAATTCTCATTAAACTCTT

TGACACCCGGTACAGCATCCGGGAGAATGGGCAGCTCCTCACCATCCTG

AGTGTGGAAGACAGTGATGATGGCGCATACTGCTGCACGGCCAACAATG

GTGTGGGAGGAGCTGTGGAGAGTTGTGGAGCCCTGCAAGTGAAGATGA

AACCTAAAATAACTCGCCCTCCCATAAATGTGAAAATAATAGAGGGATTA

AAAGCAGTCCTACCATGTACTACAATGGGTAATCCCAAACCATCAGTGTC

TTGGATAAAGGGAGACAGCCCTCTCAGGGAAAATTCCCGAATTGCAGTT

CTTGAATCTGGGAGCTTGAGGATTCATAACGTACAAAAGGAAGATGCAG

GACAGTATCGATGTGTGGCAAAAAACAGCCTCGGGACAGCATATTCCAA

AGTGGTGAAGCTGGAAGTTGAGGTTTTTGCCAGGATTCTGCGGGCTCCT

GAATCCCACAATGTCACCTTTGGCTCCTTTGTGACCCTGCACTGTACAGC

AACAGGCATTCCTGTCCCCACCATCACCTGGATTGAAAACGGAAATGCT

GTTTCTTCTGGGTCCATTCAAGAGAGTGTGAAAGACCGAGTGATTGACT

CAAGACTGCAGCTGTTTATCACCAAGCCAGGACTCTACACATGCATAGC

-continued

TACCAATAAGCATGGGGAGAAGTTCAGTACTGCCAAGGCTGCAGCCACC

ATCAGCATAGCAGAATGGAGTAAACCACAGAAAGATAACAAAGGCTACT

GCGCCCAGTACAGAGGGGAGGTGTGTAATGCAGTCCTGGCAAAAGATGC

TCTTGTTTTTCTCAACACCTCCTATGCGGACCCTGAGGAGGCCCAAGAG

CTACTGGTCCACACGGCCTGGAATGAACTGAAAGTAGTGAGCCCAGTCT

GCCGGCCAGCTGCTGAGGCTTTGTTGTGTAACCACATCTTCCAGGAGTG

CAGTCCTGGAGTAGTGCCTACTCCTATTCCCATTTGCAGAGAGTACTGCT

TGGCAGTAAAGGAGCTCTTCTGCGCAAAAGAATGGCTGGTAATGGAAGA

GAAGACCCACAGAGGACTCTACAGATCCGAGATGCATTTGCTGTCCGTG

CCAGAATGCAGCAAGCTTCCCAGCATGCATTGGGACCCCACGGCCTGTG

CCAGACTGCCACATCTAGATTATAACAAAGAAAACCTAAAAACATTCCCA

CCAATGACGTCCTAAAGCCAAGTGTGGACATTCCAAATCTGCCTTCCTC

CTCCTCTTCTTCCTTCTCTGTCTCACCTACATACTCCATGACTGCTAGCGG

TGGCGGAGGTTCTGGAGGTGGAGGTTCCTCCGGAATCTACATCTGGGCGCC

CTTGGCCGGGACTTGTGGGGTCCTTCTCCTGTCACTGGTTATCACCCTTT

ACTGCAAACGGGGCAGAAAGAAACTCCTGTATATATTCAAACAACCATTTAT

GAGACCAGTACAAACTACTCAAGAGGAAGATGGCTGTAGCTGCCGATTTCCA

GAAGAAGAAGAAGGAGGATGTGAACTGAGAGTGAAGTTCAGCAGGAGCGCA

GACGCCCCCGCGTACCAGCAGGGCCAGAACCAGCTCTATAACGAGCTCAATCT

AGGACGAAGAGAGGAGTACGATGTTTTGGACAAGAGACGTGGCCGGGACCCT

GAGATGGGGGGAAAGCCGAGAAGGAAGAACCCTCAGGAAGGCCTGTACAATG

AACTGCAGAAAGATAAGATGGCGGAGGCCTACAGTGAGATTGGGATGAAAGGC

GAGCGCCGGAGGGGCAAGGGGCACGATGGCCTTTACCAGGGTCTCAGTACAG

CCACCAAGGACACCTACGACGCCCTTCACATGCAGGCCCTGCCCCCTCGCTAA

IgG Signal peptide: 1-57 (SEQ ID NO: 2)
MuSK₁₉₆ₐ ECD: 64-1479, Mutated sequence is indicated as
bold italic and double underline (SEQ ID NO: 6)
GS Linker: 1486-1515 (SEQ ID NO: 17)
CD8 TMD: 1522-1593 (SEQ ID NO: 18)
4-1BB domain: 1594-1719 (SEQ ID NO: 19)
CD3zeta domain: 1720-2055 (SEQ ID NO: 20)
Stop codon: 2056-2058

Vector #4: pTRPE.MuSK₁₉₆ₐ.BBz CAAR Amino Acid Sequence
(SEQ ID NO: 22)
(SEQ ID NO: 22)
*MEFGLSWLFLVAILKGVQCGS*LPKAPVITTPLETVDALVEEVATFMCAVESYPQ

PEISWTRNKILIKLFDTRYSIRENGQLLTILSVEDSDDGAYCCTANNGVGGAV

ESCGALQVKMKPKITRPPINVKIIEGLKAVLPCTTMGNPKPSVSWIKGDSPL

RENSRIAVLESGSLRIHNVQKEDAGQYRCVAKNSLGTAYSKVVKLEVEVFAR

ILRAPESHNVTFGSFVTLHCTATGIPVPTITWIENGNAVSSGSIQESVKDRVID

SRLQLFITKPGLYTCIATNKHGEKFSTAKAAATISIAEWSKPQKDNKGYCAQ

YRGEVCNAVLAKDALVFLNTSYADPEEAQELLVHTAWNELKVVSPVCRPAA

EALLCNHIFQECSPGVVPTPIPICREYCLAVKELFCAKEWLVMEEKTHRGLY

RSEMHLLSVPECSKLPSMHWDPTACARLPHLDYNKENLKTFPPMTSSKPSV

DIPNLPSSSSSSFSVSPTYSMTASGGGGSGGGGSSGIYIWAPLAGTCGVLLLSLV

ITLYCKRGRKKLLYIFKQPFMRPVQTTQEEDGCSCRFPEEEEGGCEL*RVKFSRSA*

*DAPAYQQGQNQLYNELNLGRREEYDVLDKRRGRDPEMGGKPRRKNPQEGLYNE*

*LQKDKMAEAYSEIGMKGERRRGKGHDGLYQGLSTATKDTYDALHMQALPPR*

IgG Signal peptide: 1-19 (SEQ ID NO: 10)
MuSK$_{196A}$ ECD: 22-493, Mutated sequence is indicated as bold italic and double underline (SEQ ID NO: 23)
GS Linker: 496-505 (SEQ ID NO: 12)
CD8 TMD: 508-531 (SEQ ID NO: 13)
4-1BB domain: 532-573 (SEQ ID NO: 14)
CD3zeta domain: 574-685 (SEQ ID NO: 15)

Vector #5: pTRPE.MuSK$_{WT\_opt}$.BBz CAAR Nucleotide Sequence
(SEQ ID NO: 25)

(SEQ ID NO: 25)
*ATGGAGTTTGGGCTGAGCTGGCTTTTTCTTGTGGCTATTTTAAAAGGTGTCCAGTG*

CGGATCCCTTCCTAAAGCCCCGGTAATTACCACCCCATTGGAGACCGTCG

ATGCCCTTGTAGAGGAGGTTGCAACCTTTATGTGTGCTGTAGAGTCTTAC

CCGCAACCAGAGATATCATGGACCCGAAACAAGATTTTGATCAAGTTGT

TCGATACTCGATACTCCATTCGAGAGAACGGGCAGCTCCTCACTATATTG

AGCGTAGAAGACAGTGATGACGGTATATACTGCTGCACCGCTAACAATG

GTGTGGGAGGAGCAGTGGAAAGTTGTGGCGCACTTCAAGTAAAAATGAA

GCCGAAAATTACGAGACCTCCGATTAACGTTAAAATTATAGAGGGGCTG

AAAGCTGTCCTGCCATGTACCACAATGGGTAATCCCAAGCCCAGCGTAT

CCTGGATCAAAGGTGATTCACCGTTGAGAGAAAATTCTAGGATAGCGGT

ATTGGAGTCCGGCTCACTTAGAATTCACAACGTCCAAAAAGAAGATGCT

GGTCAGTACAGATGTGTCGCCAAAAATTCTCTCGGAACTGCATACAGTA

AAGTGGTAAAGCTTGAAGTTGAAGTGTTTGCAAGGATTCTGCGAGCCCC

GGAGTCACACAATGTAACCTTCGGTTCTTTTGTGACTCTTCATTGTACCG

CTACTGGAATCCCAGTTCCCACGATTACGTGGATTGAAAACGGAAATGC

CGTCTCAAGCGGCAGCATACAGGAGTCCGTGAAGGATAGAGTCATAGAC

TCCCGATTGCAACTGTTCATTACAAAGCCTGGCCTTTATACATGCATTGC

TACAAACAAGCATGGTGAGAAATTCAGTACAGCTAAGGCCGCCGCAACA

ATTTCCATTGCAGAGTGGAGCAAGCCACAAAAAGATAACAAGGGTTACT

GTGCCCAATATCGAGGGGAAGTTTGTAACGCTGTACTTGCTAAGGACGC

TCTCGTCTTCTTGAATACATCCTACGCGGACCCGGAGGAAGCCCAGGAG

CTCTTGGTGCACACTGCATGGAATGAACTTAAAGTAGTGTCCCCTGTATG

```
CCGGCCAGCCGCGGAAGCGTTGCTCTGTAATCACATTTTCCAAGAATGT

TCACCAGGGGTAGTACCAACGCCTATCCCGATATGTCGGGAATATTGTC

TGGCGGTCAAAGAGCTCTTTTGTGCTAAAGAATGGCTCGTGATGGAGGA

AAAAACTCATCGGGGTTTGTATCGCTCAGAAATGCACCTGCTGAGTGTC

CCAGAATGCTCCAAGTTGCCCAGTATGCACTGGgacCCTACGGCGTGCGC

ACGCTTGCCTCACCTGGACTACAATAAAGAAAATCTGAAAACATTTCCCC

CTATGACTAGCAGTAAGCCTTCTGTTGATATTCCAAACCTCCCGTCATCC

TCTTCATCTTCTTTCTCTGTCAGCCCGACTTATTCCATGACTGGTGGCGGA

GGTTCTGGAGGTGGAGGTTCCTCCGGAATCTACATCTGGGCGCCCTTGGCC

GGGACTTGTGGGGTCCTTCTCCTGTCACTGGTTATCACCCTTTACTGCAA

ACGGGGCAGAAAGAAACTCCTGTATATATTCAAACAACCATTTATGAGACCA

GTACAAACTACTCAAGAGGAAGATGGCTGTAGCTGCCGATTTCCAGAAGAAG

AAGAAGGAGGATGTGAACTGAGAGTGAAGTTCAGCAGGAGCGCAGACGCCCC

CGCGTACCAGCAGGGCCAGAACCAGCTCTATAACGAGCTCAATCTAGGACGAA

GAGAGGAGTACGATGTTTTGGACAAGAGACGTGGCCGGGACCCTGAGATGGG

GGGAAAGCCGAGAAGGAAGAACCCTCAGGAAGGCCTGTACAATGAACTGCAG

AAAGATAAGATGGCGGAGGCCTACAGTGAGATTGGGATGAAAGGCGAGCGCC

GGAGGGGCAAGGGGCACGATGGCCTTTACCAGGGTCTCAGTACAGCCACCAA

GGACACCTACGACGCCCTTCACATGCAGGCCCTGCCCCCTCGCTAA
```

*IgG Signal peptide*: 1-57 (SEQ ID NO: 2)
MuSK ECD (codon optimized): 64-1479 (SEQ ID NO: 26)
GS Linker: 1480-1509 (SEQ ID NO: 17)
CD8 TMD: 1515-1587 (SEQ ID NO: 18)
4-1BB domain: 1588-1713 (SEQ ID NO: 19)
*CD3zeta domain*: 1714-2049 (SEQ ID NO: 20)
Stop codon: 2050-2052

Vector #5: pTRPE.MuSK$_{WT\_opt}$.BBz CAAR Amino Acid Sequence (SEQ ID NO: 27)

(SEQ ID NO: 27)

*MEFGLSWLFLVAILKGVQCGS*LPKAPVITTPLETVDALVEEVATFMCAVESYPQ

PEISWTRNKILIKLFDTRYSIRENGQLLTILSVEDSDDGIYCCTANNGVGGAV

ESCGALQVK1VIKPKITRPPINVKIIEGLKAVLPCTTMGNPKPSVSWIKGDSPL

RENSRIAVLESGSLRIHNVQKEDAGQYRCVAKNSLGTAYSKVVKLEVEVFAR

ILRAPESHNVTFGSFVTLHCTATGIPVPTITWIENGNAVSSGSIQESVKDRVID

SRLQLFITKPGLYTCIATNKHGEKFSTAKAAATISIAEWSKPQKDNKGYCAQ

YRGEVCNAVLAKDALVFLNTSYADPEEAQELLVHTAWNELKVVSPVCRPAA

EALLCNHIFQECSPGVVPTPIPICREYCLAVKELFCAKEWLVMEEKTHRGLY

RSEMHLLSVPECSKLPSMHWDPTACARLPHLDYNKENLKTFPPMTSSKPSV

DIPNLPSSSSSSFSVSPTYSMTGGGGSGGGGSSGIYIWAPLAGTCGVLLLSLVIT

LYCKRGRKKLLYIFKQPFMRPVQTTQEEDGCSCRFPEEEEGGCEL*RVKFSRSADA*

*PAYQQGQNQLYNELNLGRREEYDVLDKRRGRDPEMGGKPRRKNPQEGLYNELQ*

*KDKMAEAYSEIGMKGERRRGKGHDGLYQGLSTATKDTYDALHMQALPPR*

IgG Signal peptide: 1-19 (SEQ ID NO: 10)
MuSK ECD: 22-493 (SEQ ID NO: 11)
GS Linker: 494-503 (SEQ ID NO: 12)
CD8 TMD: 506-529 (SEQ ID NO: 13)
4-1BB domain: 530-571 (SEQ ID NO: 14)
CD3zeta domain: 572-683 (SEQ ID NO: 15)

Vector #6: pTRPE.MuSK$_{1964\_opt}$.BBz CAAR Nucleotide Sequence
(SEQ ID NO: 28)

(SEQ ID NO: 28)

*ATGGAGTTTGGGCTGAGCTGGCTTTTTCTTGTGGCTATTTTAAAAGGTGTCCAGTG*

CGGATCCCTTCCTAAAGCCCCGGTAATTACCACCCCATTGGAGACCGTCG

ATGCCCTTGTAGAGGAGGTTGCAACCTTTATGTGTGCTGTAGAGTCTTAC

CCGCAACCAGAGATATCATGGACCCGAAACAAGATTTTGATCAAGTTGT

TCGATACTCGATACTCCATTCGAGAGAACGGGCAGCTCCTCACTATATTG

AGCGTAGAAGACAGTGATGACGGTITACTGCTGCACCGCTAACAATG

GTGTGGGAGGAGCAGTGGAAAGTTGTGGCGCACTTCAAGTAAAAATGAA

GCCGAAAATTACGAGACCTCCGATTAACGTTAAAATTATAGAGGGGCTG

AAAGCTGTCCTGCCATGTACCACAATGGGTAATCCCAAGCCCAGCGTAT

CCTGGATCAAAGGTGATTCACCGTTGAGAGAAAATTCTAGGATAGCGGT

ATTGGAGTCCGGCTCACTTAGAATTCACAACGTCCAAAAAGAAGATGCT

GGTCAGTACAGATGTGTCGCCAAAAATTCTCTCGGAACTGCATACAGTA

AAGTGGTAAAGCTTGAAGTTGAAGTGTTTGCAAGGATTCTGCGAGCCCC

GGAGTCACACAATGTAACCTTCGGTTCTTTTGTGACTCTTCATTGTACCG

CTACTGGAATCCCAGTTCCCACGATTACGTGGATTGAAAACGGAAATGC

CGTCTCAAGCGGCAGCATACAGGAGTCCGTGAAGGATAGAGTCATAGAC

TCCCGATTGCAACTGTTCATTACAAAGCCTGGCCTTTATACATGCATTGC

TACAAACAAGCATGGTGAGAAATTCAGTACAGCTAAGGCCGCCGCAACA

ATTTCCATTGCAGAGTGGAGCAAGCCACAAAAAGATAACAAGGGTTACT

GTGCCCAATATCGAGGGGAAGTTTGTAACGCTGTACTTGCTAAGGACGC

TCTCGTCTTCTTGAATACATCCTACGCGGACCCGGAGGAAGCCCAGGAG

CTCTTGGTGCACACTGCATGGAATGAACTTAAAGTAGTGTCCCCTGTATG

CCGGCCAGCCGCGGAAGCGTTGCTCTGTAATCACATTTTCCAAGAATGT

TCACCAGGGGTAGTACCAACGCCTATCCCGATATGTCGGGAATATTGTC

TGGCGGTCAAAGAGCTCTTTTGTGCTAAAGAATGGCTCGTGATGGAGGA

AAAAACTCATCGGGGTTTGTATCGCTCAGAAATGCACCTGCTGAGTGTC

CCAGAATGCTCCAAGTTGCCCAGTATGCACTGGgacCCTACGGCGTGCGC

ACGCTTGCCTCACCTGGACTACAATAAAGAAAATCTGAAAACATTTCCCC

-continued

CTATGACTAGCAGTAAGCCTTCTGTTGATATTCCAAACCTCCCGTCATCC

TCTTCATCTTCTTTCTCTGTCAGCCCGACTTATTCCATGACTGGTGGCGGA

GGTTCTGGAGGTGGAGGTTCCTCCGGAATCTACATCTGGGCGCCCTTGGCC

GGGACTTGTGGGGTCCTTCTCCTGTCACTGGTTATCACCCTTTACTGCAA

ACGGGGCAGAAAGAAACTCCTGTATATATTCAAACAACCATTTATGAGACCA

GTACAAACTACTCAAGAGGAAGATGGCTGTAGCTGCCGATTTCCAGAAGAAG

AAGAAGGAGGATGTGAACTG*AGAGTGAAGTTCAGCAGGAGCGCAGACGCCCC*

*CGCGTACCAGCAGGGCCAGAACCAGCTCTATAACGAGCTCAATCTAGGACGAA*

*GAGAGGAGTACGATGTTTTGGACAAGAGACGTGGCCGGGACCCTGAGATGGG*

*GGGAAAGCCGAGAAGGAAGAACCCTCAGGAAGGCCTGTACAATGAACTGCAG*

*AAAGATAAGATGGCGGAGGCCTACAGTGAGATTGGGATGAAAGGCGAGCGCC*

*GGAGGGGCAAGGGGCACGATGGCCTTTACCAGGGTCTCAGTACAGCCACCAA*

*GGACACCTACGACGCCCTTCACATGCAGGCCCTGCCCCCTCGC*TAA

*IgG Signal peptide*: 1-57 (SEQ ID NO: 2)
MuSK<sub>196A</sub> ECD (codon optimized): 22-493, Mutated sequence is indicated as bold italic and double underline (SEQ ID NO: 29)
GS Linker: 1480-1509 (SEQ ID NO: 17)
CD8 TMD: 1515-1587 (SEQ ID NO: 18)
4-1BB domain: 1588-1713 (SEQ ID NO: 19)
*CD3zeta domain*: 1714-2049 (SEQ ID NO: 20)
Stop codon: 2050-2052

Vector #6: pTRPE.MuSK<sub>196A_opt</sub>.BBz CAAR Amino Acid Sequence (SEQ ID NO: 30)

(SEQ ID NO: 30)
*MEFGLSWLFLVAILKGVQCGS*LPKAPVITTPLETVDALVEEVATFMCAVESYPQ

PEISWTRNKILIKLFDTRYSIRENGQLLTILSVEDSDDGAYCCTANNGVGGAV

ESCGALQVKNIKPKITRPPINVKIIEGLKAVLPCTTMGNPKPSVSWIKGDSPL

RENSRIAVLESGSLRIHNVQKEDAGQYRCVAKNSLGTAYSKVVKLEVEVFAR

ILRAPESHNVTFGSFVTLHCTATGIPVPTITWIENGNAVSSGSIQESVKDRVID

SRLQLFITKPGLYTCIATNKHGEKFSTAKAAATISIAEWSKPQKDNKGYCAQ

YRGEVCNAVLAKDALVFLNTSYADPEEAQELLVHTAWNELKVVSPVCRPAA

EALLCNHIFQECSPGVVPTPIPICREYCLAVKELFCAKEWLVMEEKTHRGLY

RSEMHLLSVPECSKLPSMHWDPTACARLPHLDYNKENLKTFPPMTSSKPSV

DIPNLPSSSSSSFSVSPTYSMTGGGGSGGGGSSGIYIWAPLAGTCGVLLLSLVIT

LYCKRGRKKLLYIFKQPFMRPVQTTQEEDGCSCRFPEEEEGGCEL*RVKFSRSADA*

*PAYQQGQNQLYNELNLGRREEYDVLDKRRGRDPEMGGKPRRKNPQEGLYNELQ*

*KDKMAEAYSEIGMKGERRRGKGHDGLYQGLSTATKDTYDALHMQALPPR*

```
IgG Signal peptide: 1-19 (SEQ ID NO: 10)
MuSK₁₉₆ₐ ECD: 22-493, Mutated sequence is
indicated as bold italic and double
underline (SEQ ID NO: 23)
GS Linker: 494-503 (SEQ ID NO: 12)
CD8 TMD: 506-529 (SEQ ID NO: 13)
4-1BB domain: 530-571 (SEQ ID NO: 14)
CD3zeta domain: 572-683 (SEQ ID NO: 15)
```

The results of the experiments are now described.

Example 1: MuSK CAART Cells

Autoantibodies from MG patients destroy AChR clusters and the NMJ. The anti-AChR antibodies interfere with AChR clusters and the anti-MuSK antibodies disrupt the MuSK/LRP4 complex, which regulates AChR clustering (FIG. 1).

Figure 2:
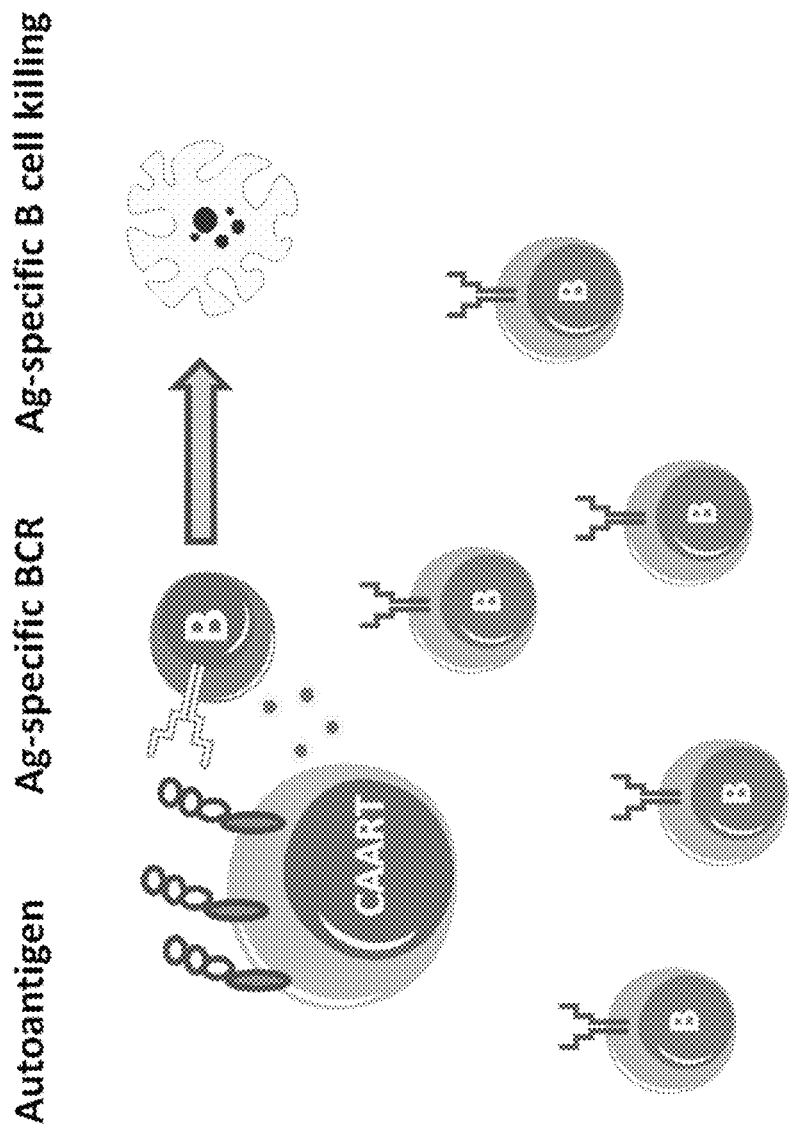
FIG. 2 is an illustration showing that CAAR-T cells specifically kill autoantigen-recognizing B cells. CAAR-T cells express autoantigens on the surface as the extracellular domain of a chimeric immunoreceptor, fused to T cell receptor signaling domains. Ag-specific B cells express a B cell receptor that binds CAAR-T cells. CAAR-T cells secrete mediators (red dots) to kill Ag-specific B cells.

The MuSK CAAR-T cells of this invention specifically kill autoantigen-recognizing B cells. As illustrated in FIG. 2, CAAR-T cells express autoantigens on the surface as the extracellular domain of a chimeric immunoreceptor, fused to T cell receptor signaling domains. Ag-specific B cells express a B cell receptor that binds CAART cells. CAART cells secrete mediators (red dots) to kill Ag-specific B cells.

Figure 3B:
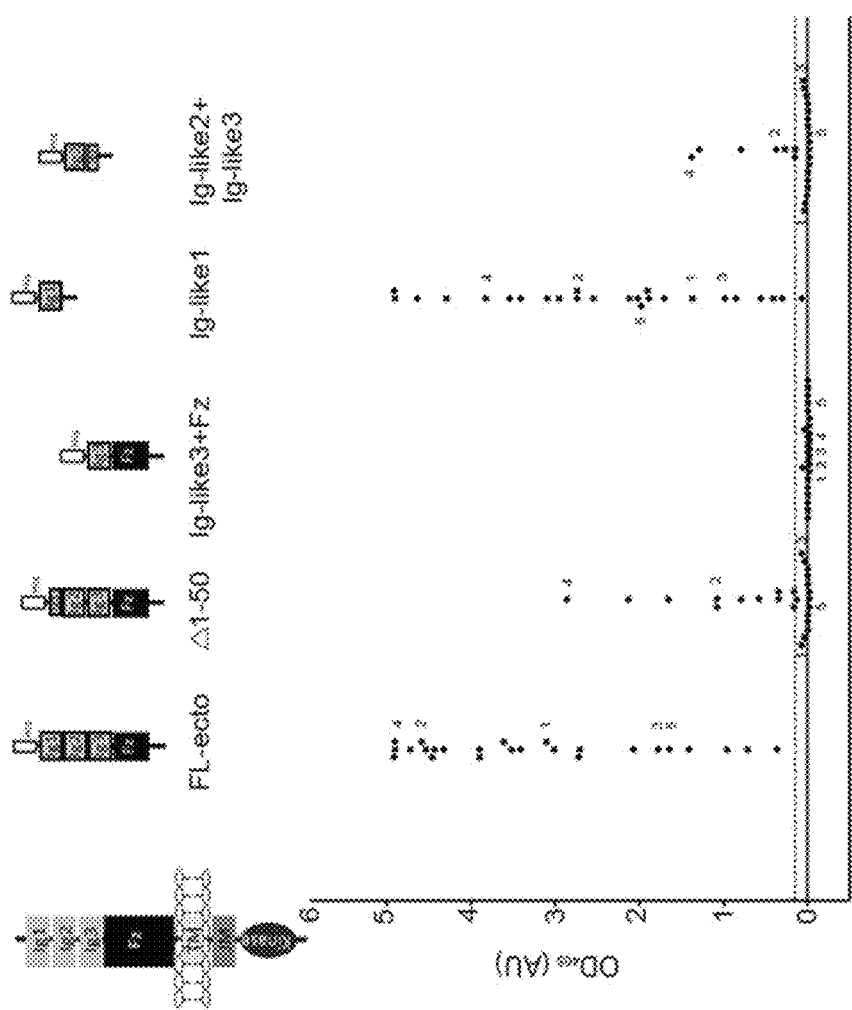

Exemplary MuSK CAAR constructs of the invention, pTRPE.MuSK$_{WT}$.BBz CAAR and pTRPE.MuSK$_{I96A}$.BBz CAAR, are shown in FIGS. 3A-3B.

Figure 4B:
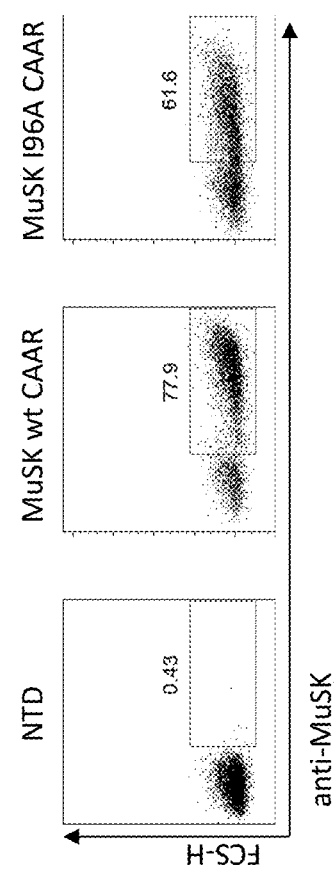

FIGS. 4A-4B illustrate MuSK CAAR constructs and show that CAAR-T cells successfully express MuSK wt and MuSK I96A extracellular domain (ECD) on the cell surface. FIG. 4A is a schematic diagram of MuSK wild type (wt)/I96A CAAR constructs. An isoleucine at amino acid position 96 of the MuSK wt ECD is mutated into alanine and indicated as a white box. MuSK wt/I96A CAAR in pTRPE lentiviral vector was transduced into primary human CD3⁺ T cells. At day five after transduction, surface expression of MuSK wt/I96A CAAR was detected using anti-MuSK antibody 4A3. The results are shown in FIG. 4B.

Figure 5A:
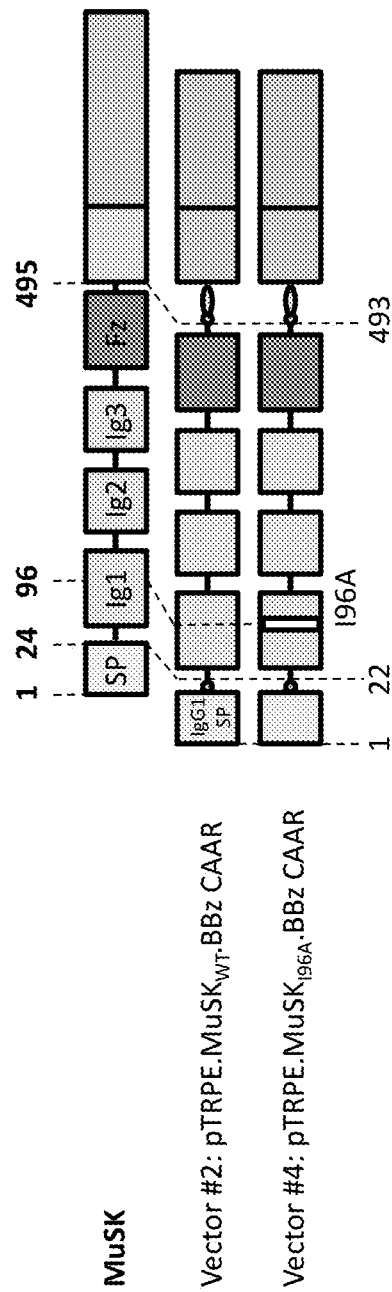
FIGS. 5A-5B are a series of diagrams, graphs and histograms demonstrating the expression of MuSK CAARs on the surface of transfected cells.
Figure 5B:
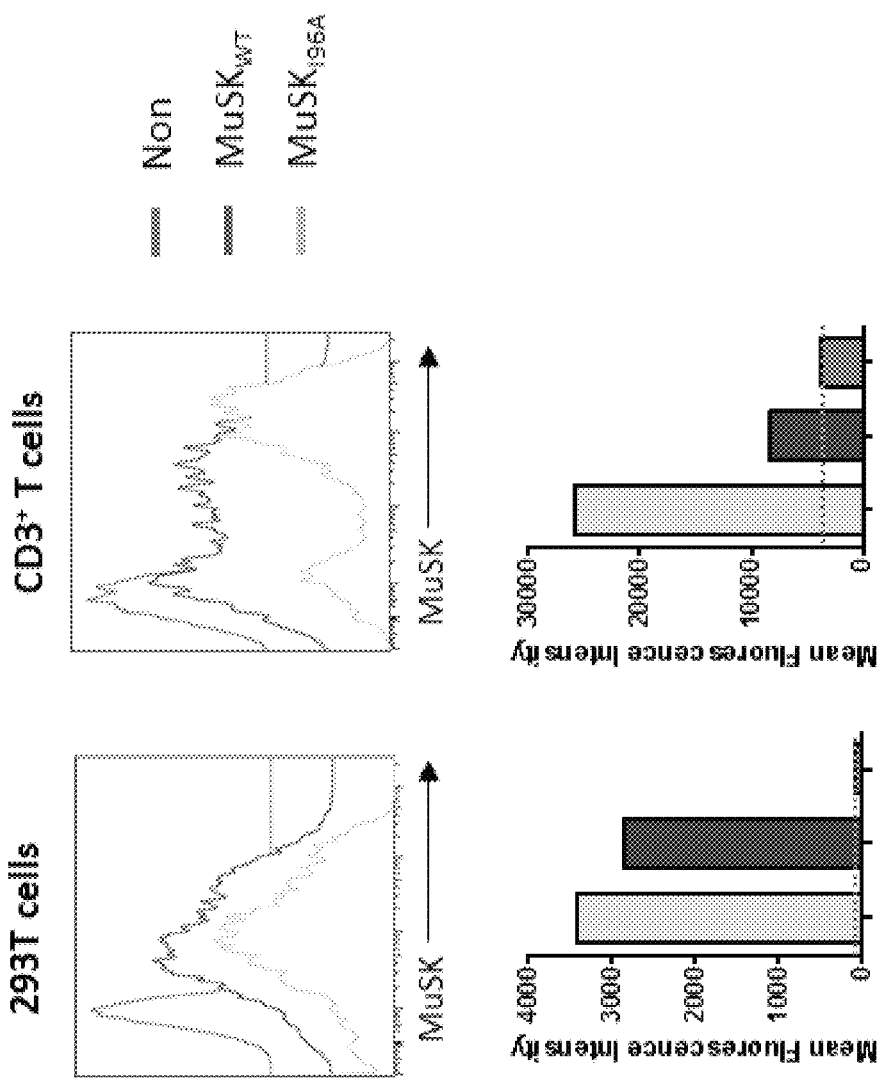

The expression of MuSK CAARs on the surface of transfected cells is demonstrated in FIGS. 5A-5B. As shown in FIG. 5B, upper panel, the surface expression of MuSK CAARs on non-transfected cells (Non, red), MuSK$_{WT}$ CAAR transfected cells (middle), and MuSK$_{I96A}$ (right) were detected using anti-MuSK-APC antibody. The histograms in FIG. 5B, lower panel, summarize the mean fluorescence intensity of anti-MuSK-APC antibody staining in the upper panel.

Figure 6:
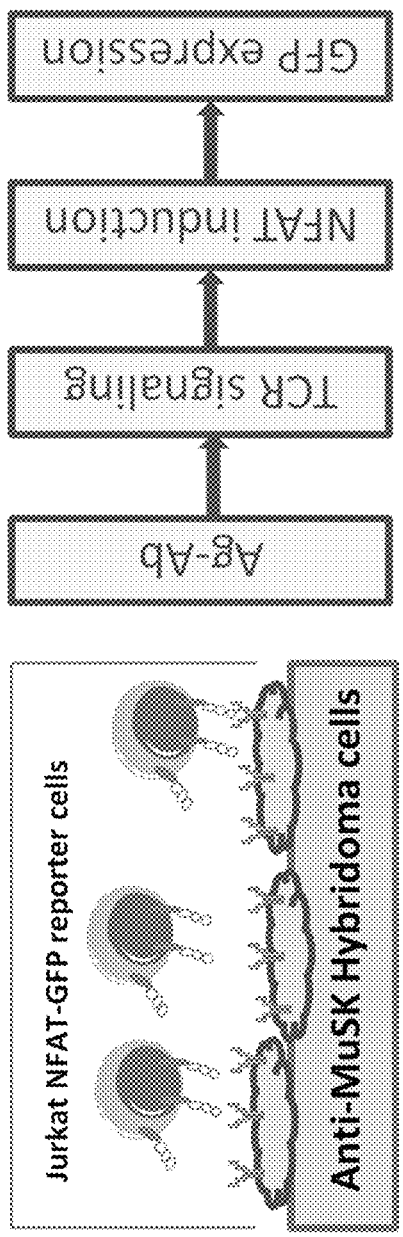
FIG. 6 is a series of diagrams and flow cytometry plots showing that MuSK CAARs recognize anti-MuSK BCRs and activate TCR signaling. Jurkat NFAT-GFP reporter cells expressing MuSK CAARs were co-cultured with anti-MuSK BCR-expressing hybridoma cells. Activated TCR signaling in the Jurkat NFAT-GFP reporter cells induces GFP expression. MuSK CAARs were activated by anti-MuSK BCRs and successfully initiated TCR signaling (bold rectangle). (Non=Non-transduced. Flow cytometry analysis was conducted at 12 h after co-culture with 4A3 hybridoma cells. Jurkat cells were stained with anti-CD3-APC antibody to distinguish 4A3 hybridoma cells. Jurkat NFAT-GFP cells induced GFP expression when TCR signaling was transduced).
Figure 6:
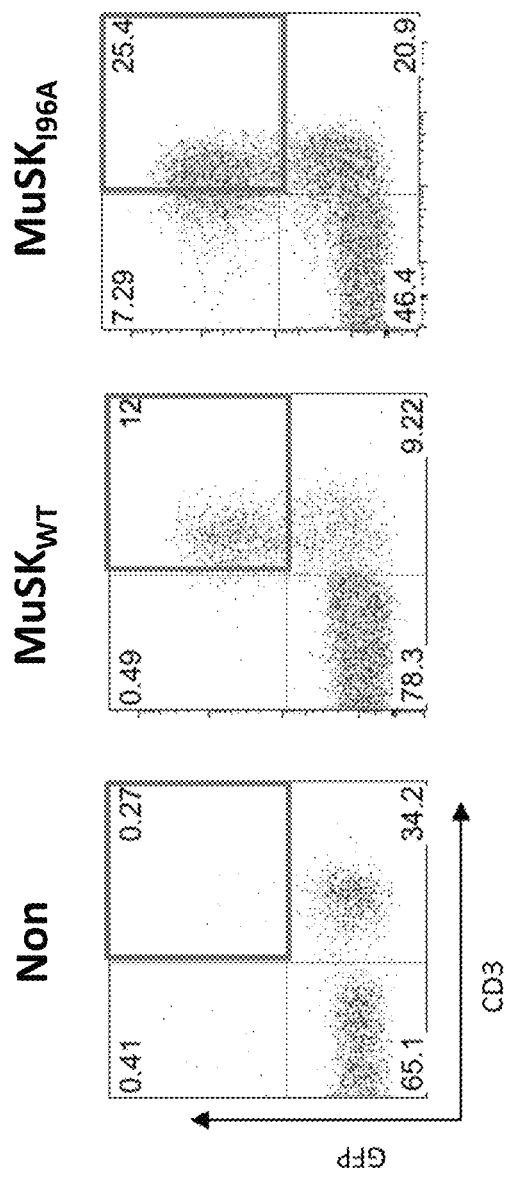

FIG. 6 depicts that MuSK CAARs recognize anti-MuSK BCRs and activate TCR signaling. MuSK CAARs were expressed in Jurkat NFAT-GFP reporter cells, which were co-cultured with anti-MuSK BCR-expressing hybridoma cells. Activated TCR signaling in the Jurkat NFAT-GFP reporter cells induces GFP expression. MuSK CAARs were activated by anti-MuSK BCRs and successfully initiated TCR signaling (bold rectangle).

Example 2: MuSK CAAR-T Cell Killing Assays

Figure 7:
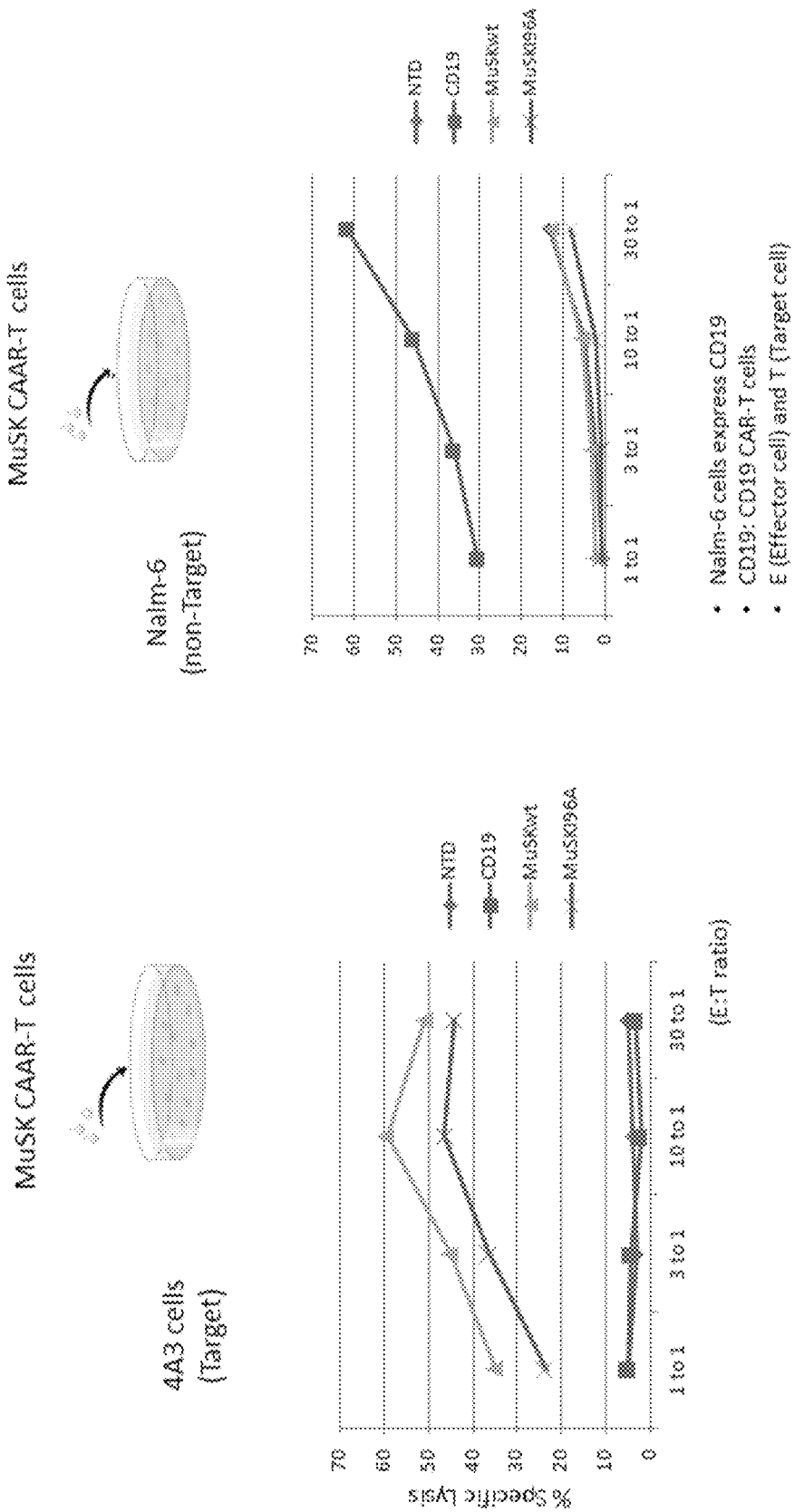
FIG. 7 is a series of images and graphs demonstrating that MuSK CAAR-engineered primary human T cells kill 4A3 anti-MuSK hybridoma cells based on the percent specific lysis of $^{51}$Cr-labeled 4A3 cells after 4 hours of co-incubation with MuSK CAAR-T cells. In comparison, MuSK CAAR-T cells do not kill non-target Nalm-6 cells, indicating the specificity of target cell killing by MuSK CAAR-T cells.

FIG. 7 shows that MuSK CAAR-engineered primary human T cells kill 4A3 anti-MuSK hybridoma cells based on the percent specific lysis of ⁵¹Cr-labeled 4A3 cells after 4 hours of co-incubation with MuSK CAAR-T cells. In comparison, CAAR-T cells do not kill non-target Nalm-6 cells, indicating specificity of target cell killing by MuSK CAAR-T cells.

Figure 8:
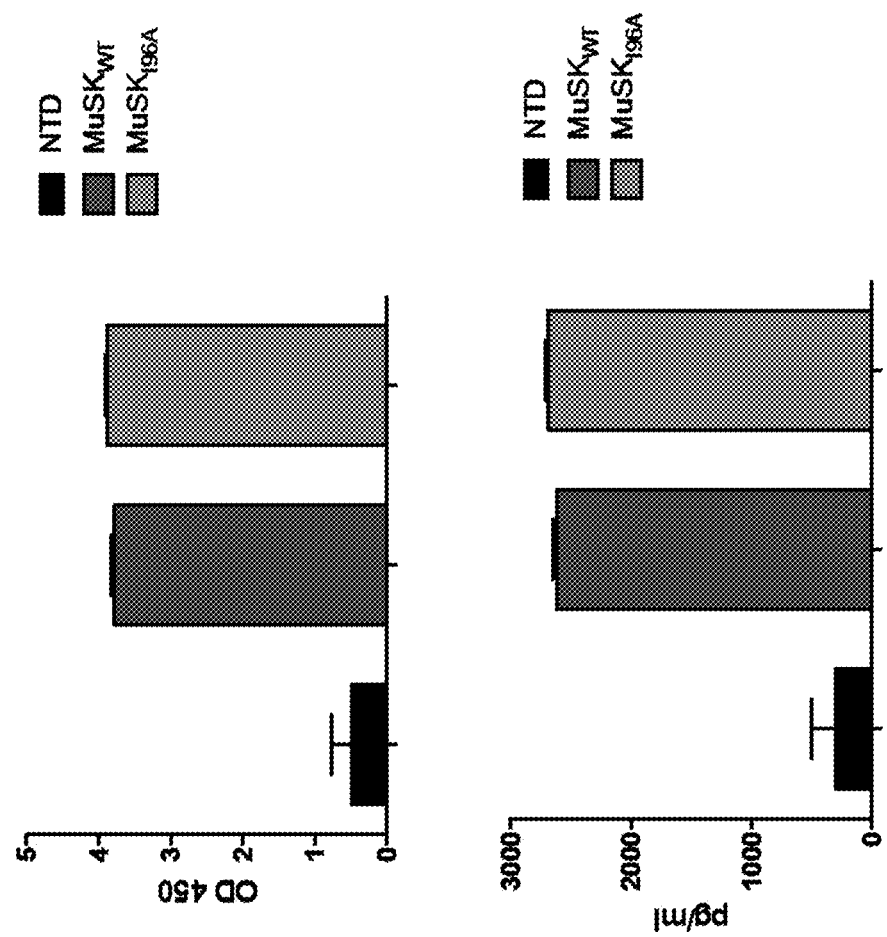
FIG. 8 is a series of histograms showing that MuSK CAAR T cells, but not non-transduced T cells, secrete interferon gamma after 4A3 target cell engagement.

As shown in FIG. 8, MuSK CAAR T cells, but not non-transduced T cells, secrete interferon gamma after 4A3 target cell engagement. The depicted MuSK CAARs recognize anti-MuSK BCRs and successfully initiate TCR signaling, which is required for the effector function of CAART cells to eliminate target cells.

Figure 9A:
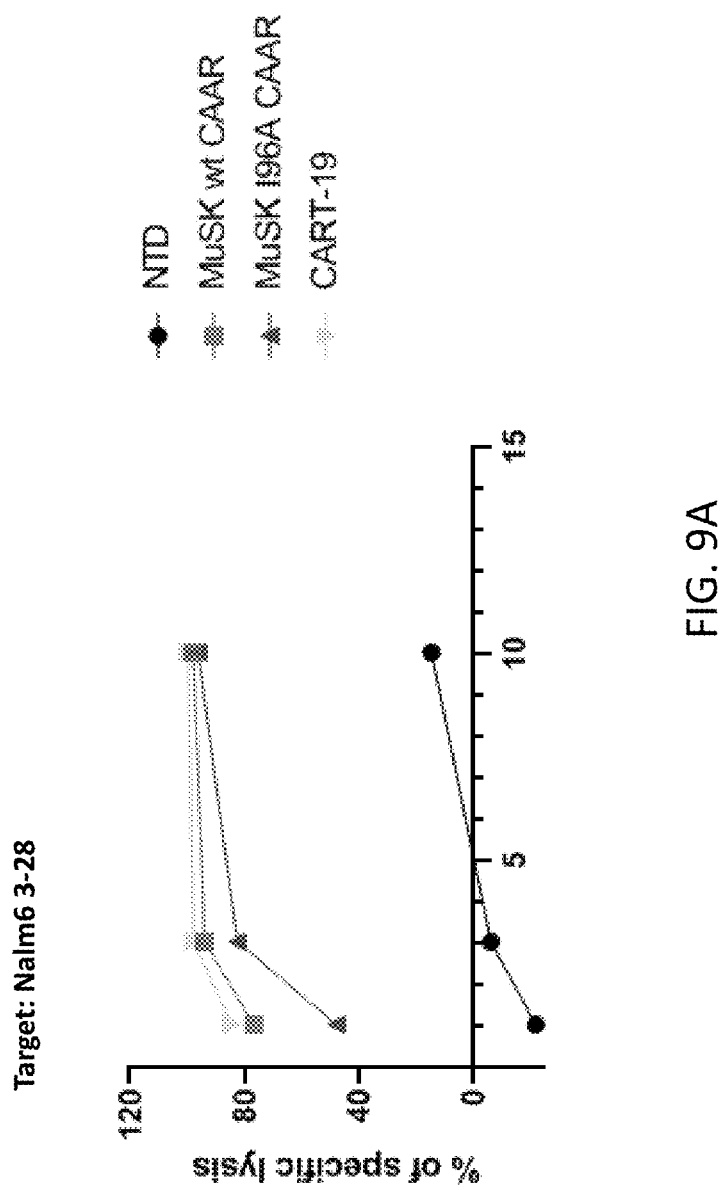
FIGS. 9A-9B illustrate that MuSK wt/I96A CAAR-T cells specifically kill Nalm6 B cells engineered to express anti-MuSK B cell receptor 3-28 (FIG. 9A), but do not kill Nalm-6 wt cells (FIG. 9B). Nalm-6 wt cells stably expressed click-beetle luciferase green (CBG) protein, which emits in the green fluorescent protein (GFP) channel, as well as CD79a/CD79b, which is necessary for expression of surface immunoglobulin as a B cell receptor (BCR). To generate Nalm6 3-28 (anti-MuSK BCR) cells as a MuSK wt/I96A CAAR-T target cell, 3-28 IgG4 BCR was introduced into Nalm-6/CBG/CD79a/CD79b cells and GFP$^+$hIgG$^+$ cells were sorted. Sorted Nalm6 3-28 cells or Nalm6 wt cells were co-cultured with MuSK wt/I96A CAAR-T cells or CART-19 cells at indicated effector: target (E:T) ratio for 22 hours. Luciferase activity in Nalm6 cells was detected by adding luciferin to a final concentration of 150 μg/ml. Percent specific lysis was calculated by following equation: % of specific lysis=[(experimental sample–spontaneous cell death sample)/(maximum cell death sample–spontaneous cell death sample)]*100. Maximum cell death was induced by 5% SDS lysis.
Figure 9B:
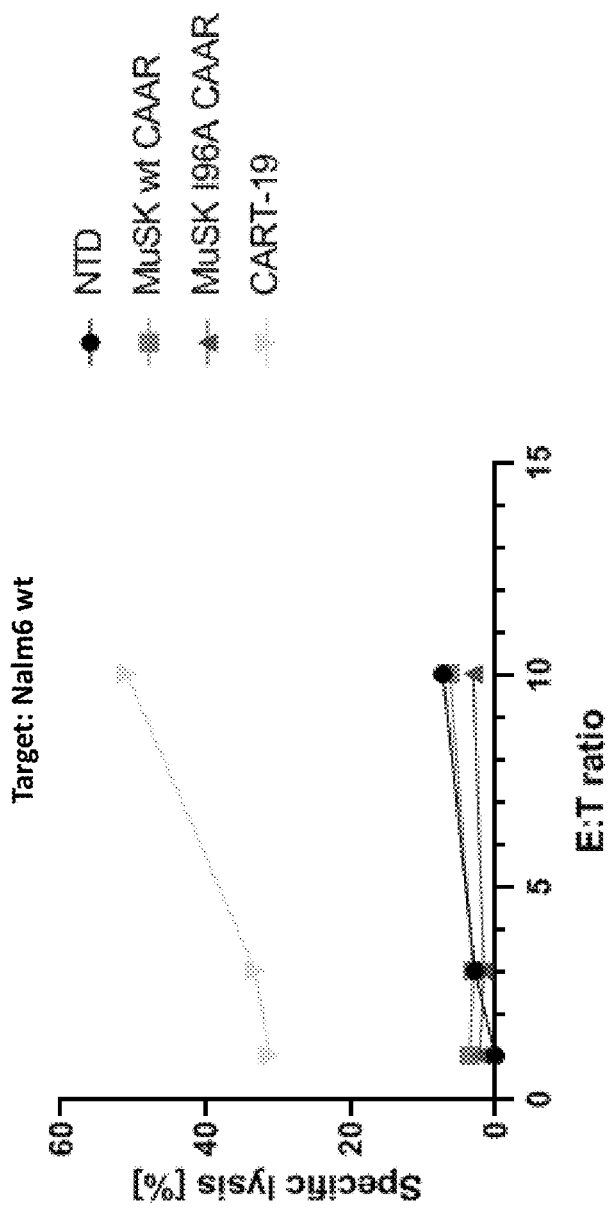

MuSK wt/I96A CAAR-T cells specifically kill Nalm6 B cells engineered to express anti-MuSK B cell receptor 3-28, as shown in FIGS. 9A-9B. Nalm-6 wt cells stably expressed click-beetle luciferase green (CBG) protein, which emits in the green fluorescent protein (GFP) channel, as well as CD79a/CD79b, which is necessary for expression of surface immunoglobulin as a B cell receptor (BCR). To generate Nalm6 3-28 (anti-MuSK BCR) cells as a MuSK wt/I96A CAAR-T target cell, 3-28 IgG4 BCR were introduced into Nalm-6/CBG/CD79a/CD79b cells and GFP⁺hIgG⁺ cells were sorted. Sorted Nalm6 3-28 cells or Nalm6 wt cells were co-cultured with MuSK wt/I96A CAAR-T cells or CART-19 cells at indicated effector: target (E:T) ratio for 22 hours. Luciferase activity in Nalm6 cells was detected by adding luciferin to a final concentration of 150 Percent specific lysis is calculated by following equation: % of specific lysis= [(experimental sample−spontaneous cell death sample)/ (maximum cell death sample−spontaneous cell death sample)]*100. Maximum cell death was induced by 5% SDS lysis.

Figure 10:
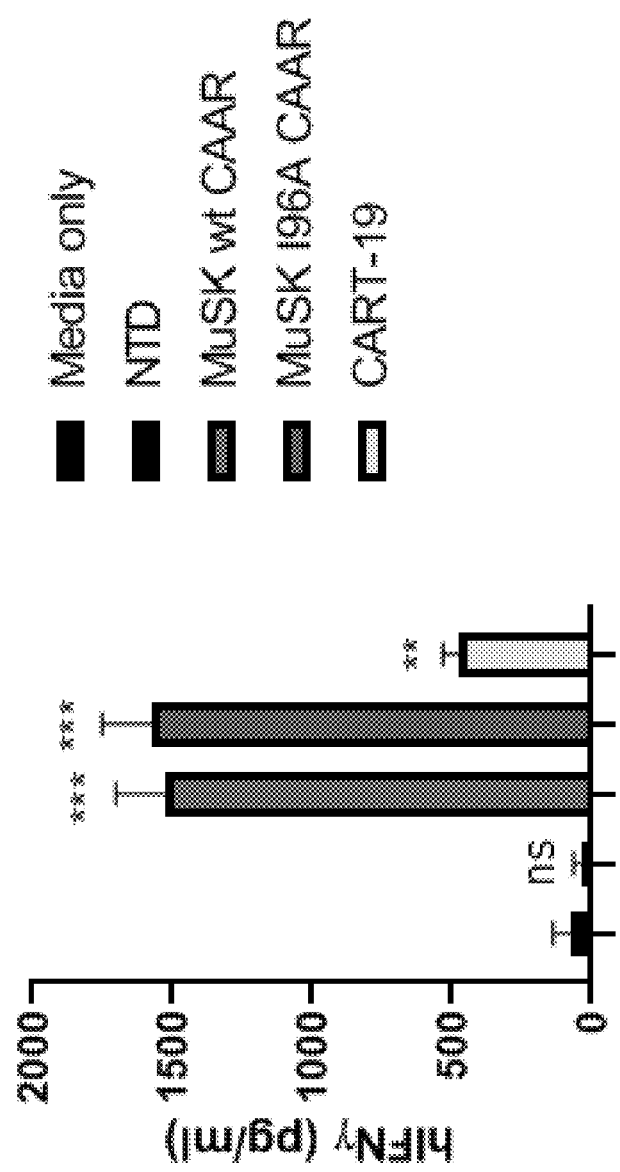
FIG. 10 illustrates that MuSK wt/I96A CAAR-T cells secrete IFNγ following interaction with Nalm6 B cells engineered to express anti-MuSK B cell receptor 3-28. After analyzing luciferase activity as shown in FIGS. 9A-9B, the supernatant was collected after spin-down. Human IFNγ was detected by Human IFN-gamma DuoSet ELISA kit (R&D Systems). Unpaired two-tailed t test with media only sample; ns: non-significant, : <0.005, *: <0.0005. Graph columns from left to right: Media only, NTD, MuSK wt CAAR, MuSK I96A CAAR, and CART-19.

MuSK wt/I96A CAAR-T cells secrete IFNγ following interaction with Nalm6 B cells engineered to express anti-MuSK B cell receptor 3-28, as shown in FIG. 10. After analyzing luciferase activity as shown in FIGS. 9A-9B, the supernatant was collected after spin-down. Human IFNγ was detected by Human IFN-gamma DuoSet ELISA kit (R&D Systems). Unpaired two-tailed t test with media only sample; ns: non-significant, : <0.005, *: <0.0005.

MuSK wt/I96A CAAR-T cells kill anti-MuSK antibody producing 4A3 hybridoma cells and secrete IFNγ, as shown in FIGS. 11A-11B. FIG. 11A shows that 4A3 hybridoma cells were labeled using ⁵¹Cr and co-cultured for 21 hours with MuSK wt/I96A CAAR-T cells or CART-19 cells. Percent specific lysis was calculated by following equation: % of specific lysis=[(experimental sample−spontaneous cell death sample)/(maximum cell death sample−spontaneous cell death sample)]*100. Maximum cell death was induced by adding 5% SDS (final 5%). FIG. 11B shows that MuSK wt/I96A CAAR-T cells were co-cultured with unlabeled 4A3 hybridoma cells for 21 hours. The supernatant was collected after spin-down. Human IFNγ was detected by Human IFN-gamma DuoSet ELISA kit (R&D Systems).

Figure 12A:
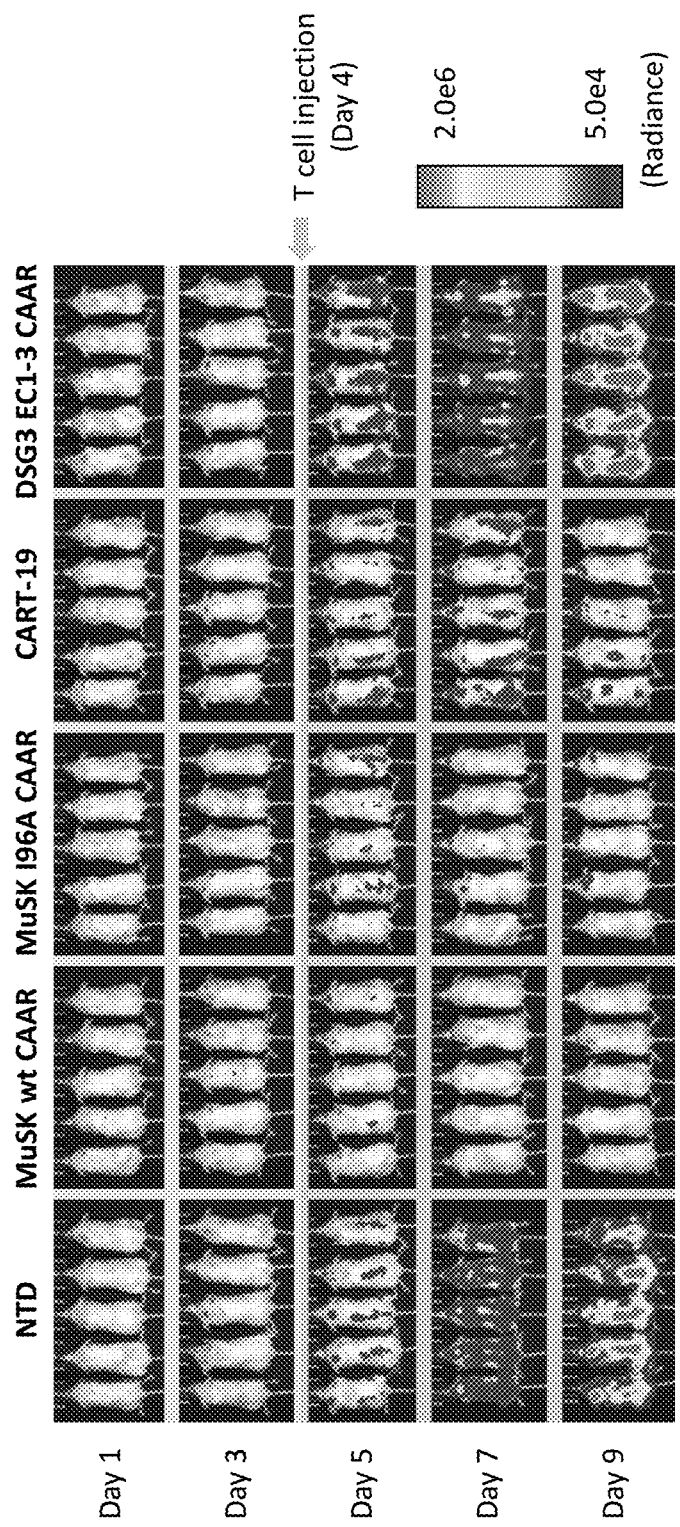
FIGS. 12A-12B illustrate that MuSK wt/I96A CAAR-T cells eliminate anti-MuSK target cells in vivo.
Figure 12B:
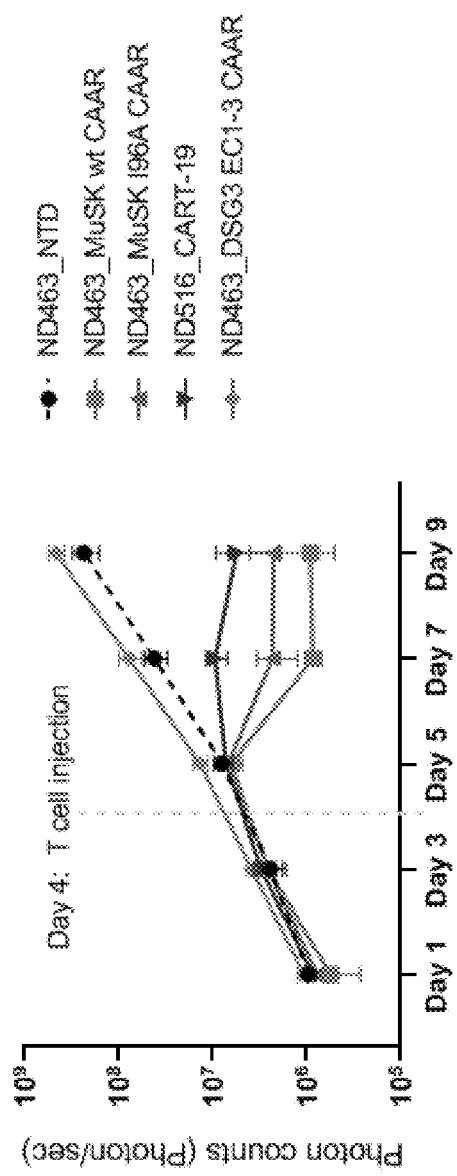

MuSK wt/I96A CAAR-T cells eliminate anti-MuSK target cells in vivo, as shown in FIGS. 12A-12B. FIG. 12A shows that $0.5 \times 10^6$ CBG+hIgG+ Nalm6 3-28 cells were injected intravenously into NSG mice after pre-treatment with intravenous immunoglobulin (IVIG, Privigen, 600 mg/kg intraperitoneal injection daily for 2 days). After 4 days, $5 \times 10^6$ indicated CAAR- or CAR-T cells were injected intravenously (orange arrow). Non-transduced (NTD) T cells and Desmoglein (DSG) 3 EC1-3 CAAR-T cells were considered as a negative control and CART-19 cells were used as a positive control since Nalm6 cells express CD19. Bioluminescence was quantified with an IVIS Lumina at day 1, 3, 5, 7, and 9. Simultaneously, 600 mg/kg IVIG was also administered every two days intraperitoneally. Total flux was quantified using Living Image 4.5 software (PerkinElmer). Images were consecutively taken with a 1 minute interval. FIG. 12B shows bioluminescence flux (photons/sec) for each treatment group in FIG. 12A, which illustrate that MuSK wt/I96A CAAR T cells control anti-MuSK Nalm6 target cells, comparable in efficacy to CART-19 cells, whereas negative control NTD and DSG3 EC1-3 CAAR T cells do not control anti-MuSK Nalm6 target cell outgrowth.

Figure 13A:
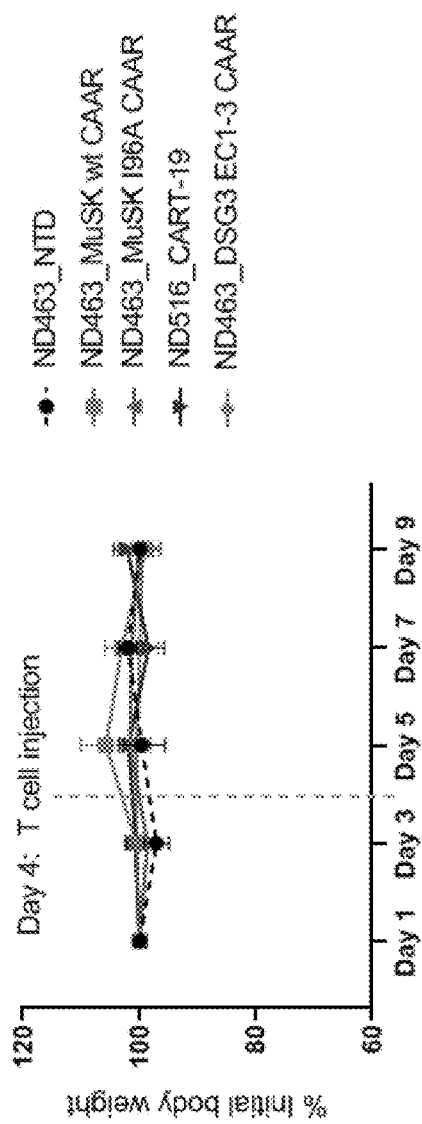
FIGS. 13A-13B illustrate that MuSK wt/I96A CAAR-T cells secrete IFNγ to eliminate anti-MuSK target cells in vivo.
Figure 13B:
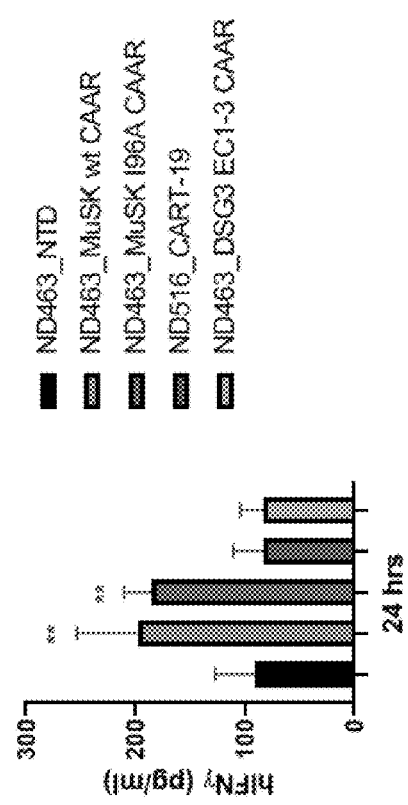

MuSK wt/I96A CAAR-T cells secrete IFNγ to eliminate anti-MuSK target cells in vivo, as shown in FIGS. 13A-13B. Mouse body weight was measured right after the imaging in FIG. 12A. Percentage of initial body weight was calculated relative to Day 1 (100%). The results are shown in FIG. 13A. At 24 hours after T cell injection, blood samples were collected by retro-orbital bleeding. Mouse sera were kept at $-20°$ C. for further analysis. Human IFNγ was detected by Human IFN-gamma DuoSet ELISA kit (R&D Systems). Unpaired two-tailed t test with ND463 NTD; ns: non-significant, **: <0.005. The results are shown in FIG. 13B.

The MuSK CAARs constructs of the invention: Vector #1, #2, #3,#4, #5, and #6 are shown in FIG. 14. Codon-optimized domains are indicated as a light gray colored-box.

Figure 15:
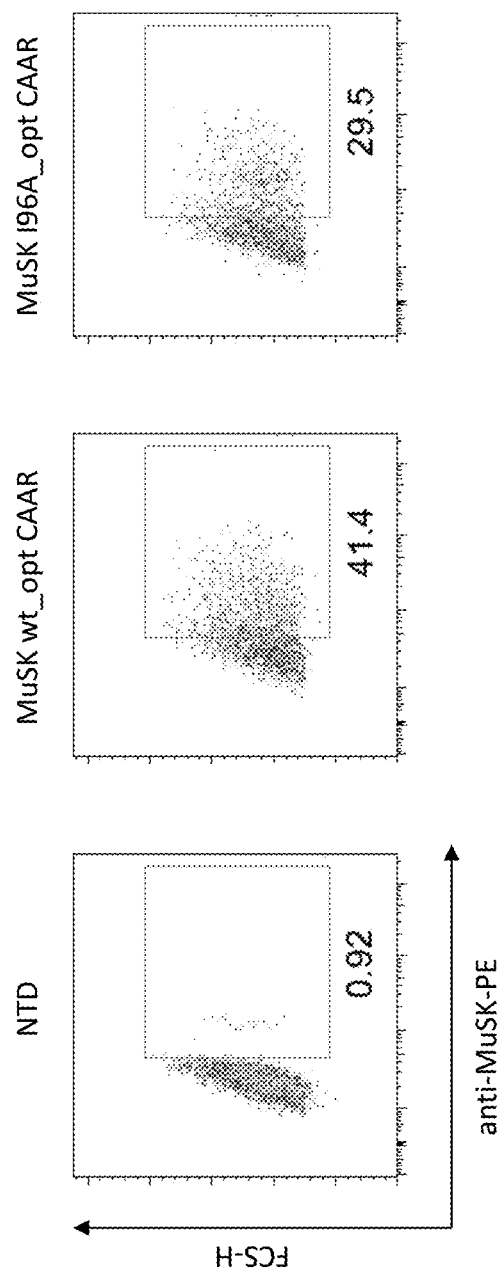
FIG. 15 illustrates that codon-optimized MuSK wt/I96A CAARs are expressed in human primary CD3$^+$ T cells. MuSK wt_opt or MuSKI96A_opt CAAR in pTRPE lentiviral vector was transduced into primary human CD3$^+$ T cells. At day five after transduction, surface expression of MuSK wt_opt or MuSK I96A_opt was detected using anti-MuSK (4A3) PE-conjugated antibody.

Codon-optimized MuSK wt/I96A CAARs were expressed in human primary CD3+ T cells, as shown in FIG. 15. MuSK wt_opt or MuSK I96A_opt CAAR in pTRPE lentiviral vector were transduced into primary human CD3+ T cells. At day five after transduction, surface expression of MuSK wt_opt or MuSK I96A_opt was detected using anti-MuSK (4A3) PE-conjugated antibody.

Figure 16:
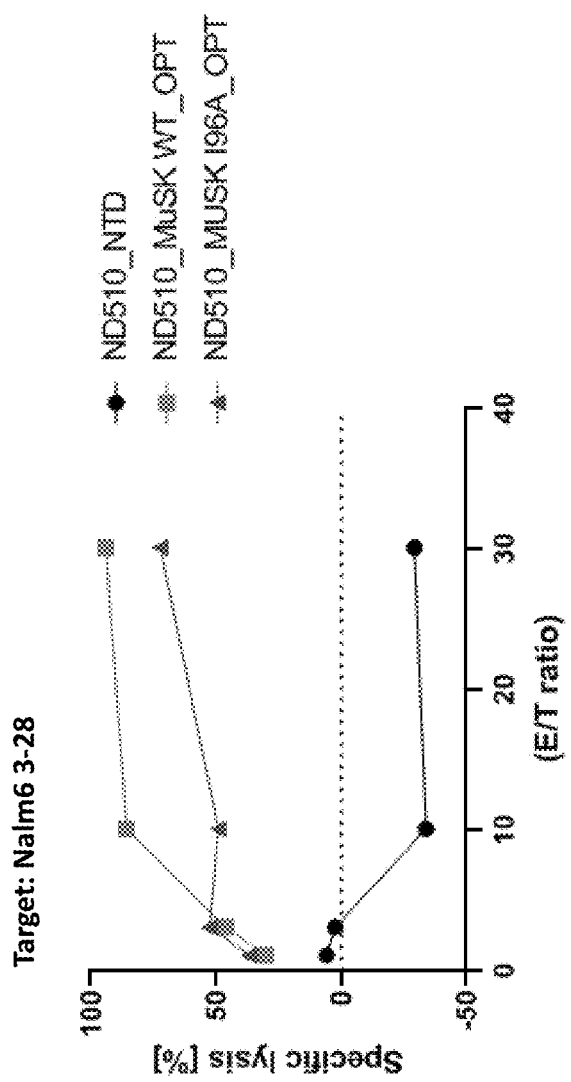
FIG. 16 illustrates that codon-optimized MuSK wt/I96A CAAR-T cells kill Nalm6 B cells engineered to express anti-MuSK B cell receptor 3-28.

Codon-optimized MuSK wt/I96A CAAR-T cells kill Nalm6 B cells engineered to express anti-MuSK B cell receptor 3-28, as shown in FIG. 16.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A polynucleotide encoding a chimeric autoantibody receptor (CAAR), wherein the polynucleotide encodes an extracellular domain comprising a muscle-specific kinase (MuSK) autoantigen comprising the amino acid sequence of SEQ ID NO: 11 or 23, a CD8 alpha transmembrane domain comprising the amino acid sequence of SEQ ID NO: 13, a 4-1BB intracellular domain comprising the amino acid sequence of SEQ ID NO: 14, and a CD3 zeta signaling domain comprising the amino acid sequence of SEQ ID NO: 15.

2. The polynucleotide of claim 1, wherein the MuSK autoantigen is encoded by a nucleic acid sequence selected from the group consisting of SEQ ID NOs: 3, 6, 26 and 29.

3. The polynucleotide of claim 1, wherein the CD8 alpha transmembrane domain is encoded by a nucleic acid sequence comprising SEQ ID NO: 5 or 18.

4. The polynucleotide of claim 1, wherein the 4-1BB intracellular domain is encoded by a nucleic acid sequence comprising SEQ ID NO: 7 or 19.

5. The polynucleotide of claim 1, wherein the CD3 zeta signaling domain is encoded by a nucleic acid sequence comprising SEQ ID NO: 8 or 20.

6. The polynucleotide of claim 1, wherein the CAAR is encoded by a nucleic acid sequence selected from the group consisting of SEQ ID NOs: 1, 16, 21, 24, 25 and 28.

7. The polynucleotide of claim 1, wherein the CAAR comprises an amino acid sequence selected from the group consisting of SEQ ID NOs: 9, 22, 27 and 30.

8. A vector comprising the polynucleotide of claim 1.

9. The polynucleotide of claim 7, wherein the CAAR comprises the amino acid sequence of SEQ ID NO: 27.

10. The vector of claim 8, wherein the vector is a lentiviral vector.

11. The vector of claim 8, wherein the vector is an RNA vector.

12. The vector of claim 8, wherein the vector further comprises an inducible promoter operably linked to the polynucleotide.

13. A chimeric autoantibody receptor (CAAR) comprising an extracellular domain comprising a muscle-specific kinase (MuSK) autoantigen comprising the amino acid sequence of SEQ ID NO: 11 or 23, a CD8 alpha transmembrane domain comprising the amino acid sequence of SEQ ID NO: 13, a 4-1BB intracellular domain comprising the amino acid sequence of SEQ ID NO: 14, and a CD3 zeta signaling domain comprising the amino acid sequence of SEQ ID NO: 15.

14. The CAAR of claim 13, wherein the CAAR comprises an amino acid sequence selected from the group consisting of SEQ ID NOs: 9, 22, 27 and 30.

15. The CAAR of claim 14, wherein the CAAR comprises the amino acid sequence of SEQ ID NO: 27.

* * * * *